US011091524B1

(12) United States Patent
Hermonat

(10) Patent No.: US 11,091,524 B1
(45) Date of Patent: Aug. 17, 2021

(54) COMPOSITIONS FOR TREATMENT OF VASCULAR DISEASE

(71) Applicant: Houston Gene Therapeutics LLC, Surfside Beach, TX (US)

(72) Inventor: Paul L. Hermonat, Surfside Beach, TX (US)

(73) Assignee: HOUSTON GENE THERAPEUTICS LLC, Surfside Beach, TX (US)

( * ) Notice: Subject to any disclaimer, the term of this patent is extended or adjusted under 35 U.S.C. 154(b) by 0 days.

(21) Appl. No.: 17/078,163

(22) Filed: Oct. 23, 2020

Related U.S. Application Data

(60) Provisional application No. 63/013,869, filed on Apr. 22, 2020.

(51) Int. Cl.
| | | |
|---|---|---|
| *C07K 14/47* | (2006.01) | |
| *C07K 14/54* | (2006.01) | |
| *A61P 9/10* | (2006.01) | |
| *A61K 9/00* | (2006.01) | |

(52) U.S. Cl.
CPC ........ *C07K 14/5428* (2013.01); *A61K 9/0019* (2013.01); *A61P 9/10* (2018.01); *C07K 14/47* (2013.01); *C07K 14/4705* (2013.01)

(58) Field of Classification Search
CPC ................ C07K 14/5428; C07K 14/47; C07K 14/4705; A61P 9/10; A61K 9/0019
See application file for complete search history.

(56) References Cited

U.S. PATENT DOCUMENTS

| | | |
|---|---|---|
| 8,058,065 B2 | 11/2011 | Yamanaka et al. |
| 8,129,187 B2 | 3/2012 | Yamanaka et al. |
| 8,163,896 B1 | 4/2012 | Bentwich |
| 8,207,316 B1 | 6/2012 | Bentwich |
| 8,278,104 B2 | 10/2012 | Yamanaka et al. |
| 9,057,736 B2 | 6/2015 | Urdea et al. |
| 9,340,772 B2 | 5/2016 | Bhatia et al. |
| 9,689,880 B2 | 6/2017 | Urdea et al. |
| 10,076,574 B2 | 9/2018 | Wang et al. |
| 10,221,396 B2 | 3/2019 | Brown et al. |
| 10,260,048 B2 | 4/2019 | Mack |
| 10,324,092 B2 | 6/2019 | Ciceri et al. |
| 10,822,587 B2 | 11/2020 | Regev et al. |
| 2002/0176852 A1 | 11/2002 | Lambeth et al. |
| 2006/0292621 A1 | 12/2006 | Case et al. |
| 2011/0124560 A1 | 5/2011 | Greene et al. |
| 2015/0098925 A1 | 4/2015 | Chiriva-Internati |
| 2015/0216999 A1 | 8/2015 | Chiriva-Internati |
| 2016/0263247 A1 | 9/2016 | Chiriva-Internati |
| 2016/0331844 A1 | 11/2016 | Fotin-Mleczek et al. |

FOREIGN PATENT DOCUMENTS

| | | |
|---|---|---|
| WO | 2015054258 A1 | 4/2015 |
| WO | 2015160977 A1 | 10/2015 |
| WO | 2016138213 A1 | 9/2016 |

OTHER PUBLICATIONS

Li Z, et al., "FOXP3+ regulatory T cells and their functional regulation." Cell Mol Immunol. 2015, 12(5):588-65.
Liu Y, et al., "Inhibition of atherogenesis in LDLR knockout mice by systemic delivery of adeno-associated virus type 2-hIL-10." Atherosclerosis. 2006 (Epub 2005), 188(1):19-27.
Liu Y, et al., "Rapid induction of cytotoxic T-cell response against cervical cancer cells by human papillomavirus type 16 E6 antigen gene delivery into human dendritic cells by an adeno-associated virus vector." Cancer Gene Ther. 2001, 8(12):948-57.
Manea A, et al., "JAK/STAT signaling pathway regulates Nox1 and Nox4-based NADPH Oxidase in human aortic smooth muscle cells." Arterioscler Thromb Vasc Biol. 2010 (Epub 2009), 30(1):105-12.
Maris CH, et al., "Interleukin-10 plays an early role in generating virus-specific T cell anergy." BMC Immunol. 2007, 8:8, doi:10.1186/1471-2172-8-8, 9 pages.
Maynard CL, et al., "Contrasting roles for all-trans retinoic acid in TGF-β-mediated induction of Foxp3 and IL10 genes in developing regulatory T cells." J Exp Med. 2009, 206(2):343-57.
Mercurio F and Manning AM, "NF-κb as a primary regulator of the stress response." Oncogene. 1999, 18 (45):6163-71.
Neyns B, et al., "Characterization of permanent cell lines that contain the AAV2 rep-cap genes on an Epstein-Barr-virus-based episomal plasmid." Intervirology. 2001, 44(4):255-63.
Nguyen Dinh Cat A, et al., "Angiotensin II, NADPH oxidase, and redox signaling in the vasculature." Antioxid Redox Signal. 2013 (Epub 2012), 19(10):1110-20.
Pan JH, et al., "Macrophage migration inhibitory factor deficiency impairs atherosclerosis in low-density lipoprotein receptor-deficient mice." Circulation. 2004, 109(25):3149-53.
Ren J, et al. "Foxp1 is critical for the maintenance of regulatory T-cell homeostasis and suppressive function." PLoS Biol. 2019, 17(5):e3000270, doi: 10.1371/journal.pbio.3000270, 29 pages.
Rudra D, et al., "Transcription factor Foxp3 and its protein partners form a complex regulatory network." Nat Immunol. 2012, 13(10):1010-9, author manuscript version, 27 pages.

(Continued)

*Primary Examiner* — Catherine S Hibbert
(74) *Attorney, Agent, or Firm* — McNeill Baur PLLC

(57) ABSTRACT

Provided are various embodiments relating to compositions and methods for treating vascular disease, including core NOX1 promoters and variants thereof for regulating expression of transgenes in response to vascular pathology and allowing for increased transgene loading capacity. Also provided are variant FOXP polypeptides having a zinc finger and leucine zipper region of a different FOXP polypeptide. Further provided are vectors comprising the core NOX1 promoters and/or a coding sequence for variant FOXP polypeptides described herein and optionally coding sequence(s) for one or more additional therapeutic polypeptide(s), such as IL10, for treating inflammation-associated diseases, such as vascular disease. Also provided is a screening model for testing therapeutic agents capable of treating established and ongoing atherosclerotic pathology.

30 Claims, 18 Drawing Sheets

Specification includes a Sequence Listing.

(56) References Cited

OTHER PUBLICATIONS

Song X, et al., "Structural and biological features of FOXP3 dimerization relevant to regulatory T cell function." Cell Rep. 2012, 1(6):665-75.
Stewart J, et al., "Understanding vascular ultrasonography." Mayo Clin Proc. 1992, 67(12):1186-96.
Takano T and Cybulsky AV, "Complement C5b-9-mediated arachidonic acid metabolism in glomerular epithelial cells: role of cyclooxygenase-1 and -2." Am J Pathol. 2000, 156(6):2091-101.
Udalova IA, et al., "Quantitative prediction of NF-kappa B DNA-protein interactions." Proc Natl Acad Sci USA. 2002, 9(12):8167-72.
Valente AJ, et al., "Regulation of NOX1 expression by GATA, HNF-1alpha, and Cdx transcription factors." Free Radic Biol Med. 2008 (Epub 2007), 44(3): 430-43.
Voleti B and Agrawal A, "Regulation of basal and induced expression of C-reactive protein through an overlapping element for OCT-1 and NF-kappaB on the proximal promoter" J Immunol. 2005, 175(5):3386-90.
Wan F and Lenardo M, "Specification of DNA Binding Activity of NF-κB Proteins." Cold Spring Harb Perspect Biol. 2009, 1(4):a000067, 16 pages.
Wang B, et al., "Multiple domains define the expression and regulatory properties of Foxp1 forkhead transcriptional repressors." J Biol Chem. 2003, 278(27):24259-68.
Wong D, et al., "Extensive characterization of NF-κB binding uncovers non-canonical motifs and advances the interpretation of genetic functional traits." Genome Biol. 2011, 12(7):R70, doi: 10.1186/gb-2011-12-7-r70, pp. 1-18.
Yang AT, et al., "TGF-β1 induces the dual regulation of hepatic progenitor cells with both anti- and proliver fibrosis", Stem Cells Int. 2016, 2016:1492694. doi: 10.1155/2016/1492694. Epub 2015, 13 pages.
Zadelaar S, et al., "Mouse models for atherosclerosis and pharmaceutical modifiers." Arterioscler Thromb Vasc Biol. 2007, 27(8):1706-21.
Zeni E, et al., "Macrophage expression of interleukin-10 is a prognostic factor in nonsmall cell lung cancer." Eur Respir J. 2007, 30(4):627-32.
Zhang Q, et al., "30 Years of NF-κB: A Blossoming of Relevance to Human Pathobiology." Cell. 2017, 168(1-2)37-57.
Zhao FQ, "Octamer-binding transcription factors: genomics and functions." Published in final edited form as Front Biosci (Landmark Ed). 2013, 18:1051-71, author manuscript version, 33 pages.
Zheng et al., "Natural and induced CD4+CD25+ cells educate CD4+CD25− cells to develop suppressive activity: the role of IL-2, TGR-β, and IL-10." J Immunol. 2004, 172(9):5213-21.
Zhu H, et al., "AAV2/8-hSMAD3 gene delivery attenuates aortic atherogenesis, enhances Th2 response without fibrosis, in LDLR-KO mice on high cholesterol diet." J Transl Med. 2014, 12:252, doi: 10.1186/s12967-014-0252-8, 11 pages.
Zhu H, et al., "Comparison of efficacy of the disease-specific LOX1- and constitutive cytomegalovirus-promoters in expressing interleukin 10 through adeno-associated virus 2/8 delivery in atherosclerotic mice." PLoS One. 2014, 9(4): e94665, doi: 10.1371/journal.pone. 0094665, 7 pages.
Ziegler S, "FOXP3: of Mice and Men." Annu. Rev. Immunol. 2006, 24:209-26.
Zobel K, et al., "Interleukin 6, lipopolysaccharide-binding protein and interleukin 10 in the prediction of risk and etiologic patterns in patients with community-acquired pneumonia: results from the German competence network CAPNETZ." BMC Pulm Med. 2012, 12:6, doi: 10.1186/1471-2466-12-6, 10 pages.
Brignall et al., "Considering Abundance, Affinity, and Binding Site Availability in the NF-κB Target Selection Puzzle," Front Immunol. 10:609, pp. 1-14, doi: 10.3389/fimmu.2019.00609 (2019).
English title, abstract, figures, and figure legends for Wu et al., "Effect of NF-κB Binding Element Deletion on Transcription Regulation of NOX1," Chinese Journal of Pathophysiology, 30(10):1729-1734 (2014).

GenBank Accession LF425116, "Modified Polynucleotides for the Production of Proteins Associated with Human Disease," accessed Feb. 10, 2021, 2 printed pages.
GenBank Accession LF425118, "Modified Polynucleotides for the Production of Proteins Associated with Human Disease," accessed Feb. 10, 2021, 2 printed pages.
GenBank Accession LF425120, "Modified Polynucleotides for the Production of Proteins Associated with Human Disease," accessed Feb. 10, 2021, 2 printed pages.
GenBank Accession LF621166, "Modified Polynucleotides for the Production of Proteins Associated with Human Disease," accessed on Feb. 11, 2021, 2 printed pages.
GenBank Accession LX365446, "Modified Polynucleotides for the Production of Proteins Associated with Human Disease," accessed Feb. 10, 2021, 2 printed pages.
GenBank Accession LX365448, "Modified Polynucleotides for the Production of Proteins Associated with Human Disease," accessed Feb. 10, 2021, 2 printed pages.
GenBank Accession LX365450, "Modified Polynucleotides for the Production of Proteins Associated with Human Disease," accessed Feb. 10, 2021, 2 printed pages.
Invitation to Pay Additional Fees, PCT/US2020/056962, dated Jan. 25, 2021, 3 pages.
NCBI Blast for Seq 4, accessed Feb. 12, 2021, 18 pages.
Pankratova et al., "Oct-1 promoter region contains octamer sites and TAAT motifs recognized by Oct proteins", FEBS Letters 426 (1998) 81-85.
Sino Biological Inc., Anti-inflammatory cytokines list, accessed from sinobiological.com/resource/cytokines/all-anti-inflammatory-cytokines on Feb. 12, 2021, 10 pages.
Tantin et al., "The Octamer Binding Transcription Factor Oct-1 Is a Stress Sensor," Cancer Res. 65(23)10750-8 and Supplemental Tables 1-5 (2005).
Asadullah K, et al., "Interleukin-10 therapy—Review of a new approach." Pharmacol Rev. 2003 55(2):241-69.
Batchu RB, et al., "Cloning, expression, and purification of full length Rep78 of adeno-associated virus as a fusion protein with maltose binding protein in *Escherichia coli*." Biochem Biophys Res Commun. 1995, 208(2):714-20.
Brooks DG, et al., "IL-10 blockade facilitates DNA vaccine-induced T cell responses and enhances clearance of persistent virus infection." J Exp Med. 2008, 205(3):533-41.
Brooks DG, et al., "Interleukin-10 determines viral clearance or persistence in vivo." Nat Med. 2006, 12(11):1301-9.
Cao M, et al., "AAV2/8-humanFOXP3 gene therapy shows robust anti-atherosclerosis efficacy in LDLR-KO mice on high cholesterol diet." J Transl Med. 2015, 13:235, doi: 10.1186/s12967-015-0597-7, 8 pages.
Cao M, et al., "Dual AAV/IL-10 plus STAT3 anti-inflammatory gene delivery lowers atherosclerosis in LDLR KO Mice, but without increased benefit." Int J Vasc Med. 2012, 2012:524235, 10.1155/2012/524235, Epub 2011, 8 pages.
Cao M, et al., "The X gene of adeno-associated virus 2 (AAV2) is involved in viral DNA replication." PLoS One. 2014, 9(8):e104596, doi: 10.1371/journal.pone.0104596, 10 pages.
Cecchini S, et al., "Reproducible high yields of recombinant adeno-associated virus produced using invertebrate cells in 0.02- to 200-liter cultures." Hum Gene Ther. 2011, 22(8):1021-30.
Chen J, et al, "Lectin-like oxidized low-density lipoprotein receptor-1 (LOX-1) transcriptional regulation by Oct-1 in human endothelial cells: implications for atherosclerosis." Biochem. J. 2006, 393(Pt 1):255-65.
Chen J, et al., "Molecular dissection of angiotensin II-activated human LOX-1 promoter." Arterioscler Thromb Vasc Biol. 2006, 26(5):1163-8.
Chen J, et al., "SHP2 inhibitor PHPS1 protects against atherosclerosis by inhibiting smooth muscle cell proliferation." BMC Cardiovasc Disord. 2018, 18(1):72, doi: 10.1186/s12872-018-0816-2, 9 pages.
Clemons KV, et al., "Role of IL-10 in invasive aspergillosis: increased resistance of IL-10 gene knockout mice to lethal systemic aspergillosis." Clin Exp Immunol. 2000, 122(2):186-91.
Dandapat A, et al., "Over-expression of angiotensin II type 2 receptor (agtr2) decreases collagen accumulation in atherosclerotic

(56) References Cited

OTHER PUBLICATIONS plaque." Biochem Biophys Res Commun. 2008, 366(4):871-7. Epub 2007. doi:10.1016/j.bbrc.2007.11.061, article in press version, 7 pages.
Dandapat A, et al., "Overexpression of TGFbeta1 by adeno-associated virus type-2 vector protects myocardium from ischemia-reperfusion injury." Gene Ther. 2008, 15(6):415-23. Epub 2007.
Dela Paz NG, et al., "Regulation of NF-κB-dependent gene expression by the POU domain transcription factor Oct-1." J Biol Chem. 2007, 282(11):8424-34. Epub 2006.
Deng G, et al., "Foxp3 post-translational modifications and Treg suppressive activity." Front Immunol. 2019, 10:2486, doi: 10.3389/fimmu.2019.02486, 12 pages.
Ejrnaes M, et al., "Resolution of a chronic viral infection after interleukin-10 receptor blockade." J Exp Med. 2006, 203(11):2461-72.
Filippi CM and Von Herrath MG, "IL-10 and the resolution of infections." J Pathol. 2008, 214(2):224-30.
Fontenot JD, et al., "Foxp3 programs the development and function of CD4+CD25+ regulatory T cells." Nat Immunol. 2003, 4(4):330-6.
Ganguli A, et al., "Distinct NF-κB regulation by shear stress through Ras-dependent IκBα oscillations: real-time analysis of flow-mediated activation in live cells." Circ Res. 2005, 96(6):626-34.
Getz GS and Reardon CA, "Diet and murine atherosclerosis." Arterioscler Thromb Vasc Biol. 2006, 26(2):242-9. Epub 2005.
Gliozzi et al., "Modulation of Nitric Oxide Synthases by Oxidized LDLs: Rose in Vascular Inflammation and Atherosclerosis Development." Int J Mol Sci. 2019, 20(13):3294; doi:10.3390/ijms20133294, 16 pages.
Gregersen S, et al., "Inflammatory and oxidative stress responses to high-carbohydrate and high-fat meals in healthy humans." J Nutr Metab. 2012, 2012:238056, doi: 10.1155/2012/238056, 8 pages.
Grimm D, et al., "Novel tools for production and purification of recombinant adenoassociated virus vectors." Hum Gene Ther. 1998, 9(18):2745-60.
Hermonat PL and RB Batchu, "The adeno-associated virus Rep78 major regulatory protein forms multimeric complexes and the domain for this activity is contained within the carboxy-half of the molecule." FEBS Lett. 1997, 401(2-3):180-4.
Hermonat PL, et al., "Genetics of adeno-associated virus: isolation and preliminary characterization of adeno-associated virus type 2 mutants." J Virol. 1984, 51(2):329-39.
Hermonat PL, et al., "Multiple cellular proteins are recognized by the adeno-associated virus Rep78 major regulatory protein and the amino-half of Rep78 is required for many of these interactions." Biochem Mol Biol Int. 1997, 43(2):409-20.
Hermonat PL, et al., "The adeno-associated virus Rep78 major regulatory protein binds the cellular TATA-binding protein in vitro and in vivo." Virology. 1998, 245(1):120-7.
Hermonat PL, et al., "The adeno-associated virus Rep78 major regulatory/transformation suppressor protein binds cellular Sp1 in vitro and evidence of a biological effect." Cancer Res. 1996, 56(22):5299-304.
Hermonat PL, et al., "The packaging capacity of adeno-associated virus (AAV) and the potential for wild-type-plus AAV gene therapy vectors" FEBS Lett. 1997, 407(1):78-84.
Hermonat PL, et al., "Use of adeno-associated virus as a mammalian DNA cloning vector: transduction of neomycin resistance into mammalian tissue culture cells." Proc Natl Acad Sci USA. 1984, 81(20):6466-70.
Hermonat PL. "The first adeno-associated virus gene transfer experiment, 1983." Hum Gene Ther. 2014, 25(6):486-7.
Hori S, et al., "Control of regulatory T cell development by the transcription factor Foxp3." Science. 2003, 299(5609):1057-61.
Hsieh HJ, et al., "Shear-induced endothelial mechanotransduction: the interplay between reactive oxygen species (ROS) and nitric oxide (NO) and the pathophysiological implications." J Biomed Sci. 2014, 12:3 doi:10.1186/1423-0127-21-3, 15 pages.
Hu et al., "Over-expression of angiotensin II type 2 receptor (agtr2) reduces atherogenesis and modulates LOX-1, endothelial nitric oxide synthase and heme-oxygenase-1 expression." Atherosclerosis. 2007, doi: 10.1016/j.atherosclerosis.2007.11.006, in-press version, 7 pages.
Hwang J, et al. "Pulsatile versus oscillatory shear stress regulates NADPH oxidase subunit expression: implication for native LDL oxidation." Circ Res. 2003, 93(12):1225-32.
Jenuwein T and Grosschedl R, "Complex pattern of immunoglobulin μ gene expression in normal and transgenic mice: nonoverlapping regulatory sequences govern distinct tissue specificities." Genes Dev. 1991, 5(6):932-43.
Karagiannidis C, et al., "Glucocorticoids upregulate FOXP3 expression and regulatory T cells in asthma." J Allergy Clin Immunol. 2004, 114(6):1425-33.
Khan JA, et al., "AAV/hSTAT3-gene delivery lowers aortic inflammatory cell infiltration in LDLR KO mice on high cholesterol." Atherosclerosis. 2010, doi:10.1016/j.atherosclerosis.2010.07.029, in-press version, 8 pages.
Khan JA, et al., "Systemic human Netrin-1 gene delivery by adeno-associated virus type 8 alters leukocyte accumulation and atherogenesis in vivo" Gene Ther. 2011, 18(5):437-44, Epub 2010.
Khattri R, et al., "An essential role for Scurfin in CD4+CD25+ T regulatory cells." Nat Immunol. 2003, 4(4)337-42.
Kim J, et al., "Molecular networks of FOXP family: dual biologic functions, interplay with other molecules and clinical implications in cancer progression." Mol Cancer. 2019, 18(1):180, doi:10.1186/212943-019-1110-3, 19 pages.
Kitoh A, et al., "Indispensable role of the Runx1-Cbfbeta transcription complex for in vivo-suppressive function of FoxP3+ regulatory T cells." Immunity. 2009, 31(4):609-20.
Konopacki C, et al., "Transcription factor Foxp1 regulates Foxp3 chromatin binding and coordinates regulatory T cell function." Nat Immunol. 2019, 20(2)132-42.
Kunsch C, et al., "Selection of optimal kappa B/Rel DNA-binding motifs: interaction of both subunits of NF-kappa B with DNA is required for transcriptional activation." Mol Cell Biol. 1992, 12(10):4412-21.
Kuwano Y, et al., "Interferon-gamma activates transcription of NADPH oxidase 1 gene and upregulates production of superoxide anion by human large intestinal epithelial cells." Am J Physiol Cell Physiol. 2006 (Epub 2005), 290(2):C433-43.
Labow MA, et al., "Positive and negative autoregulation of the adeno-associated virus type 2 genome." J Virol. 1986, 60(1)251-8.
Laface D, et al., "Gene transfer into hematopoietic progenitor cells mediated by the adeno-associated virus vector." Virology. 1988, 162(2):483-6.
Li B, et al., "FOXP3 is a homo-oligomer and a component of a supramolecular regulatory complex disabled in the human XLAAD/IPEX autoimmune disease." Int Immunol. 2007, 19(7):825-35.
Li D, et al. "Suppression of atherogenesis by delivery of TGFbeta1ACT using adeno-associated virus type 2 in LDLR knockout mice." Biochem Biophys Res Commun. 2006, 344(3):701-7.
International Search Report and Written Opinion, PCT/US2020/056962, 14 pages, dated Apr. 1, 2021.
File History of U.S. Appl. No. 17/196,504, filed Mar. 9, 2021.

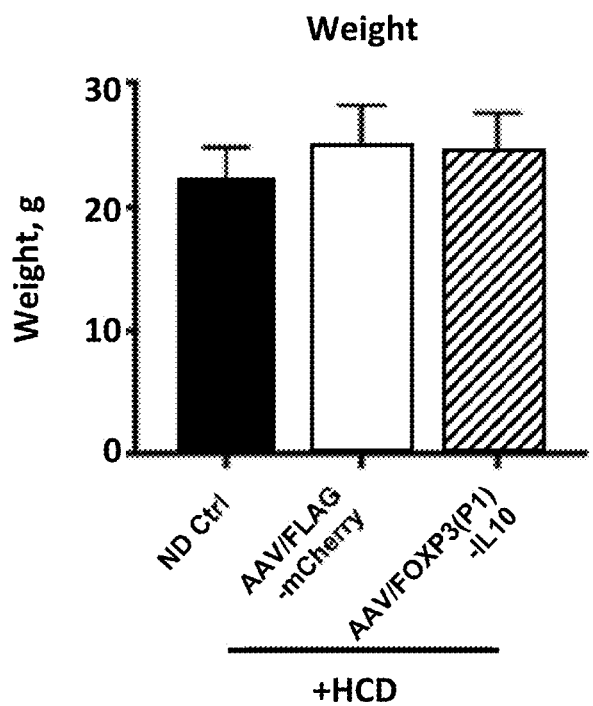
FIG. 10A
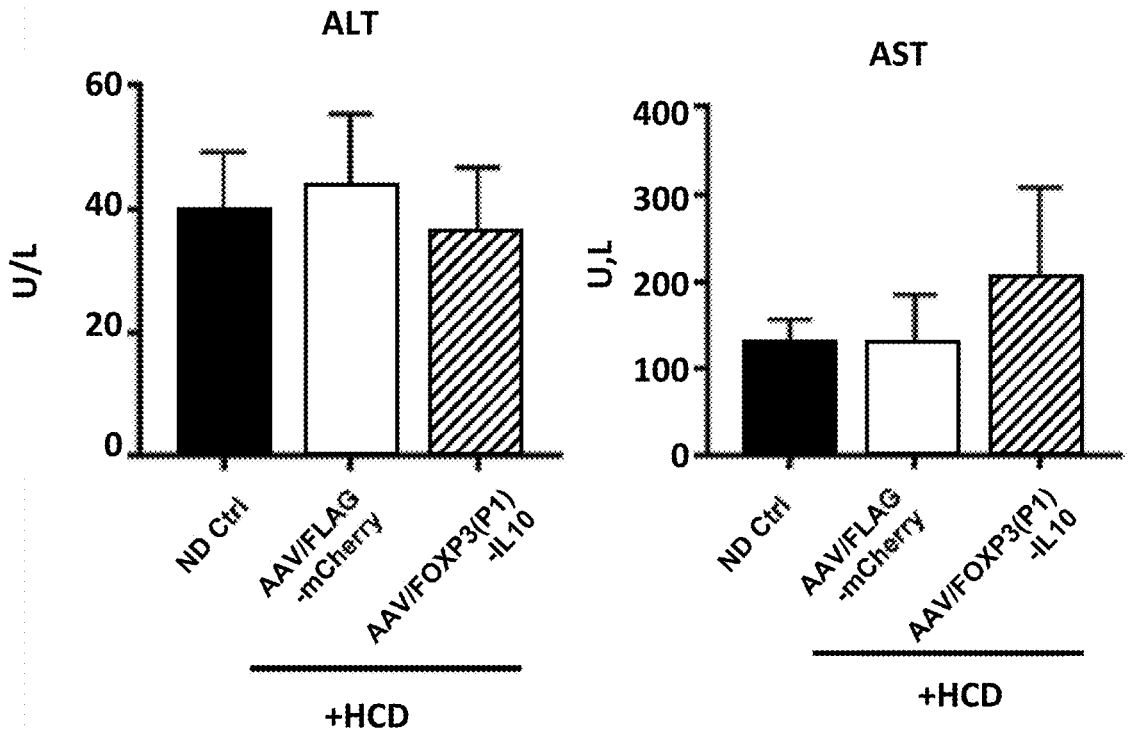
FIG. 10B
FIG. 10C

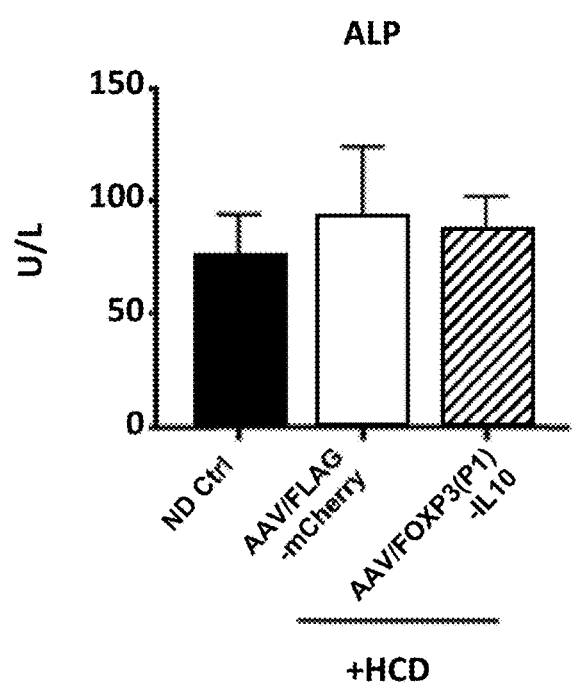
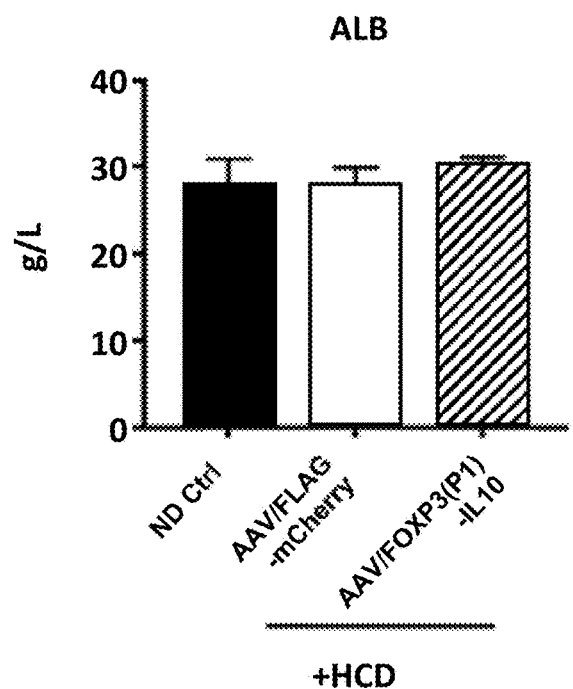
FIG. 10D  FIG. 10E

SEQUENCE LISTING

```
<160> NUMBER OF SEQ ID NOS: 42

<210> SEQ ID NO 1
<211> LENGTH: 2027
<212> TYPE: DNA
<213> ORGANISM: Homo sapiens
<220> FEATURE:
<221> NAME/KEY: misc_feature
<222> LOCATION: (1)..(2027)
<223> OTHER INFORMATION: 5' flanking sequence of human NOX1 gene

<400> SEQUENCE: 1
gttttccata tttaaaagta gtaaattgga taccatacat gaaaatcagc tccaggtgga      60
ttcaaaacat aaatgtaaaa tgcaaaaata taaaatttct agaagaaaat ataaaagagt     120
atcttgatat ctgggtagtg atggatttct aaaacaagac ataaaatgca taaatcataa     180
aagaaatgac tggtaatcag agtgcattaa aattaagaac ttccatttat cagaaaacac     240
tattaagaga ctgaaaagac aagccataaa cataagcaat aaaagattag tataagatta     300
taaacagaac cctaagaatc taaaagcaaa agaaaaacca atagaaagat agaccaaaaa     360
gtagaatagg ctcagaatag gctcttttaa aaagagaaaa ctcaaatggc cagcagttga     420
attaaaagat gctcaaactc attagtaatc agggaaatgc aaattaaaat cataatacga     480
tagttttcca cacttacttg aattataaaa acaaaaaagt ctggaaaata ccaagggttg     540
gtaagcatgt agaggaagta gaactctcat tcataactct ctgtagtata catttaggtg     600
gtcacttcgg aacgggtttg gaattacaca gcaaagtaga atatgtgcaa atctcaggac     660
cctggaattt tactcctggg tatataacctt agagaaactg tagcatatgt gtgacattcg     720
atcaacattg ttccatcatc atatccatca gtagtaggat gaatgaatac attaatgtat     780
attcattcat gcaatggcat attagatagc agtgtaagtg aaccgcaatt acatgtacat     840
gtatgaatct caaaaaccca atgttgaaag aagcaaacca cagaagcata catacacact     900
gccaggtttc atttacaaaa agttcaaaaa caggaaaaac taaacaatat attgcttagg     960
gatgcaatta tagttagtaa aaatataaag aaaaataaca gaatgattac cccaaatttc    1020
aggatagtga ttacatccgg tggggtagag gaggggaaga agatagatgt gatcagggag    1080
ggaaatacaa agagctttaa gatactggag aaaaatagtc tattttcttt aatctgagta    1140
gtgaacacat agatacttat tccttaaaat tattctttaa gttacatatg tatgttttat    1200
atactcttct gtgtatattt caccatttta gaaaagggaa aaaaaatcag tgcccagagc    1260
tgaacacaca actctagtaa atctatcata ctagaagaca atcatctcca ttcttttgag    1320
tgctctgcct ctgttttattt tgaaccaaag tgcacttttta tacttgttaa atttttctctt   1380 gctctatttg gcccttcttt tcacttgtcc ttccagccag tcaagttctc cccaaagcca    1440
tcatcatata tgtcaaccac agatcatcct ccaggggaac tggtatgcta aagtttctga    1500
gctagccagg ctgaaatcca aatggcagcc ggcagatgtg gcaacagttt gaaaagtgca    1560
ctttgaaaca gcttccttac cacacacgct tccctcccta cttctcctga agtaatctgt    1620
```

```
ttacagaccc agactaataa tctttttat gagaaacttt agcaaatctt ttatctagga      1680
aggcaatgct tcacattagg tcatgttgat aagatgatga gagagaatat tttcatccaa      1740
gaatgttgct atttcctgaa gcagtaaaat ccccacaggt aaaacccttg tggttctcat      1800
agatagggct ggtctatcta agctgatagc acagttctgt ccagagaagg aaggcagaat      1860
aaacttattc attcccagga actcttgggg taggtgtgtg ttttcacat cttaaaggct       1920 cacagaccct gcgctggaca aatgttccat tcctgaagga cctctccaga atccggattg      1980
ctgaatcttc cctgttgcct agaagggctc caaaccacct cttgaca                   2027

<210> SEQ ID NO 2
<211> LENGTH: 466
<212> TYPE: DNA
<213> ORGANISM: Homo sapiens
<220> FEATURE:
<221> NAME/KEY: misc_feature
<222> LOCATION: (1)..(466)
<223> OTHER INFORMATION: Exemplary human NOX1 core promoter

<400> SEQUENCE: 2
tttgaaacag cttccttacc acacacgctt ccctccctac ttctcctgaa gtaatctgtt       60
tacagaccca gactaataat ctttttatg agaaacttta gcaaatcttt tatctaggaa       120
ggcaatgctt cacattaggt catgttgata agatgatgag agagaatatt ttcatccaag      180
aatgttgcta tttcctgaag cagtaaaatc cccacaggta aaaccttgt ggttctcata       240 gatagggctg gtctatctaa gctgatagca cagttctgtc cagagaagga aggcagaata      300
aacttattca ttcccaggaa ctcttggggt aggtgtgtgt ttttcacatc ttaaaggctc      360
acagaccctg cgctggacaa atgttccatt cctgaaggac ctctccagaa tccggattgc      420
tgaatcttcc ctgttgccta agggctcc aaaccacctc ttgaca                      466

<210> SEQ ID NO 3
<211> LENGTH: 483
<212> TYPE: DNA
<213> ORGANISM: Homo sapiens
<220> FEATURE:
<221> NAME/KEY: misc_feature
<222> LOCATION: (1)..(483)
<223> OTHER INFORMATION: Exemplary variant human NOX1 core promoter

<400> SEQUENCE: 3
tttgaaacag cttccttacc acacacgctt ccctccctac ttctcctgaa gtaatctgtt       60
tacagaccca gactaataat ctttttatg agaaacttta gcaaatcttt tatctaggaa       120
ggccaatgct tcacattagg tcatgttgat aagatgatga gagagaatat tttcatccaa      180
gaatgttgct atttcctgaa gcagtaaaat ccccacaggt aaaacccttg tggttctcat      240
agatagggct ggtctatcta agctgatagc acagttctgt ccagagaagg aaggcagaat      300
aaacttattc attcccagga actcttgggg taggtgtgtg ttttcacat cttaaaggct       360 cacagaccct gcgctggaca aattgttcca ttcctgaagg acctctccag aatccggatt      420
gctgaatctt ccctgttgcc tagaagggct ccaaaccacc tcttgacatg aacgcgtgcc      480
acc                                                                   483

<210> SEQ ID NO 4
<211> LENGTH: 586
<212> TYPE: DNA
<213> ORGANISM: Artificial Sequence
<220> FEATURE:
```

```
<223> OTHER INFORMATION: Synthetic: Exemplary variant NOX1 core promoter
      with three NF-kB binding sequences and two Oct1 binding sequences
      at the 5' end, eNOX1 promoter

<400> SEQUENCE: 4
gaggagggga ttcccaagat cgaggagggg attcccaaga tcgaggaggg gattcccaag    60
atcaaaagta tgcaaatccc tgaaaagta tgcaaatccc tgatttgaaa cagcttcctt   120
accacacacg cttccctccc tacttctcct gaagtaatct gtttacagac ccagactaat   180 aatcttttt atgagaaact ttagcaaatc ttttatctag gaaggccaat gcttcacatt   240
aggtcatgtt gataagatga tgagagagaa tatttcatc caagaatgtt gctatttcct   300
gaagcagtaa aatccccaca ggtaaaaccc ttgtggttct catagatagg gctggtctat   360
ctaagctgat agcacagttc tgtccagaga aggaaggcag aataaactta ttcattccca   420
ggaactcttg gggtaggtgt gtgttttca catcttaaag gctcacagac cctgcgctgg   480
acaaattgtt ccattcctga aggacctctc cagaatccgg attgctgaat cttccctgtt   540
gcctagaagg gctccaaacc acctcttgac atgaacgcgt gccacc                586

<210> SEQ ID NO 5
<211> LENGTH: 10
<212> TYPE: DNA
<213> ORGANISM: Artificial Sequence
<220> FEATURE:
<223> OTHER INFORMATION: Synthetic: Exemplary consensus sequence of an
      NF-kB binding site
<220> FEATURE:
<221> NAME/KEY: misc_feature
<222> LOCATION: (4)..(4)
<223> OTHER INFORMATION: r is a purine
<220> FEATURE:
<221> NAME/KEY: misc_feature
<222> LOCATION: (5)..(5)
<223> OTHER INFORMATION: n is any nucleotide
<220> FEATURE:
<221> NAME/KEY: misc_feature
<222> LOCATION: (6)..(8)
<223> OTHER INFORMATION: y is a pyrimidine

<400> SEQUENCE: 5 gggrnyyycc                                                          10

<210> SEQ ID NO 6
<211> LENGTH: 10
<212> TYPE: DNA
<213> ORGANISM: Artificial Sequence
<220> FEATURE:
<223> OTHER INFORMATION: Synthetic: Exemplary consensus sequence of an
      NF-kB binding site
<220> FEATURE:
<221> NAME/KEY: misc_feature
<222> LOCATION: (3)..(4)
<223> OTHER INFORMATION: r is a purine
<220> FEATURE:
<221> NAME/KEY: misc_feature
<222> LOCATION: (5)..(6)
<223> OTHER INFORMATION: n is any nucleotide
<220> FEATURE:
<221> NAME/KEY: misc_feature
<222> LOCATION: (7)..(8)
<223> OTHER INFORMATION: y is a pyrimidine

<400> SEQUENCE: 6 ggrrnnyycc                                                          10

<210> SEQ ID NO 7
<211> LENGTH: 11
```

```
<212> TYPE: DNA
<213> ORGANISM: Artificial Sequence
<220> FEATURE:
<223> OTHER INFORMATION: Synthetic: Exemplary consensus sequence of an
      NF-kB binding site
<220> FEATURE:
<221> NAME/KEY: misc_feature
<222> LOCATION: (1)..(1)
<223> OTHER INFORMATION: r is a purine
<220> FEATURE:
<221> NAME/KEY: misc_feature
<222> LOCATION: (4)..(4)
<223> OTHER INFORMATION: r is as purine
<220> FEATURE:
<221> NAME/KEY: misc_feature
<222> LOCATION: (5)..(6)
<223> OTHER INFORMATION: n is any nucleotide
<220> FEATURE:
<221> NAME/KEY: misc_feature
<222> LOCATION: (7)..(8)
<223> OTHER INFORMATION: h is an adenine, a cytosine, or a thymine
<220> FEATURE:
<221> NAME/KEY: misc_feature
<222> LOCATION: (9)..(10)
<223> OTHER INFORMATION: y is a pyrimidine
<220> FEATURE:
<221> NAME/KEY: misc_feature
<222> LOCATION: (11)..(11)
<223> OTHER INFORMATION: b is a guanine, thymine, or cytosine

<400> SEQUENCE: 7
rggrnnhhyy b                                                          11

<210> SEQ ID NO 8
<211> LENGTH: 10
<212> TYPE: DNA
<213> ORGANISM: Artificial Sequence
<220> FEATURE:
<223> OTHER INFORMATION: Synthetic: Exemplary consensus sequence of an
      NF-kB binding site
<220> FEATURE:
<221> NAME/KEY: misc_feature
<222> LOCATION: (7)..(7)
<223> OTHER INFORMATION: y is a pyrimidine

<400> SEQUENCE: 8 ggggatyccc                                                            10

<210> SEQ ID NO 9
<211> LENGTH: 10
<212> TYPE: DNA
<213> ORGANISM: Artificial Sequence
<220> FEATURE:
<223> OTHER INFORMATION: Synthetic: Exemplary consensus sequence of an
      NF-kB binding site
<220> FEATURE:
<221> NAME/KEY: misc_feature
<222> LOCATION: (5)..(5)
<223> OTHER INFORMATION: n is any nucleotide

<400> SEQUENCE: 9 gggrntttcc                                                            10

<210> SEQ ID NO 10
<211> LENGTH: 10
<212> TYPE: DNA
<213> ORGANISM: Artificial Sequence
<220> FEATURE:
<223> OTHER INFORMATION: Synthetic: Exemplary consensus sequence of an
      NF-kB binding site
<220> FEATURE:
<221> NAME/KEY: misc_feature
<222> LOCATION: (1)..(1)
```

```
<223> OTHER INFORMATION: n is any nucleotide
<220> FEATURE:
<221> NAME/KEY: misc_feature
<222> LOCATION: (4)..(5)
<223> OTHER INFORMATION: n is any nucleotide
<220> FEATURE:
<221> NAME/KEY: misc_feature
<222> LOCATION: (6)..(6)
<223> OTHER INFORMATION: w is an adenine or a thymine

<400> SEQUENCE: 10 nggnnwttcc                                                                  10

<210> SEQ ID NO 11
<211> LENGTH: 10
<212> TYPE: DNA
<213> ORGANISM: Artificial Sequence
<220> FEATURE:
<223> OTHER INFORMATION: Synthetic: Exemplary consensus sequence of an
      NF-kB binding site
<220> FEATURE:
<221> NAME/KEY: misc_feature
<222> LOCATION: (4)..(4)
<223> OTHER INFORMATION: r is a purine
<220> FEATURE:
<221> NAME/KEY: misc_feature
<222> LOCATION: (5)..(6)
<223> OTHER INFORMATION: n is any nucleotide
<220> FEATURE:
<221> NAME/KEY: misc_feature
<222> LOCATION: (7)..(8)
<223> OTHER INFORMATION: y is a pyrimidine

<400> SEQUENCE: 11 gggrnnyycc                                                                  10

<210> SEQ ID NO 12
<211> LENGTH: 11
<212> TYPE: DNA
<213> ORGANISM: Artificial Sequence
<220> FEATURE:
<223> OTHER INFORMATION: Synthetic: Exemplary sequence of an NF-kB
      binding site

<400> SEQUENCE: 12
ggggaatccc c                                                                11

<210> SEQ ID NO 13
<211> LENGTH: 11
<212> TYPE: DNA
<213> ORGANISM: Artificial Sequence
<220> FEATURE:
<223> OTHER INFORMATION: Synthetic: Exemplary sequence of an NF-kB
      binding site

<400> SEQUENCE: 13
ggggactttc c                                                                11

<210> SEQ ID NO 14
<211> LENGTH: 11
<212> TYPE: DNA
<213> ORGANISM: Artificial Sequence
<220> FEATURE:
<223> OTHER INFORMATION: Synthetic: Exemplary sequence of an NF-kB
      binding site

<400> SEQUENCE: 14 aggggggatct g                                                               11
```

```
<210> SEQ ID NO 15
<211> LENGTH: 10
<212> TYPE: DNA
<213> ORGANISM: Artificial Sequence
<220> FEATURE:
<223> OTHER INFORMATION: Synthetic: Exemplary sequence of an NF-kB
      binding site

<400> SEQUENCE: 15
agggaagtta                                                              10

<210> SEQ ID NO 16
<211> LENGTH: 11
<212> TYPE: DNA
<213> ORGANISM: Artificial Sequence
<220> FEATURE:
<223> OTHER INFORMATION: Synthetic: Exemplary sequence of an NF-kB
      binding site

<400> SEQUENCE: 16
ctggggattt a                                                            11

<210> SEQ ID NO 17
<211> LENGTH: 10
<212> TYPE: DNA
<213> ORGANISM: Artificial Sequence
<220> FEATURE:
<223> OTHER INFORMATION: Synthetic: Exemplary sequence of an NF-kB
      binding site

<400> SEQUENCE: 17
gggaattccc                                                              10

<210> SEQ ID NO 18
<211> LENGTH: 10
<212> TYPE: DNA
<213> ORGANISM: Artificial Sequence
<220> FEATURE:
<223> OTHER INFORMATION: Synthetic: Exemplary sequence of  an NF-kB
      binding site

<400> SEQUENCE: 18
gggaatttcc                                                              10

<210> SEQ ID NO 19
<211> LENGTH: 10
<212> TYPE: DNA
<213> ORGANISM: Artificial Sequence
<220> FEATURE:
<223> OTHER INFORMATION: Synthetic: Exemplary sequence of an NF-kB
      binding site

<400> SEQUENCE: 19
ggggattccc                                                              10

<210> SEQ ID NO 20
<211> LENGTH: 21
<212> TYPE: DNA
<213> ORGANISM: Artificial Sequence
<220> FEATURE:
<223> OTHER INFORMATION: Synthetic: Exemplary sequence of an NF-kB
      binding site

<400> SEQUENCE: 20
gaggagggga ttcccaagat c                                                 21

<210> SEQ ID NO 21
```

```
<211> LENGTH: 8
<212> TYPE: DNA
<213> ORGANISM: Artificial Sequence
<220> FEATURE:
<223> OTHER INFORMATION: Synthetic: Exemplary sequence of an Oct1
      binding site

<400> SEQUENCE: 21 atgcaaat                                                                    8

<210> SEQ ID NO 22
<211> LENGTH: 1433
<212> TYPE: DNA
<213> ORGANISM: Artificial Sequence
<220> FEATURE:
<223> OTHER INFORMATION: Synthetic: eNOXpr-3xFLAG-mCherry

<400> SEQUENCE: 22
gaggagggga ttcccaagat cgaggagggg attcccaaga tcgaggaggg gattcccaag     60
atcaaaagta tgcaaatccc tgaaaaagta tgcaaatccc tgatttgaaa cagcttcctt    120
accacacacg cttccctccc tacttctcct gaagtaatct gtttacagac ccagactaat    180
aatctttttt atgagaaact ttagcaaatc ttttatctag aaggccaat  gcttcacatt    240 aggtcatgtt gataagatga tgagagagaa tattttcatc caagaatgtt gctatttcct    300
gaagcagtaa atccccaca  ggtaaaaccc ttgtggttct catagatagg gctggtctat    360
ctaagctgat agcacagttc tgtccagaga aggaaggcag aataaactta ttcattccca    420
ggaactcttg gggtaggtgt gtgttttca  catcttaaag gctcacagac cctgcgctgg    480
acaaattgtt ccattcctga aggacctctc cagaatccgg attgctgaat cttccctgtt    540
gcctagaagg gctccaaacc acctcttgac atgaacgcgt gccaccatgt ctgactataa    600
agaccatgat ggggactaca agaccatga  tatagattac aaagacgatg atgacaaaat    660
ggttagcaag ggggaggaag acaatatggc cataattaaa gaattcatgc gcttcaaagt    720
tcacatggaa ggaagcgtga acggacatga gttcgagata aaggcgagg  gcgaggggcg    780 gccctatgag ggaacgcaga ctgctaaact gaaggttact aaaggtggcc ctcttccttt    840
cgcatgggac atcctgtctc cgcagttcat gtatggatcc aaggcatatg ttaagcatcc    900
ggctgatata ccagattacc tcaaattgag cttcctgaa  gggtttaagt gggaaagggt    960
catgaacttt gaagacggtg gagttgtgac agttacacag gattcatcac ttcaggacgg   1020
tgagtttata tacaaggtta aacttagggg aactaattt  ccttccgacg gccccgtcat   1080
gcagaaaaaa accatggggt ggga ggcgag ctccgagcgg atgtacccag aggatggagc   1140
actgaagggc gaaataaaac agcgactgaa attgaaagac ggaggtcact atgatgcaga   1200
agttaagacg acatacaagg ccaaaaagcc agttcagttg ccgggtgcat ataacgtcaa   1260
tatcaagctg acattacat  cccacaatga ggattatacg atagtggagc agtatgagcg   1320
ggcagaaggg cggcactcca caggaggaat ggacgaactc tataaatgac ccaccagcct   1380
tgtcctaata aaattaagtt gcatcatttt gtttgactac tcgagcccct gca          1433

<210> SEQ ID NO 23
<211> LENGTH: 260
<212> TYPE: PRT
<213> ORGANISM: Artificial Sequence
<220> FEATURE:
<223> OTHER INFORMATION: Synthetic: 3xFLAG-mCherry amino acid sequence

<400> SEQUENCE: 23
```

```
Met Ser Asp Tyr Lys Asp His Asp Gly Asp Tyr Lys Asp His Asp Ile
1               5                   10                  15

Asp Tyr Lys Asp Asp Asp Lys Met Val Ser Lys Gly Glu Glu Asp
            20                  25                  30

Asn Met Ala Ile Ile Lys Glu Phe Met Arg Phe Lys Val His Met Glu
        35                  40                  45

Gly Ser Val Asn Gly His Glu Phe Glu Ile Glu Gly Glu Gly Glu Gly
    50                  55                  60

Arg Pro Tyr Glu Gly Thr Gln Thr Ala Lys Leu Lys Val Thr Lys Gly
65                  70                  75                  80

Gly Pro Leu Pro Phe Ala Trp Asp Ile Leu Ser Pro Gln Phe Met Tyr
                85                  90                  95

Gly Ser Lys Ala Tyr Val Lys His Pro Ala Asp Ile Pro Asp Tyr Leu
            100                 105                 110

Lys Leu Ser Phe Pro Glu Gly Phe Lys Trp Glu Arg Val Met Asn Phe
        115                 120                 125

Glu Asp Gly Gly Val Val Thr Val Thr Gln Asp Ser Ser Leu Gln Asp
    130                 135                 140

Gly Glu Phe Ile Tyr Lys Val Lys Leu Arg Gly Thr Asn Phe Pro Ser
145                 150                 155                 160

Asp Gly Pro Val Met Gln Lys Lys Thr Met Gly Trp Glu Ala Ser Ser
                165                 170                 175

Glu Arg Met Tyr Pro Glu Asp Gly Ala Leu Lys Gly Glu Ile Lys Gln
            180                 185                 190

Arg Leu Lys Leu Lys Asp Gly Gly His Tyr Asp Ala Glu Val Lys Thr
        195                 200                 205

Thr Tyr Lys Ala Lys Lys Pro Val Gln Leu Pro Gly Ala Tyr Asn Val
    210                 215                 220

Asn Ile Lys Leu Asp Ile Thr Ser His Asn Glu Asp Tyr Thr Ile Val
225                 230                 235                 240

Glu Gln Tyr Glu Arg Ala Glu Gly Arg His Ser Thr Gly Gly Met Asp
                245                 250                 255

Glu Leu Tyr Lys
            260

<210> SEQ ID NO 24
<211> LENGTH: 431
<212> TYPE: PRT
<213> ORGANISM: Homo sapiens
<220> FEATURE:
<221> NAME/KEY: misc_feature
<222> LOCATION: (1)..(431)
<223> OTHER INFORMATION: Exemplary wildtype human FoxP3 amino acid
      sequence

<400> SEQUENCE: 24

Met Pro Asn Pro Arg Pro Gly Lys Pro Ser Ala Pro Ser Leu Ala Leu
1               5                   10                  15

Gly Pro Ser Pro Gly Ala Ser Pro Ser Trp Arg Ala Ala Pro Lys Ala
            20                  25                  30

Ser Asp Leu Leu Gly Ala Arg Gly Pro Gly Gly Thr Phe Gln Gly Arg
        35                  40                  45

Asp Leu Arg Gly Gly Ala His Ala Ser Ser Ser Leu Asn Pro Met
    50                  55                  60

Pro Pro Ser Gln Leu Gln Leu Pro Thr Leu Pro Leu Val Met Val Ala
65                  70                  75                  80
```

```
Pro Ser Gly Ala Arg Leu Gly Pro Leu Pro His Leu Gln Ala Leu Leu
                85                  90                  95

Gln Asp Arg Pro His Phe Met His Gln Leu Ser Thr Val Asp Ala His
            100                 105                 110

Ala Arg Thr Pro Val Leu Gln Val His Pro Leu Glu Ser Pro Ala Met
        115                 120                 125

Ile Ser Leu Thr Pro Pro Thr Thr Ala Thr Gly Val Phe Ser Leu Lys
130                 135                 140

Ala Arg Pro Gly Leu Pro Pro Gly Ile Asn Val Ala Ser Leu Glu Trp
145                 150                 155                 160

Val Ser Arg Glu Pro Ala Leu Leu Cys Thr Phe Pro Asn Pro Ser Ala
                165                 170                 175

Pro Arg Lys Asp Ser Thr Leu Ser Ala Val Pro Gln Ser Ser Tyr Pro
            180                 185                 190

Leu Leu Ala Asn Gly Val Cys Lys Trp Pro Gly Cys Glu Lys Val Phe
        195                 200                 205

Glu Glu Pro Glu Asp Phe Leu Lys His Cys Gln Ala Asp His Leu Leu
210                 215                 220

Asp Glu Lys Gly Arg Ala Gln Cys Leu Leu Gln Arg Glu Met Val Gln
225                 230                 235                 240

Ser Leu Glu Gln Gln Leu Val Leu Glu Lys Glu Lys Leu Ser Ala Met
                245                 250                 255

Gln Ala His Leu Ala Gly Lys Met Ala Leu Thr Lys Ala Ser Ser Val
            260                 265                 270

Ala Ser Ser Asp Lys Gly Ser Cys Cys Ile Val Ala Ala Gly Ser Gln
        275                 280                 285

Gly Pro Val Val Pro Ala Trp Ser Gly Pro Arg Glu Ala Pro Asp Ser
290                 295                 300

Leu Phe Ala Val Arg Arg His Leu Trp Gly Ser His Gly Asn Ser Thr
305                 310                 315                 320

Phe Pro Glu Phe Leu His Asn Met Asp Tyr Phe Lys Phe His Asn Met
                325                 330                 335

Arg Pro Pro Phe Thr Tyr Ala Thr Leu Ile Arg Trp Ala Ile Leu Glu
            340                 345                 350

Ala Pro Glu Lys Gln Arg Thr Leu Asn Glu Ile Tyr His Trp Phe Thr
        355                 360                 365

Arg Met Phe Ala Phe Phe Arg Asn His Pro Ala Thr Trp Lys Asn Ala
370                 375                 380

Ile Arg His Asn Leu Ser Leu His Lys Cys Phe Val Arg Val Glu Ser
385                 390                 395                 400

Glu Lys Gly Ala Val Trp Thr Val Asp Glu Leu Glu Phe Arg Lys Lys
                405                 410                 415

Arg Ser Gln Arg Pro Ser Arg Cys Ser Asn Pro Thr Pro Gly Pro
            420                 425                 430
```

<210> SEQ ID NO 25
<211> LENGTH: 38
<212> TYPE: PRT
<213> ORGANISM: Homo sapiens
<220> FEATURE:
<221> NAME/KEY: misc_feature
<222> LOCATION: (1)..(38)
<223> OTHER INFORMATION: Exemplary human FOXP3 zinc finger and leucine zipper region

<400> SEQUENCE: 25

```
Glu Lys Gly Arg Ala Gln Cys Leu Leu Gln Arg Glu Met Val Gln Ser
1               5                   10                  15

Leu Glu Gln Gln Leu Val Leu Glu Lys Glu Lys Leu Ser Ala Met Gln
            20                  25                  30

Ala His Leu Ala Gly Lys
            35
```

<210> SEQ ID NO 26
<211> LENGTH: 489
<212> TYPE: PRT
<213> ORGANISM: Homo sapiens
<220> FEATURE:
<221> NAME/KEY: misc_feature
<222> LOCATION: (1)..(489)
<223> OTHER INFORMATION: Exemplary wildtype human FoxP1 sequence

<400> SEQUENCE: 26

```
Met Met Thr Pro Gln Val Ile Thr Pro Gln Gln Met Gln Gln Ile Leu
1               5                   10                  15

Gln Gln Gln Val Leu Ser Pro Gln Leu Gln Val Leu Leu Gln Gln
            20                  25                  30

Gln Gln Ala Leu Met Leu Gln Gln Leu Trp Lys Glu Val Thr
        35                  40                  45

Ser Ala His Thr Ala Glu Glu Thr Thr Gly Asn Asn His Ser Ser Leu
    50                  55                  60

Asp Leu Thr Thr Thr Cys Val Ser Ser Ala Pro Ser Lys Thr Ser
65              70                  75                  80

Leu Ile Met Asn Pro His Ala Ser Thr Asn Gly Gln Leu Ser Val His
                85                  90                  95

Thr Pro Lys Arg Glu Ser Leu Ser His Glu Glu His Pro His Ser His
            100                 105                 110

Pro Leu Tyr Gly His Gly Val Cys Lys Trp Pro Gly Cys Glu Ala Val
            115                 120                 125

Cys Glu Asp Phe Gln Ser Phe Leu Lys His Leu Asn Ser Glu His Ala
    130                 135                 140

Leu Asp Asp Arg Ser Thr Ala Gln Cys Arg Val Gln Met Gln Val Val
145                 150                 155                 160

Gln Gln Leu Glu Leu Gln Leu Ala Lys Asp Lys Glu Arg Leu Gln Ala
                165                 170                 175

Met Met Thr His Leu His Val Lys Ser Thr Glu Pro Lys Ala Ala Pro
            180                 185                 190

Gln Pro Leu Asn Leu Val Ser Ser Val Thr Leu Ser Lys Ser Ala Ser
            195                 200                 205

Glu Ala Ser Pro Gln Ser Leu Pro His Thr Pro Thr Thr Pro Thr Ala
        210                 215                 220

Pro Leu Thr Pro Val Thr Gln Gly Pro Ser Val Ile Thr Thr Thr Ser
225                 230                 235                 240

Met His Thr Val Gly Pro Ile Arg Arg Arg Tyr Ser Asp Lys Tyr Asn
                245                 250                 255

Val Pro Ile Ser Ser Ala Asp Ile Ala Gln Asn Gln Glu Phe Tyr Lys
            260                 265                 270

Asn Ala Glu Val Arg Pro Pro Phe Thr Tyr Ala Ser Leu Ile Arg Gln
        275                 280                 285

Ala Ile Leu Glu Ser Pro Glu Lys Gln Leu Thr Leu Asn Glu Ile Tyr
    290                 295                 300

Asn Trp Phe Thr Arg Met Phe Ala Tyr Phe Arg Arg Asn Ala Ala Thr
```

```
                305                 310                 315                 320
        Trp Lys Asn Ala Val Arg His Asn Leu Ser Leu His Lys Cys Phe Val
                        325                 330                 335

Arg Val Glu Asn Val Lys Gly Ala Val Trp Thr Val Asp Glu Val Glu
                        340                 345                 350

Phe Gln Lys Arg Arg Pro Gln Lys Ile Ser Gly Asn Pro Ser Leu Ile
                        355                 360                 365

Lys Asn Met Gln Ser Ser His Ala Tyr Cys Thr Pro Leu Asn Ala Ala
                370                 375                 380

Leu Gln Ala Ser Met Ala Glu Asn Ser Ile Pro Leu Tyr Thr Thr Ala
        385                 390                 395                 400

Ser Met Gly Asn Pro Thr Leu Gly Asn Leu Ala Ser Ala Ile Arg Glu
                        405                 410                 415

Glu Leu Asn Gly Ala Met Glu His Thr Asn Ser Asn Glu Ser Asp Ser
                        420                 425                 430

Ser Pro Gly Arg Ser Pro Met Gln Ala Val His Pro Val His Val Lys
                        435                 440                 445

Glu Glu Pro Leu Asp Pro Glu Glu Ala Glu Gly Pro Leu Ser Leu Val
                450                 455                 460

Thr Thr Ala Asn His Ser Pro Asp Phe Asp His Asp Arg Asp Tyr Glu
        465                 470                 475                 480

Asp Glu Pro Val Asn Glu Asp Met Glu
                        485

<210> SEQ ID NO 27
<211> LENGTH: 38
<212> TYPE: PRT
<213> ORGANISM: Homo sapiens
<220> FEATURE:
<221> NAME/KEY: misc_feature
<222> LOCATION: (1)..(38)
<223> OTHER INFORMATION: Exemplary human FOXP1 zinc finger and leucine
      zipper region

<400> SEQUENCE: 27

Asp Arg Ser Thr Ala Gln Cys Arg Val Gln Met Gln Val Val Gln Gln
1               5                   10                  15

Leu Glu Leu Gln Leu Ala Lys Asp Lys Glu Arg Leu Gln Ala Met Met
            20                  25                  30

Thr His Leu His Val Lys
        35

<210> SEQ ID NO 28
<211> LENGTH: 431
<212> TYPE: PRT
<213> ORGANISM: Artificial Sequence
<220> FEATURE:
<223> OTHER INFORMATION: Synthetic: Exemplary FOXP3(P1) amino acid
      sequence FOXP1 zinc finger and leucine zipper region underlined

<400> SEQUENCE: 28

Met Pro Asn Pro Arg Pro Gly Lys Pro Ser Ala Pro Ser Leu Ala Leu
1               5                   10                  15

Gly Pro Ser Pro Gly Ala Ser Pro Ser Trp Arg Ala Ala Pro Lys Ala
            20                  25                  30

Ser Asp Leu Leu Gly Ala Arg Gly Pro Gly Gly Thr Phe Gln Gly Arg
        35                  40                  45

Asp Leu Arg Gly Gly Ala His Ala Ser Ser Ser Ser Leu Asn Pro Met
    50                  55                  60
```

Pro Pro Ser Gln Leu Gln Leu Pro Thr Leu Pro Leu Val Met Val Ala
65                  70                  75                  80

Pro Ser Gly Ala Arg Leu Gly Pro Leu Pro His Leu Gln Ala Leu Leu
                85                  90                  95

Gln Asp Arg Pro His Phe Met His Gln Leu Ser Thr Val Asp Ala His
            100                 105                 110

Ala Arg Thr Pro Val Leu Gln Val His Pro Leu Glu Ser Pro Ala Met
        115                 120                 125

Ile Ser Leu Thr Pro Pro Thr Thr Ala Thr Gly Val Phe Ser Leu Lys
130                 135                 140

Ala Arg Pro Gly Leu Pro Pro Gly Ile Asn Val Ala Ser Leu Glu Trp
145                 150                 155                 160

Val Ser Arg Glu Pro Ala Leu Leu Cys Thr Phe Pro Asn Pro Ser Ala
                165                 170                 175

Pro Arg Lys Asp Ser Thr Leu Ser Ala Val Pro Gln Ser Ser Tyr Pro
            180                 185                 190

Leu Leu Ala Asn Gly Val Cys Lys Trp Pro Gly Cys Glu Lys Val Phe
        195                 200                 205

Glu Glu Pro Glu Asp Phe Leu Lys His Cys Gln Ala Asp His Leu Leu
210                 215                 220

Asp Asp Arg Ser Thr Ala Gln Cys Arg Val Gln Met Gln Val Val Gln
225                 230                 235                 240

Gln Leu Glu Leu Gln Leu Ala Lys Asp Lys Glu Arg Leu Gln Ala Met
                245                 250                 255

Met Thr His Leu His Val Lys Met Ala Leu Thr Lys Ala Ser Ser Val
            260                 265                 270

Ala Ser Ser Asp Lys Gly Ser Cys Cys Ile Val Ala Ala Gly Ser Gln
        275                 280                 285

Gly Pro Val Val Pro Ala Trp Ser Gly Pro Arg Glu Ala Pro Asp Ser
290                 295                 300

Leu Phe Ala Val Arg Arg His Leu Trp Gly Ser His Gly Asn Ser Thr
305                 310                 315                 320

Phe Pro Glu Phe Leu His Asn Met Asp Tyr Phe Lys Phe His Asn Met
                325                 330                 335

Arg Pro Pro Phe Thr Tyr Ala Thr Leu Ile Arg Trp Ala Ile Leu Glu
            340                 345                 350

Ala Pro Glu Lys Gln Arg Thr Leu Asn Glu Ile Tyr His Trp Phe Thr
        355                 360                 365

Arg Met Phe Ala Phe Phe Arg Asn His Pro Ala Thr Trp Lys Asn Ala
370                 375                 380

Ile Arg His Asn Leu Ser Leu His Lys Cys Phe Val Arg Val Glu Ser
385                 390                 395                 400

Glu Lys Gly Ala Val Trp Thr Val Asp Glu Leu Glu Phe Arg Lys Lys
                405                 410                 415

Arg Ser Gln Arg Pro Ser Arg Cys Ser Asn Pro Thr Pro Gly Pro
            420                 425                 430

<210> SEQ ID NO 29
<211> LENGTH: 1296
<212> TYPE: DNA
<213> ORGANISM: Artificial Sequence
<220> FEATURE:
<223> OTHER INFORMATION: Synthetic: Exemplary FoxP3(P1) nucleotide
      sequence FoxP1 zinc finger and leucine zipper region underlined

<400> SEQUENCE: 29

```
atgccgaatc cccggccagg caagcccagt gccccgtcac ttgcccttgg gcctagtcct    60
ggggcttcac catcctggcg agctgcacct aaggcatctg acctcttggg ggcacgagga   120
ccgggcggga cgtttcaggg aagggacctt agaggcggag ctcatgcaag ctcttcttca   180
ctgaacccga tgccgccgag tcagttgcaa ctccccacac tcccactcgt aatggtggcg   240
ccctctggcg caagactcgg acctctccca cacctgcaag ccctcttgca ggacagacca   300
cacttcatgc accaactttc aacggttgac gcacacgcac ggacaccagt gctgcaagtt   360
catccacttg aatccctgc catgatcagc ctgacaccgc ctactaccgc gacaggtgtc    420
ttttctttga agcgaggcc tggattgcca cctggcatca atgtggcgtc cctggagtgg    480
gtttcccgcg aacctgctct cctgtgcaca tttccaaacc cgagtgcgcc gcgaaaagat   540
agtacgttgt ccgcagtacc tcagagctca tatccacttt tggcaaacgg tgtgtgtaaa   600
tggcctggat gcgaaaaagt attcgaagag ccggaggact ttttgaaaca ttgccaagct   660
gaccacctgc tcgatgatcg gtcaaccgcg caatgcaggg tgcaaatgca agttgtacaa   720
cagctcgaat gcagttggc gaaggacaag gagaggctgc aagcaatgat gacccatctt   780
catgttaaaa tggccctgac caaggcaagc tctgttgcaa gctccgacaa aggctcttgc   840
tgtatcgtag cggcgggatc tcaaggaccg gtcgtcccag cgtggagtgg ccctcgggaa   900
gccctgata gtcttttcgc cgtgagacgc cacctgtggg gcagccatgg aaactccact   960
tttcctgaat ttttgcacaa tatggactac tttaagttcc ataacatgcg ccccccgttt  1020
acatacgcga cgctcatccg gtgggcaatc ttggaagcgc ctgaaaaaca acgaaccttg  1080
aacgagatat atcattggtt cacgcgaatg ttcgctttct tcagaaatca cccggctact  1140
tggaagaatg ccataagaca caatctttct ctccataaat gctttgtaag ggtcgagtcc  1200
gaaaaggggg cagtatggac tgttgacgag ctggagtttc ggaaaaagcg gtcacaacgc  1260
ccgtcaagat gctcaaaccc taccccaggc ccttga                            1296
```

<210> SEQ ID NO 30
<211> LENGTH: 124
<212> TYPE: DNA
<213> ORGANISM: Artificial Sequence
<220> FEATURE:
<223> OTHER INFORMATION: Synthetic: Exemplary mini-promoter TATA box nucleotide sequence

<400> SEQUENCE: 30

```
ttagataaag gctgtctccg cgcctatata aaactcttgt ttttctttt tctctatcag    60
ttcatttgta gcatcttaat ttactatcct tctactatca gttgccgccg ccgtcgacgc   120
cacc                                                                124
```

<210> SEQ ID NO 31
<211> LENGTH: 178
<212> TYPE: PRT
<213> ORGANISM: Homo sapiens
<220> FEATURE:
<221> NAME/KEY: misc_feature
<222> LOCATION: (1)..(178)
<223> OTHER INFORMATION: Exemplary human IL10 amino acid sequence

<400> SEQUENCE: 31

```
Met His Ser Ser Ala Leu Leu Cys Cys Leu Val Leu Leu Thr Gly Val
1               5                   10                  15

Arg Ala Ser Pro Gly Gln Gly Thr Gln Ser Glu Asn Ser Cys Thr His
```

```
                  20                  25                  30

Phe Pro Gly Asn Leu Pro Asn Met Leu Arg Asp Leu Arg Asp Ala Phe
             35                  40                  45

Ser Arg Val Lys Thr Phe Phe Gln Met Lys Asp Gln Leu Asp Asn Leu
 50                  55                  60

Leu Leu Lys Glu Ser Leu Leu Glu Asp Phe Lys Gly Tyr Leu Gly Cys
 65                  70                  75                  80

Gln Ala Leu Ser Glu Met Ile Gln Phe Tyr Leu Glu Glu Val Met Pro
                 85                  90                  95

Gln Ala Glu Asn Gln Asp Pro Asp Ile Lys Ala His Val Asn Ser Leu
            100                 105                 110

Gly Glu Asn Leu Lys Thr Leu Arg Leu Arg Leu Arg Arg Cys His Arg
            115                 120                 125

Phe Leu Pro Cys Glu Asn Lys Ser Lys Ala Val Glu Gln Val Lys Asn
            130                 135                 140

Ala Phe Asn Lys Leu Gln Glu Lys Gly Ile Tyr Lys Ala Met Ser Glu
145                 150                 155                 160

Phe Asp Ile Phe Ile Asn Tyr Ile Glu Ala Tyr Met Thr Met Lys Ile
                165                 170                 175

Arg Asn

<210> SEQ ID NO 32
<211> LENGTH: 537
<212> TYPE: DNA
<213> ORGANISM: Homo sapiens
<220> FEATURE:
<221> NAME/KEY: misc_feature
<222> LOCATION: (1)..(537)
<223> OTHER INFORMATION: Exemplary human IL10 nucleotide sequence

<400> SEQUENCE: 32
atgcactctt ctgcacttct gtgctgcctc gtgctcctga caggtgtcag ggcgagtccc       60 ggtcaggggta cgcaatctga aaactcctgc acccactttc ggggaatttt gcccaacatg      120
ctgagggatc tgagagacgc tttcagccgc gttaagacat tcttccagat gaaagatcag      180
ctcgataatc ttctgttgaa agagtcactg cttgaggatt ttaaagggta tttggggtgc      240
caggctctgt cagaaatgat acagttctat ctcgaagagg tgatgcctca agcggagaac      300
caagatccag acataaaggc tcacgttaat tccttgggcg agaatctgaa acccctgagg      360
cttaggctga cgctgtgtca tcgcttcttg ccctgtgaaa acaaatccaa agcggtagag      420
caggtcaaaa atgcctttaa taagctgcaa gagaagggga tatataaggc aatgtctgag      480
tttgatatct ttataaacta tatagaagct tacatgacaa tgaaaattcg aattag          537

<210> SEQ ID NO 33
<211> LENGTH: 94
<212> TYPE: DNA
<213> ORGANISM: Artificial Sequence
<220> FEATURE:
<223> OTHER INFORMATION: Synthetic: Exemplary 5' sequence including
      polyadenylation, (poly A) sequence

<400> SEQUENCE: 33
ttaattgagg ggccgggctc gagtgcctaa taaaaaacat ttattttcat tgccccctgc       60
agaagcttta aaccggttat cgataatcaa cctc                                   94

<210> SEQ ID NO 34
<211> LENGTH: 2675
```

<212> TYPE: DNA
<213> ORGANISM: Artificial Sequence
<220> FEATURE:
<223> OTHER INFORMATION: Synthetic: Exemplary eNOX1pr-FoxP3(P1)-IL10
    nucleotide sequence

<400> SEQUENCE: 34

```
ggggttcctg cggccgcacg cgtctgcagc ccatgcatga ggaggggatt cccaagatcg      60
aggaggggat tcccaagatc gaggagggga ttcccaagat caaaagtatg caaatccctg     120
aaaaagtatg caaatccctg atttgaaaca gcttccttac cacacacgct tccctcccta     180
cttctcctga agtaatctgt ttacagaccc agactaataa tcttttttat gagaaacttt     240
agcaaatctt ttatctagga aggccaatgc ttcacattag gtcatgttga taagatgatg     300
agagagaata ttttcatcca agaatgttgc tatttcctga agcagtaaaa tccccacagg     360
taaaacccctt gtggttctca tagatagggc tggtctatct aagctgatag cacagttctg     420
tccagagaag gaaggcagaa taaacttatt cattcccagg aactcttggg gtaggtgtgt     480
gtttttcaca tcttaaaggc tcacagaccc tgcgctggac aaattgttcc attcctgaag     540
gacctctcca gaatccggat tgctgaatct tccctgttgc ctagaagggc tccaaaccac     600
ctcttgacat gaacgcgtgc caccatgccg aatcccggc caggcaagcc cagtgccccg     660
tcacttgccc ttgggcctag tcctgggct tcaccatcct ggcgagctgc acctaaggca     720
tctgacctct tggggcacg aggaccgggc gggacgtttc agggaaggga ccttagaggc     780
ggagctcatg caagctcttc ttcactgaac ccgatgccgc cgagtcagtt gcaactcccc     840
acactcccac tcgtaatggt ggcgcccctc ggcgcaagac tcggacctct cccacacctg     900
caagccctct tgcaggacag accacacttc atgcaccaac tttcaacggt tgacgcacac     960
gcacggacac cagtgctgca agttcatcca cttgaatccc ctgccatgat cagcctgaca    1020
ccgcctacta ccgcgacagg tgtcttttct ttgaaagcga ggcctggatt gccacctggc    1080
atcaatgtgg cgtccctgga gtgggtttcc cgcgaacctg ctctcctgtg cacatttcca    1140
aacccgagtg cgccgcgaaa agatagtacg ttgtccgcag tacctcagag ctcatatcca    1200
cttttggcaa acggtgtgtg taaatggcct ggatgcgaaa aagtattcga agagccggag    1260
gacttttttga acattgcca agctgaccac ctgctcgatg atcggtcaac cgcgcaatgc    1320
agggtgcaaa tgcaagttgt acaacagctc gaattgcagt tggcgaagga caaggagagg    1380
ctgcaagcaa tgatgaccca tcttcatgtt aaaatggccc tgaccaaggc aagctctgtt    1440
gcaagctccg acaaaggctc ttgctgtatc gtagcggcgg gatctcaagg accggtcgtc    1500
ccagcgtgga gtggccctcg ggaagcccct gatagtcttt tcgccgtgag acgccacctg    1560
tggggcagcc atgaaaactc cacttttcct gaattttgc acaatatgga ctactttaag    1620
ttccataaca tgcgcccccc gtttacatac gcgacgctca tccggtgggc aatcttggaa    1680
gcgcctgaaa acaacgaac cttgaacgag atatatcatt ggttcacgcg aatgttcgct    1740
ttcttcagaa atcacccggc tacttggaag aatgccataa gacacaatct ttctctccat    1800
aaatgctttg taagggtcga gtccgaaaaa ggggcagtat ggactgttga cgagctggag    1860
tttcggaaaa agcggtcaca acgccgtca agatgctcaa accctacccc aggcccttga    1920
ttagataaag gctgtctccg cgcctatata aaactcttgt ttttctttt tctctatcag    1980
ttcatttgta gcatcttaat ttactatcct tctactatca gttgccgccg ccgtcgacgc    2040
caccatgcac tcttctgcac ttctgtgctg cctcgtgctc ctgacaggtg tcagggcgag    2100
tcccggtcag ggtacgcaat ctgaaaactc ctgcacccac tttccgggga atttgcccaa    2160
```

```
catgctgagg gatctgagag acgctttcag ccgcgttaag acattcttcc agatgaaaga    2220
tcagctcgat aatcttctgt tgaaagagtc actgcttgag gattttaaag ggtatttggg    2280
gtgccaggct ctgtcagaaa tgatacagtt ctatctcgaa gaggtgatgc ctcaagcgga    2340
gaaccaagat ccagacataa aggctcacgt taattccttg ggcgagaatc tgaaaaccct    2400
gaggcttagg ctgagacgct gtcatcgctt cttgccctgt gaaaacaaat ccaaagcggt    2460
agagcaggtc aaaaatgcct ttaataagct gcaagagaag gggatatata aggcaatgtc    2520
tgagtttgat atctttataa actatataga agcttacatg acaatgaaaa ttcggaatta    2580
gttaattgag gggccgggct cgagtgccta ataaaaaaca tttattttca ttgcccctg     2640 cagaagcttt aaaccggtta tcgataatca acctc                               2675
```

<210> SEQ ID NO 35
<211> LENGTH: 715
<212> TYPE: PRT
<213> ORGANISM: Homo sapiens
<220> FEATURE:
<221> NAME/KEY: misc_feature
<222> LOCATION: (1)..(715)
<223> OTHER INFORMATION: Exemplary wildtype human FoxP2 sequence

<400> SEQUENCE: 35

```
Met Met Gln Glu Ser Ala Thr Glu Thr Ile Ser Asn Ser Ser Met Asn
1               5                   10                  15

Gln Asn Gly Met Ser Thr Leu Ser Ser Gln Leu Asp Ala Gly Ser Arg
            20                  25                  30

Asp Gly Arg Ser Ser Gly Asp Thr Ser Ser Glu Val Ser Thr Val Glu
        35                  40                  45

Leu Leu His Leu Gln Gln Gln Ala Leu Gln Ala Ala Arg Gln Leu
    50                  55                  60

Leu Leu Gln Gln Gln Thr Ser Gly Leu Lys Ser Pro Lys Ser Ser Asp
65                  70                  75                  80

Lys Gln Arg Pro Leu Gln Val Pro Val Ser Val Ala Met Met Thr Pro
                85                  90                  95

Gln Val Ile Thr Pro Gln Gln Met Gln Gln Ile Leu Gln Gln Gln Val
            100                 105                 110

Leu Ser Pro Gln Gln Leu Gln Ala Leu Leu Gln Gln Gln Gln Ala Val
        115                 120                 125

Met Leu Gln Gln Gln Gln Leu Gln Glu Phe Tyr Lys Lys Gln Gln Glu
    130                 135                 140

Gln Leu His Leu Gln Leu Leu Gln Gln Gln Gln Gln Gln Gln Gln Gln
145                 150                 155                 160

Gln Gln Gln Gln Gln Gln Gln Gln Gln Gln Gln Gln Gln Gln Gln Gln
                165                 170                 175

Gln Gln Gln Gln Gln Gln Gln Gln Gln Gln Gln Gln Gln Gln Gln His
            180                 185                 190

Pro Gly Lys Gln Ala Lys Glu Gln Gln Gln Gln Gln Gln Gln Gln Gln
        195                 200                 205

Gln Leu Ala Ala Gln Gln Leu Val Phe Gln Gln Leu Leu Gln Met
    210                 215                 220

Gln Gln Leu Gln Gln Gln Gln His Leu Leu Ser Leu Gln Arg Gln Gly
225                 230                 235                 240

Leu Ile Ser Ile Pro Pro Gly Gln Ala Ala Leu Pro Val Gln Ser Leu
                245                 250                 255
```

```
Pro Gln Ala Gly Leu Ser Pro Ala Glu Ile Gln Leu Trp Lys Glu
            260                 265                 270

Val Thr Gly Val His Ser Met Glu Asp Asn Gly Ile Lys His Gly Gly
275                 280                 285

Leu Asp Leu Thr Thr Asn Asn Ser Ser Ser Thr Thr Ser Ser Asn Thr
    290                 295                 300

Ser Lys Ala Ser Pro Pro Ile Thr His His Ser Ile Val Asn Gly Gln
305                 310                 315                 320

Ser Ser Val Leu Ser Ala Arg Arg Asp Ser Ser His Glu Glu Thr
                325                 330                 335

Gly Ala Ser His Thr Leu Tyr Gly His Gly Val Cys Lys Trp Pro Gly
            340                 345                 350

Cys Glu Ser Ile Cys Glu Asp Phe Gly Gln Phe Leu Lys His Leu Asn
            355                 360                 365

Asn Glu His Ala Leu Asp Asp Arg Ser Thr Ala Gln Cys Arg Val Gln
    370                 375                 380

Met Gln Val Val Gln Gln Leu Glu Ile Gln Leu Ser Lys Glu Arg Glu
385                 390                 395                 400

Arg Leu Gln Ala Met Met Thr His Leu His Met Arg Pro Ser Glu Pro
        405                 410                 415

Lys Pro Ser Pro Lys Pro Leu Asn Leu Val Ser Ser Val Thr Met Ser
            420                 425                 430

Lys Asn Met Leu Glu Thr Ser Pro Gln Ser Leu Pro Gln Thr Pro Thr
            435                 440                 445

Thr Pro Thr Ala Pro Val Thr Pro Ile Thr Gln Gly Pro Ser Val Ile
    450                 455                 460

Thr Pro Ala Ser Val Pro Asn Val Gly Ala Ile Arg Arg Arg His Ser
465                 470                 475                 480

Asp Lys Tyr Asn Ile Pro Met Ser Ser Glu Ile Ala Pro Asn Tyr Glu
                485                 490                 495

Phe Tyr Lys Asn Ala Asp Val Arg Pro Pro Phe Thr Tyr Ala Thr Leu
            500                 505                 510

Ile Arg Gln Ala Ile Met Glu Ser Ser Asp Arg Gln Leu Thr Leu Asn
        515                 520                 525

Glu Ile Tyr Ser Trp Phe Thr Arg Thr Phe Ala Tyr Phe Arg Arg Asn
    530                 535                 540

Ala Ala Thr Trp Lys Asn Ala Val Arg His Asn Leu Ser Leu His Lys
545                 550                 555                 560

Cys Phe Val Arg Val Glu Asn Val Lys Gly Ala Val Trp Thr Val Asp
                565                 570                 575

Glu Val Glu Tyr Gln Lys Arg Arg Ser Gln Lys Ile Thr Gly Ser Pro
            580                 585                 590

Thr Leu Val Lys Asn Ile Pro Thr Ser Leu Gly Tyr Gly Ala Ala Leu
        595                 600                 605

Asn Ala Ser Leu Gln Ala Ala Leu Ala Glu Ser Ser Leu Pro Leu Leu
    610                 615                 620

Ser Asn Pro Gly Leu Ile Asn Asn Ala Ser Ser Gly Leu Leu Gln Ala
625                 630                 635                 640

Val His Glu Asp Leu Asn Gly Ser Leu Asp His Ile Asp Ser Asn Gly
                645                 650                 655

Asn Ser Ser Pro Gly Cys Ser Pro Gln Pro His Ile His Ser Ile His
            660                 665                 670

Val Lys Glu Glu Pro Val Ile Ala Glu Asp Glu Asp Cys Pro Met Ser
```

```
                     675                 680                 685
Leu Val Thr Thr Ala Asn His Ser Pro Glu Leu Glu Asp Asp Arg Glu
    690                 695                 700

Ile Glu Glu Glu Pro Leu Ser Glu Asp Leu Glu
705                 710                 715

<210> SEQ ID NO 36
<211> LENGTH: 678
<212> TYPE: PRT
<213> ORGANISM: Homo sapiens
<220> FEATURE:
<221> NAME/KEY: misc_feature
<222> LOCATION: (1)..(678)
<223> OTHER INFORMATION: Exemplary wildtype human FoxP4 sequence

<400> SEQUENCE: 36

Met Met Val Glu Ser Ala Ser Glu Thr Ile Arg Ser Ala Pro Ser Gly
1               5                   10                  15

Gln Asn Gly Val Gly Ser Leu Ser Gly Gln Ala Asp Gly Ser Ser Gly
            20                  25                  30

Gly Ala Thr Gly Thr Thr Ala Ser Gly Thr Gly Arg Glu Val Thr Thr
        35                  40                  45

Gly Ala Asp Ser Asn Gly Glu Met Ser Pro Ala Glu Leu Leu His Phe
    50                  55                  60

Gln Gln Gln Gln Ala Leu Gln Val Ala Arg Gln Phe Leu Leu Gln Gln
65                  70                  75                  80

Ala Ser Gly Leu Ser Ser Pro Gly Asn Asn Asp Ser Lys Gln Ser Ala
                85                  90                  95

Ser Ala Val Gln Val Pro Val Ser Val Ala Met Met Ser Pro Gln Met
            100                 105                 110

Leu Thr Pro Gln Gln Met Gln Gln Ile Leu Ser Pro Pro Gln Leu Gln
        115                 120                 125

Ala Leu Leu Gln Gln Gln Ala Leu Met Leu Gln Gln Glu Tyr Tyr
    130                 135                 140

Lys Lys Gln Gln Glu Gln Leu His Leu Gln Leu Leu Thr Gln Gln
145                 150                 155                 160

Ala Gly Lys Pro Gln Pro Lys Glu Ala Leu Gly Asn Lys Gln Leu Ala
                165                 170                 175

Phe Gln Gln Gln Leu Leu Gln Met Gln Gln Leu Gln Gln Gln His Leu
            180                 185                 190

Leu Asn Leu Gln Arg Gln Gly Leu Val Ser Leu Gln Pro Asn Gln Ala
        195                 200                 205

Ser Gly Pro Leu Gln Thr Leu Pro Gln Ala Ala Val Cys Pro Thr Asp
    210                 215                 220

Leu Pro Gln Leu Trp Lys Gly Glu Gly Ala Pro Gly Gln Pro Ala Glu
225                 230                 235                 240

Asp Ser Val Lys Gln Glu Gly Leu Asp Leu Thr Gly Thr Ala Ala Thr
                245                 250                 255

Ala Thr Ser Phe Ala Ala Pro Pro Lys Val Ser Pro Pro Leu Ser His
            260                 265                 270

His Thr Leu Pro Asn Gly Gln Pro Thr Val Leu Thr Ser Arg Arg Asp
        275                 280                 285

Ser Ser Ser His Glu Glu Thr Pro Gly Ser His Pro Leu Tyr Gly His
    290                 295                 300

Gly Glu Cys Lys Trp Pro Gly Cys Glu Thr Leu Cys Glu Asp Leu Gly
305                 310                 315                 320
```

Gln Phe Ile Lys His Leu Asn Thr Glu His Ala Leu Asp Asp Arg Ser
            325                 330                 335

Thr Ala Gln Cys Arg Val Gln Met Gln Val Val Gln Leu Gln Leu Glu Ile
        340                 345                 350

Gln Leu Ala Lys Glu Ser Glu Arg Leu Gln Ala Met Met Ala His Leu
            355                 360                 365

His Met Arg Pro Ser Glu Pro Lys Pro Phe Ser Gln Pro Leu Asn Pro
    370                 375                 380

Val Pro Gly Ser Ser Phe Ser Lys Val Thr Val Ser Ala Ala Asp
385                 390                 395                 400

Ser Phe Pro Asp Gly Leu Val His Pro Thr Ser Ala Ala Pro
            405                 410                 415

Val Thr Pro Leu Arg Pro Pro Gly Leu Gly Ser Ala Ser Leu His Gly
            420                 425                 430

Gly Gly Pro Ala Arg Arg Ser Ser Asp Lys Phe Cys Ser Pro Ile
        435                 440                 445

Ser Ser Glu Leu Ala Gln Asn His Glu Phe Tyr Lys Asn Ala Asp Val
    450                 455                 460

Arg Pro Pro Phe Thr Tyr Ala Ser Leu Ile Arg Gln Ala Ile Leu Glu
465                 470                 475                 480

Thr Pro Asp Arg Gln Leu Thr Leu Asn Glu Ile Tyr Asn Trp Phe Thr
            485                 490                 495

Arg Met Phe Ala Tyr Phe Arg Arg Asn Thr Ala Thr Trp Lys Asn Ala
        500                 505                 510

Val Arg His Asn Leu Ser Leu His Lys Cys Phe Val Arg Val Glu Asn
    515                 520                 525

Val Lys Gly Ala Val Trp Thr Val Asp Glu Arg Glu Tyr Gln Lys Arg
    530                 535                 540

Arg Pro Pro Lys Met Thr Gly Ser Pro Thr Leu Val Lys Asn Met Ile
545                 550                 555                 560

Ser Gly Leu Ser Tyr Gly Ala Leu Asn Ala Ser Tyr Gln Ala Ala Leu
            565                 570                 575

Ala Glu Ser Ser Phe Pro Leu Leu Asn Ser Pro Gly Met Leu Asn Pro
        580                 585                 590

Gly Ser Ala Ser Ser Leu Leu Pro Leu Ser His Asp Asp Val Gly Ala
    595                 600                 605

Pro Val Glu Pro Leu Pro Ser Asn Gly Ser Ser Pro Arg Leu
    610                 615                 620

Ser Pro Pro Gln Tyr Ser His Gln Val Gln Val Lys Glu Glu Pro Ala
625                 630                 635                 640

Glu Ala Glu Glu Asp Arg Gln Pro Gly Pro Leu Gly Ala Pro Asn
            645                 650                 655

Pro Ser Ala Ser Gly Pro Pro Glu Asp Arg Asp Leu Glu Glu Glu Leu
            660                 665                 670

Pro Gly Glu Glu Leu Ser
            675

<210> SEQ ID NO 37
<211> LENGTH: 22
<212> TYPE: DNA
<213> ORGANISM: Artificial Sequence
<220> FEATURE:
<223> OTHER INFORMATION: Synthetic: FoxP3(P1) forward primer

<400> SEQUENCE: 37
aaagatagta cgttgtccgc ag                                           22

<210> SEQ ID NO 38
<211> LENGTH: 20
<212> TYPE: DNA
<213> ORGANISM: Artificial Sequence
<220> FEATURE:
<223> OTHER INFORMATION: Synthetic: FoxP3(P1) reverse primer

<400> SEQUENCE: 38
atttgcaccc tgcattgcgc                                              20

<210> SEQ ID NO 39
<211> LENGTH: 20
<212> TYPE: DNA
<213> ORGANISM: Artificial Sequence
<220> FEATURE:
<223> OTHER INFORMATION: Synthetic: IL10 forward primer

<400> SEQUENCE: 39
tctgtgctgc ctcgtgctcc                                              20

<210> SEQ ID NO 40
<211> LENGTH: 20
<212> TYPE: DNA
<213> ORGANISM: Artificial Sequence
<220> FEATURE:
<223> OTHER INFORMATION: Synthetic: IL10 reverse primer

<400> SEQUENCE: 40
tctgacagag cctggcaccc                                              20

<210> SEQ ID NO 41
<211> LENGTH: 21
<212> TYPE: DNA
<213> ORGANISM: Artificial Sequence
<220> FEATURE:
<223> OTHER INFORMATION: Synthetic: mGAPDH forward primer

<400> SEQUENCE: 41
tccactcacg gcaaattcaa c                                            21

<210> SEQ ID NO 42
<211> LENGTH: 21
<212> TYPE: DNA
<213> ORGANISM: Artificial Sequence
<220> FEATURE:
<223> OTHER INFORMATION: Synthetic: mGAPDH reverse primer

<400> SEQUENCE: 42
cgctcctgga agatggtgat g                                            21

US 11,091,524 B1

COMPOSITIONS FOR TREATMENT OF VASCULAR DISEASE

CROSS-REFERENCE TO RELATED APPLICATIONS

This application claims the benefit of priority of U.S. Provisional Application No. 63/013,869, filed Apr. 22, 2020, which is incorporated by reference herein in its entirety for any purpose.

SEQUENCE LISTING

The present application is being filed along with a Sequence Listing in electronic format. The Sequence Listing is provided as a file entitled 2020-10-19_01258-0001-00US-T1_ST25.txt created Oct. 19, 2020, which is 50 Kb in size. The information in the electronic format of the sequence listing is incorporated herein by reference in its entirety.

FIELD

The present disclosure relates to compositions and methods for treating vascular disease, and potentially other inflammation-associated diseases such as asthma, diabetes, arthritis, dementia, Alzheimer's disease, macular degeneration, age-related diseases, etc. The present disclosure also relates to promoters for regulating expression of transgenes in response to vascular pathology, including core NOX1 promoters and variants thereof described herein. The present disclosure further relates to vectors and expression systems comprising a core NOX1 promoter described herein, including, for example, AAV vectors having increased loading capacity for expressing multiple proteins. The present disclosure further relates to variant FOXP polypeptides having a zinc finger and leucine zipper region of a different FOXP polypeptide. In addition, the present disclosure relates to nucleic acids, vectors, and expression systems encoding FOXP polypeptides described herein and methods of using the same (e.g., gene therapy methods), for example regulated expression of FOXP polypeptides. The present disclosure also relates to a treatment model for establishing atherosclerotic pathology prior to administering a therapeutic agent to identify those capable of treating established as well as preventing ongoing atherosclerotic pathology.

BACKGROUND

Some disorders, such as cystic fibrosis and sickle cell disease, are caused by mutations in a single gene. Multifactorial disorders, on the other hand, are not caused by a single genetic cause and are much more complex. Multifactorial disorders or conditions, such as heart disease, inflammation, cancer, dementia, obesity, and type 2 diabetes, are likely influenced by multiple genes (polygenic) in combination with lifestyle and environmental factors.

The field of gene therapy has experienced recent successes in the treatment of single-gene disorders. Gene therapy generally involves using a carrier (e.g., a virus) to deliver a therapeutic gene (or genes) to target cells for expression of the encoded therapeutic agent(s) for the treatment and/or prevention of a disease or condition. Adeno-associated virus (AAV) is a preferred gene therapy vector because of its proven gene delivery effect, low immunogenicity, and apparent lack of pathogenicity. The generation and use of recombinant AAV to carry and deliver foreign genes into cells, animals, and humans was made possible by foundation work involving AAV molecular biology (Batchu R B, et al., 1995; Cao M, et al., 2014; Hermonat P L, et al., 1984a, 1984b, 1996, 1997a, 1997b, 1997c, 1998, 2014; Labow M A, et al., 1986; LaFace D, et al., 1988), and the first AAV-based gene delivery conducted in 1984 (Hermonat P L, et al., 1984b, 2014). However, AAV's limited 4.7 kb packaging capacity restricts the size and number of promoter elements and coding sequences that can be incorporated into a single vector. Hermonat P L, et al., 1997c. For instance, the inverted terminal repeats and support sequences, such as multiple cloning sites and poly A sequences, alone can take up about 500-600 bp. Hence, there is a need to develop AAV vectors that can deliver multiple genes for the treatment and/or prevention of multifactorial disorders.

AAV is capable of infecting a large range of host cells (both dividing and quiescent) and persisting in an extrachromosomal state without integrating into the genome of the host cells. As a result, AAV delivery of highly active therapeutic genes under the control of a constitutive promoter (e.g., a CMV promoter) can cause unwanted expression of a therapeutic protein in non-target cells. As a result, regulated promoters that respond to specific stimuli are preferred to control the in vivo expression profile of therapeutic genes. Hence, there is a need to develop small regulated promoters that are responsive to stimuli characteristic of the disease or condition being treated, and/or that are responsive to stimuli characteristic of a particular target cell type.

High cholesterol (characteristic of high lipid diets) has been associated with increased risk of cardiovascular disease (including coronary heart disease, stroke, and peripheral vascular disease), diabetes, and high blood pressure. Other multifactorial disorders, such as obesity, fatty liver disease, cancer, and age-related memory loss, may also be associated with high-lipid diets. The additive effects of a high-lipid diet, including elevated levels of reactive oxygen species (ROS), also referred to as oxidative stress, may accumulate slowly over time resulting in delayed diagnosis of the high-lipid associated disorder(s). Gregersen S, et al., 2012. For example, atherosclerosis, is a chronic inflammatory disease of the blood vessels involving the gradual buildup of fatty material on the inner wall of arteries and infiltration of lymphocytes and macrophages causing restricted blood flow. Macrophages penetrate past the endothelial cells of the blood vessels, localize on blood vessel walls, take up (or internalize) oxidized-low density lipoprotein (Ox-LDL) and other lipids through scavenger receptors, and retain the lipid in vesicles. These lipid-laden cells or "foam cells" are a major component of plaque. Unfortunately, high-lipid associated vascular pathologies (such as atherosclerosis) may go undiagnosed until the subject suffers a stroke or heart attack.

There is a need to develop an appropriate animal model of high-lipid associated disorders to test in vivo which therapies may be capable of treating, reducing, and/or reversing the additive and long-term effects resulting from high-lipid diets. For example, prior animal studies using the low density lipoprotein receptor knockout mouse (LDLR-KO) involve introducing the gene therapy vector on or near the same day that the animals are placed on a high cholesterol diet (HCD). Cao M, et al., 2015; Zhu H, et al., JTM 2014; Zhu H, et al., Plos One 2014; Cao M, et al., 2011; Khan J A, et al., 2011; Khan J A, et al., 2010; Dandapat A, et al., BBRC, 2007; Dandapat A, et al., Gene Ther, 2007; Liu Y, et al., 2005. However, because it takes time for a HCD to induce atherosclerotic pathology, the prior model of administering the vector and starting the HCD at the same time cannot test whether the vector is capable of treating, reducing, and/or reversing significant and established atherosclerotic pathology. A treatment model more realistic of the long-term clinical pathology observed with high-lipid associated disorders is needed for developing effective therapies.

Exemplary promoters, therapeutic proteins, vectors (including multi-gene vectors), therapeutic methods, and clinically-relevant animal models for treatment and prevention of high-lipid associated disorders are disclosed herein.

Unlike prior models, the treatment models described herein involve establishing atherosclerotic pathology prior to administering a therapeutic agent (such as a gene therapy vector) to identify therapeutic agents capable of treating, reducing, and/or reversing established as well as preventing ongoing atherosclerotic pathology.

Also described herein are AAV vectors capable of expressing multiple therapeutic genes, such as anti-inflammatory genes, in the presence of a high-lipid environment. For example, core NOX1 promoters were identified and developed to include additional transcriptional elements while maintaining a size small enough for AAV packaging capacity of multiple coding sequences. As described herein, an exemplary core NOX1 promoter was shown to regulate expression of two anti-inflammatory proteins, an exemplary chimeric human FOXP3/FOXP1 polypeptide and human IL10, in the presence of a high-lipid environment. The therapeutic construct was packaged into an AAV vector and tested in the animal model of established atherosclerotic pathology described herein. High resolution ultrasound measurement of systolic blood velocity, lumen cross sectional area, and wall thickness coupled with histological analysis showed significantly less vascular pathology in the AAV-FOXP3(P1)-IL10-treated mice compared to the control vector-treated mice.

SUMMARY

Embodiment 1. An isolated nucleic acid molecule comprising a NOX1 core promoter and a heterologous nucleic acid molecule, wherein the NOX1 core promoter comprises a nucleotide sequence having at least 80%, at least 85%, at least 90%, at least 91%, at least 92%, at least 93%, at least 94%, at least 95%, at least 96%, at least 97%, at least 98%, at least 99%, or 100% sequence identity to SEQ ID NO: 2 or SEQ ID NO: 3.

Embodiment 2. The isolated nucleic acid molecule of embodiment 1, wherein the NOX1 core promoter is less than 600 nucleotides, less than 550 nucleotides, less than 500 nucleotides, less than 480 nucleotides, or less than 470 nucleotides.

Embodiment 3. The isolated nucleic acid molecule of any one of the preceding embodiments, comprising at least one heterologous NFκB binding site.

Embodiment 4. The isolated nucleic acid molecule of embodiment 3, wherein the at least one heterologous NFκB binding site comprises the nucleotide sequence of SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, and/or SEQ ID NO: 20.

Embodiment 5. The isolated nucleic acid molecule of embodiment 3 or embodiment 4, wherein the at least one NFκB binding site comprises the nucleotide sequence of SEQ ID NO: 5.

Embodiment 6. The isolated nucleic acid molecule of any one of the preceding embodiments, comprising at least two, at least three, at least four, or at least five heterologous NFκB binding sites.

Embodiment 7. The isolated nucleic acid molecule of any one of the preceding embodiments, comprising at least one heterologous Oct1 binding site.

Embodiment 8. The isolated nucleic acid molecule of embodiment 7, wherein the at least one Oct1 binding site comprises the nucleotide sequence of SEQ ID NO: 21.

Embodiment 9. The isolated nucleic acid molecule of any one of the preceding embodiments, comprising at least two, at least three, at least four, or at least five Oct1 binding sites.

Embodiment 10. An isolated nucleic acid molecule comprising a nucleotide sequence having at least 80%, at least 85%, at least 90%, at least 91%, at least 92%, at least 93%, at least 94%, at least 95%, at least 96%, at least 97%, at least 98%, or at least 99% sequence identity to the nucleotide sequence of SEQ ID NO: 4.

Embodiment 11. The isolated nucleic acid molecule of any one of the preceding embodiments, comprising the nucleotide sequence of SEQ ID NO: 2, SEQ ID NO: 3, or SEQ ID NO: 4.

Embodiment 12. An isolated nucleic acid molecule comprising the nucleotide sequence of SEQ ID NO: 2 and a heterologous nucleotide sequence.

Embodiment 13. An isolated nucleic acid molecule comprising the nucleotide sequence of SEQ ID NO: 3.

Embodiment 14. An isolated nucleic acid molecule comprising the nucleotide sequence of SEQ ID NO: 4.

Embodiment 15. The isolated nucleic acid molecule of embodiment 13 or embodiment 14, comprising a heterologous nucleic acid molecule.

Embodiment 16. The isolated nucleic acid molecule of any one of the preceding embodiments, wherein the heterologous nucleic acid molecule comprises a heterologous nucleotide sequence encoding an anti-inflammatory molecule or reporter protein.

Embodiment 17. The isolated nucleic acid molecule of embodiment 16, wherein the anti-inflammatory molecule is a wildtype or variant FOXP3 polypeptide and/or IL10.

Embodiment 18. The isolated nucleic acid molecule of embodiment 17, wherein the wildtype or variant FOXP3 polypeptide comprises the amino acid sequence of SEQ ID NO: 24 or SEQ ID NO: 28.

Embodiment 19. An isolated variant FOXP polypeptide comprising the amino acid sequence of a first FOXP polypeptide, wherein a zinc finger and leucine zipper region of the first FOXP polypeptide has been replaced with a zinc finger and leucine zipper region of a second FOXP polypeptide.

Embodiment 20. The isolated variant FOXP polypeptide of embodiment 19, wherein:
a) the first FOXP polypeptide is a FOXP3 polypeptide and the second FOXP polypeptide is a FOXP1 polypeptide, a FOXP2 polypeptide, or a FOXP4 polypeptide;
b) the first FOXP polypeptide is a FOXP1 polypeptide and the second FOXP polypeptide is a FOXP2 polypeptide, a FOXP3 polypeptide, or a FOXP4 polypeptide;
c) the first FOXP polypeptide is a FOXP2 polypeptide and the second FOXP polypeptide is a FOXP1 polypeptide, a FOXP3 polypeptide, or a FOXP4 polypeptide; or
d) the first FOXP polypeptide is a FOX4 polypeptide and the second FOXP polypeptide is a FOXP1 polypeptide, a FOXP2 polypeptide, or a FOXP3 polypeptide.

Embodiment 21. The isolated variant FOXP polypeptide of embodiment 19 or embodiment 20, wherein the first FOXP polypeptide is a FOXP3 polypeptide and the second FOXP polypeptide is a FOXP1 polypeptide.

Embodiment 22. The isolated variant FOXP polypeptide of any one of embodiments 19 to 21, wherein the zinc finger and leucine zipper region of the second FOXP polypeptide comprises the amino acid sequence of SEQ ID NO: 27.

Embodiment 23. The isolated variant FOXP polypeptide of any one of embodiments 19 to 22, comprising an amino acid sequence having at least 97%, at least 98%, at least 99%, or 100% sequence identity to the amino acid sequence of SEQ ID NO: 28.

Embodiment 24. The isolated variant FOXP polypeptide of any one of embodiments 19 to 23, wherein the polypeptide comprises the amino acid sequence of SEQ ID NO: 28.

Embodiment 25. An isolated polypeptide comprising the amino acid sequence of SEQ ID NO: 28.

Embodiment 26. An isolated nucleic acid comprising the nucleotide sequence of SEQ ID NO: 29 or SEQ ID NO: 34.

Embodiment 27. An isolated nucleic acid comprising a nucleic acid sequence encoding the variant FOXP polypeptide of any one of embodiments 19 to 25.

Embodiment 28. An isolated contiguous nucleic acid comprising a first nucleic acid sequence encoding a first therapeutic polypeptide and a second nucleic acid sequence encoding a second therapeutic polypeptide, wherein the first therapeutic polypeptide comprises the variant FOXP polypeptide of any one of embodiments 19 to 25.

Embodiment 29. The isolated nucleic acid of embodiment 28, wherein the second nucleic acid sequence is downstream of the first nucleic acid sequence.

Embodiment 30. The isolated nucleotide of embodiment 28, wherein the first nucleic acid sequence is downstream of the second nucleic acid sequence.

Embodiment 31. The isolated nucleic acid of any one of embodiments 28 to 30, wherein the second therapeutic polypeptide is a signaling protein, such as a cytokine, a growth factor, or a chemokine.

Embodiment 32. The isolated nucleic acid of any one of embodiments 28 to 31, wherein the second therapeutic polypeptide is an IL10 polypeptide.

Embodiment 33. The isolated nucleic acid of any one of embodiments 28 to 32, wherein the second therapeutic polypeptide comprises the amino acid sequence of SEQ ID NO: 31.

Embodiment 34. The isolated nucleic acid of any one of embodiments 28 to 33, wherein the first nucleic acid sequence and/or the second nucleic acid sequence is operatively linked to a first promoter.

Embodiment 35. The isolated nucleic acid of any one of embodiments 28 to 34, wherein the second nucleic acid sequence is operatively linked to a second promoter.

Embodiment 36. The isolated nucleic acid of embodiment 35 or embodiment 35, wherein the first promoter and/or the second promoter is a constitutive promoter.

Embodiment 37. The isolated nucleic acid of any one of embodiments 34 to 36, wherein the first promoter and/or the second promoter is a cytomegalovirus (CMV) immediate early promoter, a simian virus 40 (SV40) early promoter, a phosphoglycerate kinase 1 (PGK1) promoter, a human β-actin promoter, or a chicken β-actin promoter and CMV early enhancer.

Embodiment 38. The isolated nucleic acid of any one of embodiments 34 to 37, wherein the first promoter and/or the second promoter is a regulated promoter.

Embodiment 39. The isolated nucleic acid of any one of embodiments 34 to 38, wherein the first promoter and/or the second promoter is a tissue-specific promoter or a pathology-specific promoter.

Embodiment 40. The isolated nucleic acid of any one of embodiments 34 to 39, wherein the first promoter and/or the second promoter is activated by sheer stress and/or dyslipidemia.

Embodiment 41. The isolated nucleic acid of any one of embodiments 34 to 40, wherein the first promoter and/or the second promoter is activated by Angiotensin-2 (Ang II), Lipopolysaccharides (LPS), Oxidized Low Density Lipoprotein (Ox-LDL), and/or carbamylated LDL.

Embodiment 42. The isolated nucleic acid of any one of embodiments 34 to 41, wherein the first promoter and/or the second promoter comprises the nucleic acid of any one of embodiments 1 to 15.

Embodiment 43. The isolated nucleic acid of any one of embodiments 26 to 42, comprising a TATA box between the first nucleic acid sequence and the second nucleic acid sequence.

Embodiment 44. The isolated nucleic acid of any one of embodiments 26 to 43, comprising at least one polyadenylation sequence.

Embodiment 45. The isolated nucleic acid of any one of embodiments 26 to 44, comprising adeno-associated virus (AAV) inverted terminal repeats.

Embodiment 46. A vector comprising the nucleic acid of any one of embodiments 1 to 18 or any one of embodiments 26 to 45.

Embodiment 47. The vector of embodiment 46, wherein the vector is a virus vector.

Embodiment 48. The vector of embodiment 46 or embodiment 47, wherein the vector is an adeno-associated virus (AAV) vector, an adenovirus vector, a retrovirus vector, a herpesvirus vector, or a pox virus vector.

Embodiment 49. The vector of any one of embodiments 46 to 48, wherein the vector is an adeno-associated virus (AAV) vector.

Embodiment 50. The vector of any one of embodiments 46 to 49, wherein the vector is an adeno-associated virus (AAV) vector having a capsid serotype selected from the group consisting of AAV1, AAV2, AAV3, AAV4, AAV5, AAV6, AAV7, AAV8, AAV9, AAV10, AAV11, AAV12, AAV13, and any variant thereof.

Embodiment 51. A cultured host cell comprising the nucleic acid molecule of any one of embodiments 1 to 18 or any one of embodiments 26 to 45, the variant FOXP polypeptide of any one of embodiments 19 to 24, or the vector of any one of embodiments 46 to 50.

Embodiment 52. A pharmaceutical composition comprising the nucleic acid molecule of any one of embodiments 1 to 18 or any one of embodiments 26 to 45, the variant FOXP polypeptide of any one of embodiments 19 to 24, the vector of any one of embodiments 46 to 50, or the cultured host cell of embodiment 51.

Embodiment 53. A method comprising administering to a subject the nucleic acid molecule of any one of embodiments 1 to 18 or any one of embodiments 26 to 45, the variant FOXP polypeptide of any one of embodiments 19 to 24, the vector of any one of embodiments 46 to 50, the cultured host cell of embodiment 51, or the pharmaceutical composition of embodiment 52.

Embodiment 54. A method of treating a subject comprising administering to the subject the nucleic acid molecule of any one of embodiments 1 to 18 or any one of embodiments 26 to 45, the variant FOXP polypeptide of any one of embodiments 19 to 24, the vector of any one of embodiments 46 to 50, the cultured host cell of embodiment 51, or the pharmaceutical composition of embodiment 52.

Embodiment 55. The method of embodiment 53 or embodiment 54, wherein the subject has a vascular disease and/or a cardiovascular disease.

Embodiment 56. The method of any one of embodiments 53 to 55, wherein the subject has an inflammation-associated disease.

Embodiment 57. The method of any one of embodiments 53 to 56, wherein the subject has an age-associated disease.

Embodiment 58. The method of any one of embodiments 53 to 57, wherein the subject has atherosclerosis.

Embodiment 59. The method of any one of embodiments 53 to 58, wherein the subject has arthritis, such as psoriatic arthritis, rheumatoid arthritis, and/or gouty arthritis.

Embodiment 60. The method of any one of embodiments 53 to 59, wherein the subject has dementia.

Embodiment 61. The method of any one of embodiments 53 to 60, wherein the subject has Alzheimer's disease.

Embodiment 62. The method of any one of embodiments 53 to 61, wherein the subject has asthma.

Embodiment 63. The method of any one of embodiments 53 to 62, wherein the subject has macular degeneration of the retina.

Embodiment 64. The method of any one of embodiments 53 to 63, wherein the subject has arterial disease of the aorta, carotid artery disease, coronary artery disease, atherosclerotic cerebrovascular disease, peripheral artery disease, and/or diabetes mellitus.

Embodiment 65. A method of screening a therapeutic agent comprising:
  a) maintaining a low density lipoprotein receptor knockout (LDLR-KO) or Apo E knockout animal (such as a mouse or rat) on a high cholesterol diet; and
  b) administering a therapeutic agent to the animal no earlier than 56 days after beginning the high cholesterol diet.

Embodiment 66. The testing method of embodiment 65, wherein the method further comprises:
  c) assessing the blood flow velocity, cross-sectional area of the aorta lumen, and/or the aortic wall thickness of the animal by ultrasound imaging.

Embodiment 67. The testing method of embodiment 65 or embodiment 66, wherein the therapeutic agent is administered no earlier than 63 days, no earlier than 70 days, no earlier than 77 days, no earlier than 84 days, no earlier than 91 days, or no earlier than 98 days after beginning the high cholesterol diet.

Embodiment 68. The testing method of any one of embodiments 65 to 67, wherein the therapeutic agent is the nucleic acid of any one of embodiments 1 to 18 or any one of embodiments 26 to 45, the variant FOXP polypeptide of any one of embodiments 19 to 24, the vector of any one of embodiments 46 to 50, or the pharmaceutical composition of embodiment 51.

Embodiment 69. The method of any one of embodiments 53 to 68, wherein the nucleic acid, the variant FOXP polypeptide, the vector, the cultured host cell, the pharmaceutical composition, or the therapeutic agent is administered to the subject or the animal once.

Embodiment 70. The method of any one of embodiments 53 to 69, wherein the nucleic acid, the variant FOXP polypeptide, the vector, the cultured host cell, the pharmaceutical composition, or the therapeutic agent is administered to the subject or the animal every other day, weekly, or monthly.

Embodiment 71. The method of any one of embodiments 53 to 70, wherein the nucleic acid, the variant FOXP polypeptide, the vector, the cultured host cell, the pharmaceutical composition, or the therapeutic agent is administered to the subject or the animal via intravenous injection, arterial injection, intramuscular injection, or injection into a section of ligated artery or vein.

Embodiment 72. The method of any one of embodiments 53 to 71, wherein a therapeutically effective amount of the nucleic acid, the variant FOXP polypeptide, the vector, the cultured host cell, the pharmaceutical composition, or the therapeutic agent is administered to the subject or the animal.

Embodiment 73. The method of any one of embodiments 53 to 72, wherein the vector is administered to the subject or the animal at a dose of $1\times10^{10}$ encapsidated genomes, $1\times10^{11}$ encapsidated genomes, $1\times10^{12}$ encapsidated genomes, $1\times10^{13}$ encapsidated genomes, $1\times10^{10}$ to $1\times10^{13}$ encapsidated genomes, $1\times10^{10}$ to $1\times10^{12}$ encapsidated genomes, $1\times10^{11}$ to $1\times10^{12}$ encapsidated genomes, or $1\times10^{10}$ to $1\times10^{11}$ encapsidated genomes.

Additional objects and advantages will be set forth in part in the description which follows, and in part will be obvious from the description, or may be learned by practice. The objects and advantages will be realized and attained by means of the elements and combinations particularly pointed out in the appended claims.

It is to be understood that both the foregoing general description and the following detailed description are exemplary and explanatory only and are not restrictive of the claims.

The accompanying drawings, which are incorporated in and constitute a part of this specification, illustrate one (several) embodiment(s) and together with the description, serve to explain the principles described herein.

BRIEF DESCRIPTION OF THE DRAWINGS

FIG. 10A shows weight at 20 weeks among LDLR-KO mice fed a normal diet or fed a high cholesterol diet and administered at 12 weeks either the AAV2/8.eNOXpr-3xFLAG-mCherry vector or the AAV2/8.eNOXpr-FOXP3 (P1)-IL10 vector.

FIG. 10B shows levels of alanine aminotransferase at 20 weeks among LDLR-KO mice fed a normal diet or fed a high cholesterol diet and administered at 12 weeks either the AAV2/8.eNOXpr-3xFLAG-mCherry vector or the AAV2/8.eNOXpr-FOXP3(P1)-IL10 vector.

FIG. 10C shows levels of aspartate aminotransferase at 20 weeks among LDLR-KO mice fed a normal diet or fed a high cholesterol diet and administered at 12 weeks either the AAV2/8.eNOXpr-3xFLAG-mCherry vector or the AAV2/8.eNOXpr-FOXP3(P1)-IL10 vector.

FIG. 10D shows levels of alkaline phosphatase at 20 weeks among LDLR-KO mice fed a normal diet or fed a high cholesterol diet and administered at 12 weeks either the AAV2/8.eNOXpr-3xFLAG-mCherry vector or the AAV2/8.eNOXpr-FOXP3(P1)-IL10 vector.

FIG. 10E shows levels of albumin at 20 weeks among LDLR-KO mice fed a normal diet or fed a high cholesterol diet and administered at 12 weeks either the AAV2/8.eNOXpr-3xFLAG-mCherry vector or the AAV2/8.eNOXpr-FOXP3(P1)-IL10 vector.

DESCRIPTION OF CERTAIN SEQUENCES

Figure 1A:
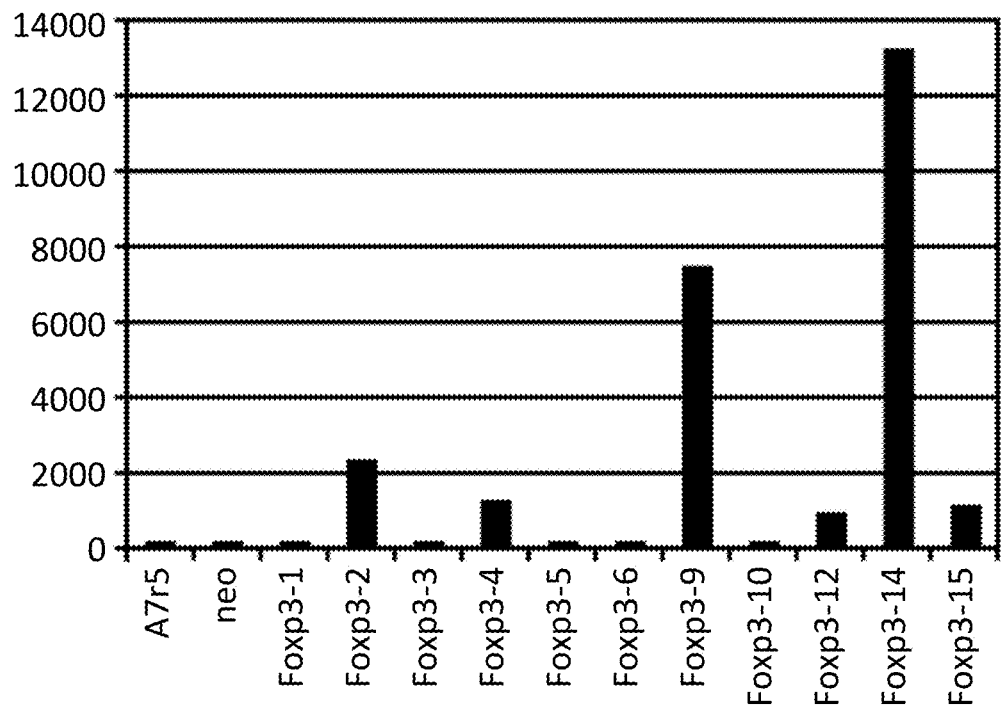
FIG. 1A provides expression levels of FoxP3 mRNA by Quantitative RT-PCR (Q-RT-PCR) in immortal, tissue culture A7R5 rat smooth muscle cells transfected with pSV40-Neo and CMV-FoxP3 expression plasmids and selected with G418.

Table 1 provides a listing of certain sequences referenced herein.

TABLE 1

Description of Certain Sequences

| SEQ ID NO: | SEQUENCE | DESCRIPTION |
|---|---|---|
| 1 | gttttccatatttaaaagtagtaaattggataccatacatgaa aatcagctccaggtggattcaaaacataaatgtaaaatgcaaa aatataaaatttctagaagaaaatataaaagagtatcttgata tctgggtagtgatggatttctaaaacaagacataaaatgcata aatcataaaagaaatgactggtaatcagagtgcattaaaatta agaacttccatttatcagaaaacactattaagagactgaaaag acaagccataaacataagcaataaaagattagtataagattat aaacagaaccctaagaatctaaaagcaaaagaaaaaccaatag aaagatagaccaaaaagtagaataggctcagaataggctcttt taaaaagagaaaactcaaatggccagcagttgaattaaaagat gctcaaactcattagtaatcagggaaatgcaaattaaaatcat aatacgatagttttccacacttacttgaattataaaaacaaaa aagtctggaaaataccaagggttggtaagcatgtagaggaagt agaactctcattcataactctctgtagtatacatttaggtggt cacttcggaacgggtttggaattacacagcaaagtagaatatg tgcaaatctcaggaccctggaattttactcctgggtatatacc ttagagaaactgtagcatatgtgtgacattcgatcaacattgt tccatcatcatatccatcagtagtaggatgaatgaatacatta atgtatattcattcatgcaatggcatattagatagcagtgtaa gtgaaccgcaattacatgtacatgtatgaatctcaaaaaccca atgttgaaagaagcaaaccacagaagcatacatacacactgcc aggtttcatttacaaaaagttcaaaaacaggaaaaactaaaca atatattgcttagggatgcaattatagttagtaaaaatataaa gaaaaataacagaatgattacccccaaatttcaggatagtgatt acatccggtgggtagaggaggggaagaagatagatgtgatca gggagggaaatacaaagagctttaagatactggagaaaaatag tctattttctttaatctgagtagtgaacacatagatacttatt ccttaaaattattctttaagttacatatgtatgttttatatac tcttctgtgtatatttcaccattttagaaaagggaaaaaaaat cagtgcccagagctgaacacacaactctagtaaatctatcata ctagaagacaatcatctccattcttttgagtgctctgcctctg tttattttgaaccaaagtgcacttttatacttgttaaattttc tcttgctctatttggcccttcttttcacttgtccttccagcca gtcaagttctccccaaagccatcatcatatatgtcaaccacag atcatcctccaggggaactggtatgctaaagtttctgagctag ccaggctgaaatccaaatggcagccggcagatgtggcaacagt ttgaaaagtgcactttgaaacagcttccttaccacacacgctt ccctccctacttctcctgaagtaatctgtttacagacccagac taataatctttttttatgagaaactttagcaaatctttttatcta ggaaggcaatgcttcacattaggtcatgttgataagatgatga gagagaatattttcatccaagaatgttgctatttcctgaagca gtaaaatccccacaggtaaaaccccttgtggttctcatagatag ggctggtctatctaagctgatagcacagttctgtccagagaag gaaggcagaataaacttattcattcccaggaactcttggggta ggtgtgtgttttttcacatcttaaaggctcacagaccctgcgct ggacaaatgttccattcctgaaggacctctccagaatccggat | 5' flanking sequence of human NOX1 gene Nucleotides 1-2027 of GenBank Accession No. DQ314883.1 |

TABLE 1 -continued

Description of Certain Sequences

| SEQ ID NO: | SEQUENCE | DESCRIPTION |
|---|---|---|
|  | tgctgaatcttccctgttgcctagaagggctccaaaccacctc ttgaca |  |
| 2 | tttgaaacagcttccttaccacacacgcttccctccctacttc tcctgaagtaatctgtttacagacccagactaataatctttttt tatgagaaactttagcaaatctttttatctaggaaggcaatgct tcacattaggtcatgttgataagatgatgagagagaatatttt catccaagaatgttgctatttcctgaagcagtaaaatccccac aggtaaaaccttgtggttctcatagatagggctggtctatct aagctgatagcacagttctgtccagagaaggaaggcagaataa acttattcattcccaggaactcttggggtaggtgtgtgttttt cacatcttaaaggctcacagaccctgcgctggacaaatgttcc attcctgaaggacctctccagaatccggattgctgaatcttcc ctgttgcctagaagggctccaaaccacctcttgaca | Exemplary human NOX1 core promoter |
| 3 | tttgaaacagcttccttaccacacacgcttccctccctacttc tcctgaagtaatctgtttacagacccagactaataatctttttt tatgagaaactttagcaaatctttttatctaggaaggccaatgc ttcacattaggtcatgttgataagatgatgagagagaatattt tcatccaagaatgttgctatttcctgaagcagtaaaatcccca caggtaaaaccttgtggttctcatagatagggctggtctatc taagctgatagcacagttctgtccagagaaggaaggcagaata aacttattcattcccaggaactcttggggtaggtgtgtgtttt tcacatcttaaaggctcacagaccctgcgctggacaaattgtt ccattcctgaaggacctctccagaatccggattgctgaatctt ccctgttgcctagaagggctccaaaccacctcttgacatgaac gcgtgccacc | Exemplary variant human NOX1 core promoter |
| 4 | *gagga*<u>*gggatt*</u>*ccc*aagatc*gaggagggattccc*aagatcg *aggagggattccc*aagatcaaaagtatgcaaatccctgaaaa agtatgcaaatccctgatttgaaacagcttccttaccacacac gcttccctccctacttctcctgaagtaatctgtttacagaccc agactaataatctttttatgagaaactttagcaaatctttta tctaggaaggccaatgcttcacattaggtcatgttgataagat gatgagagagaatattttcatccaagaatgttgctatttcctg aagcagtaaaatccccacaggtaaaaccttgtggttctcata gatagggctggtctatctaagctgatagcacagttctgtccag agaaggaaggcagaataaacttattcattcccaggaactcttg ggtaggtgtgtgttttcacatcttaaaggctcacagaccct gcgctggacaaattgttccattcctgaaggacctctccagaat ccggattgctgaatcttccctgttgcctagaagggctccaaac cacctcttgacatgaacgcgtgccacc | Exemplary variant NOX1 core promoter with three NF-κB binding sequences (italic, underlined) and two Oct1 binding sequences (bold, underlined) at the 5' end "eNOX1 promoter" |
| 5 | gggrnyyycc, wherein r is a purine, y is a pyrimidine, and n is any nucleotide | Exemplary consensus sequence of an NF-κB binding site |
| 6 | ggrrnnyycc, wherein r is a purine, y is a pyrimidine, and n is any nucleotide | Exemplary consensus sequence of an NF-κB binding site |
| 7 | rggrnnhhyyb; wherein r is a purine; y is a pyrimidine; h is an adenine, a cytosine, or a thymine; b is a guanine, thymine, or cytosine; and n is any nucleotide | Exemplary consensus sequence of an NF-κB binding site |
| 8 | ggggatyccc, wherein y is a pyrimidine | Exemplary consensus sequence of an NF-κB binding site |
| 9 | gggrntttcc, wherein n is any nucleotide | Exemplary consensus sequence of an NF-κB binding site |
| 10 | nggnnwttcc, wherein w is an adenine or a thymine; and n is any nucleotide | Exemplary consensus sequence of an NF-κB binding site |
| 11 | gggrnnyycc, wherein r is a purine, y is a pyrimidine, and n is any nucleotide | Exemplary consensus sequence of an NF-κB binding site |
| 12 | ggggaatcccc | Exemplary sequence of an NF-κB binding site |

TABLE 1 -continued

Description of Certain Sequences

| SEQ ID NO: | SEQUENCE | DESCRIPTION |
|---|---|---|
| 13 | ggggactttcc | Exemplary sequence of an NF-κB binding site |
| 14 | aggggatctg | Exemplary sequence of an NF-κB binding site |
| 15 | agggaagtta | Exemplary sequence of an NF-κB binding site |
| 16 | ctggggattta | Exemplary sequence of an NF-κB binding site |
| 17 | gggaattccc | Exemplary sequence of an NF-κB binding site |
| 18 | gggaatttcc | Exemplary sequence of an NF-κB binding site |
| 19 | ggggattccc | Exemplary sequence of an NF-κB binding site |
| 20 | gaggagggattcccaagatc | Exemplary sequence of an NF-κB binding site |
| 21 | atgcaaat | Exemplary sequence of an Oct1 binding site |
| 22 | gaggagggattcccaagatcgaggagggattcccaagatcgaggagggattcccaagatcaaaagtatgcaaatccctgaaaaagtatgcaaatccctgatttgaaacagcttccttaccacacacgcttccctccctacttctcctgaagtaatctgtttacagaccgagactaataatctttttatgagaaactttagcaaatcttttatctaggaaggccaatgcttcacattaggtcatgttgataagatgatgagagagaatattttcatccaagaatgttgctatttcctgaagcagtaaaatccccacaggtaaaaccctgtggttctcatagatagggctggtctatctaagctgatagcacagttctgtccagagaaggaaggcagaataaaacttattcattcccaggaactcttggggtaggtgtgtgtttttcacatcttaaaggctcacagacccctgcgctggacaaattgttccattcctgaaggacctctccagaatccggattgctgaatcttccctgttgcctagaagggctccaaaccacctcttgacatgaacgcgtgccaccatgtctgactataaagaccatgatggggactacaaagaccatgatatagattacaaagacgatgatgacaaaatggttagcaaggggaggaagacaatatgcccataattaaagaattcatgcgcttcaaagttcacatggaaggcgtgaacgacatgagttcgagatagaaggcgagggcgaggggcggccctatgagggaacgcagactgctaaactgaaggttactaaaggtggccctcttcctttcgcatgggacatcctgtctccgcagttcatgtatggatccaaggcatatgttaagcatccggctgatataccagattacctcaaattgagctttcctgaagggttttaagtgggaaagggtcatgaactttgaagacggtggagttgtgacagttacacaggattcatcacttcaggacggtgagtttatatacaaggttaaacttagggaactaattttccttccgacggccccgtcatgcagaaaaaaccatggggtggaggcgagctccgagcggatgtacccagaggatggagcactgaagggcgaaataaaacagcgactgaaattgaaagacggaggtcactatgatgcagaagttaagacgacatacaaggccaaaaagccagttcagttgccgggtgcatataacgtcaatatcaagctggacattacatcccacaatggattatacgatagtggagcagtatgagcgggcagaagggcggcactccacaggaggaatggacgaactctataaatgacccaccagccttgtcctaataaaattaagttgcatcattttgtttgactactcgagcccctgca | eNOXpr-3xFLAG-mCherry |
| 23 | MSDYKDHDGDYKDHDIDYKDDDDKMVSKGEEDNMAIIKEFMRFKVHMEGSVNGHEFEIEGEGEGRPYEGTQTAKLKVIKGGPLPFAWDILSPQFMYGSKAYVKHPADIPDYLKLSFPEGFKWERVMNFE | 3xFLAG-mCherry amino acid sequence |

TABLE 1 -continued

Description of Certain Sequences

| SEQ ID NO: | SEQUENCE | DESCRIPTION |
|---|---|---|
|  | DGGVVTVTQDSSLQDGEFIYKVKLRGINFPSDGPVMQKKTMGW EASSERMYPEDGALKGEIKQRLKLKDGGHYDAEVKITYKAKKP VQLPGAYNVNIKLDITSHNEDYTIVEQYERAEGRHSTGGMDEL YK |  |
| 24 | MPNPRPGKPSAPSLALGPSPGASPSWRAAPKASDLLGARGPGG TFQGRDLRGGAHASSSSLNPMPPSQLQLPTLPLVMVAPSGARL GPLPHLQALLQDRPHFMHQLSTVDAHARTPVLQVHPLESPAMI SLTPPTTATGVFSLKARPGLPPGINVASLEWVSREPALLCTFP NPSAPRKDSTLSAVPQSSYPLLANGVCKWPGCEKVFEEPEDFL KHCQADHLLDEKGRAQCLLQREMVQSLEQQLVLEKEKLSAMQA HLAGKMALTKASSVASSDKGSCCIVAAGSQGPVVPAWSGPREA PDSLFAVRRHLWGSHGNSTFPEFLHNMDYFKFHNMRPPFTYAT LIRWAILEAPEKQRTLNEIYHWFTRMFAFFRNHPATWKNAIRH NLSLHKCFVRVESEKGAVWTVDELEFRKKRSQRPSRCSNPTPGP | Exemplary wildtype human FoxP3 amino acid sequence NCBI Ref Sequence: NP_054728.2 |
| 25 | EKGRAQCLLQREMVQSLEQQLVLEKEKLSAPIQAHLAGE | Exemplary human FOXP3 zinc finger and leucine zipper region |
| 26 | MMTPQVITPQQMQQILQQQVLSPQQLQVLLQQQQALMLQLQQL WKEVTSAHTAEETTGNNHSSLDLTTTCVSSSAPSKTSLIMNPH ASTNGQLSVHTPKRESLSHEEHPHSHPLYGHGVCKWPGCEAVC EDFQS FLKHLNSEHALDDRSTAQCRVQMQVVQQLELQLAKDKE RLQAMMTHLHVKSTEPKAAPQPLNLVSSVTLSKSASEASPQSL PHTPTTPTAPLTPVTQGPSVITTTSMHTVGPIRRRYSDKYNVP ISSADIAQNQEFYKNAEVRPPFTYASLIRQAILESPEKQLTLN EIYNWFTRMFAYFRRNAATWKNAVRHNLSLHKCFVRVENVKGA VWTVDEVEFQKRRPQKISGNPSLIKNMQSSHAYCTPLNAALQA SMAENSIPLYTTASMGNPTLGNLASAIREELNGAMEHTNSNES DSSPGRSPMQAVHPVHVKEEPLDPEEAEGPLSLVTTANHSPDF DHDRDYEDEPVNEDME | Exemplary wildtype human FoxP1 sequence GenBank: AF146698.2 |
| 27 | DRSTAQCRVQMQVVQQLELQLAKDKERLQAMMTHLHVK | Exemplary human FOXP1 zinc finger and leucine zipper region |
| 28 | MPNPRPGKPSAPSLALGPSPGASPSWRAAPKASDLLGARGPGG TFQGRDLRGGAHASSSSLNPMPPSQLQLPTLPLVMVAPSGARL GPLPHLQALLQDRPHFMHQLSTVDAHARTPVLQVHPLESPAMI SLTPPTTATGVFSLKARPGLPPGINVASLEWVSREPALLCTFP NPSAPRKDSTLSAVPQSSYPLLANGVCKWPGCEKVFEEPEDFL KHCQADHLL<u>DDRSTAQCRVQMQVVQQLELQLAKDKERLQAMMT HLHVK</u>MALTKASSVASSDKGSCCIVAAGSQGPVVPAWSGPREA PDSLFAVRRHLWGSHGNSTFPEFLHNMDYFKFHNMRPPFTYAT LIRWAILEAPEKQRTLNEIYHWFTRMFAFFRNHPATWKNAIRH NLSLHKCFVRVESEKGAVWTVDELEFRKKRSQRPSRCSNPTPGP | Exemplary FOXP3(P1) amino acid sequence FOXP1 zinc finger and leucine zipper region underlined |
| 29 | atgccgaatcccggccaggcaagcccagtgccccgtcacttg cccttgggcctagtcctggggcttcaccatcctggcgagctgc acctaaggcatctgacctcttgggggcacgaggaccgggcggg acgtttcagggaagggacctcagaggcggagctcatgcaagct cttcttcactgaacccgatgccgccgagtcagttgcaactccc cacactcccactcgtaatggtggcgccctctggcgcaagactc ggacctctcccacacctgcaagccctcttgcaggacagaccac acttcatgcaccaacttcaacggttgacgcacacgcacggac accagtgctgcaagttcatccacttgaatcccctgccatgatc agcctgacaccgcctactaccgcgacaggtgtcttttctttga aagcgaggcctggattgccacctggcatcaatgtggcgtccct ggagtgggtttcccgcgaacctgctctcctgtgcacatttcca aacccgagtcgccgcgaaaagatagtacgttgtccgcagtac ctcagagctcatatccacttttggcaaacggtgtgtgtaaatg gcctggatgcgaaaaagtattcgaagagccggaggactttttg aaacattgccaagctgaccacctgctcgat<u>gatcggtcaaccg cgcaatgcagggtgcaaatgcaagttgtacaacagctcgaatt gcagttggcgaaggacaaggagaggctgcaagcaatgatgacc catcttcatgtt</u>aaaatggccctgaccaaggcaagctctgttg caagctccgacaaaggctcttgctgtatcgtagcggcgggatc tcaaggaccggtcgtcccagcgtggagtggccctcggggaagcc cctgatagtcttttcgccgtgagacgccacctgtggggcagcc atggaaactccacttttcctgaatttttgcacaatatggacta ctttaagttccataacatgcgcccccgtttacatacgcgacg ctcatccggtgggcaatcttggaagcgcctgaaaaacaacgaa | Exemplary FoxP3 (P1) nucleotide sequence FoxP1 zinc finger and leucine zipper region underlined |

TABLE 1 -continued

Description of Certain Sequences

| SEQ ID NO: | SEQUENCE | DESCRIPTION |
|---|---|---|
| | ccttgaacgagatatatcattggttcacgcgaatgttcgcttt cttcagaaatcacccggctacttggaagaatgccataagacac aatctttctctccataaatgctttgtaagggtcgagtccgaaa aaggggcagtatggactgttgacgagctggagtttcggaaaaa gcggtcacaacgcccgtcaagatgctcaaaccctaccccaggc ccttga | |
| 30 | ttagataaaggctgtctccgcgcctatataaaactcttgtttt tcttttttctctatcagttcatttgtagcatcttaatttacta tccttctactatcagttgccgccgccgtcgacgccacc | Exemplary mini-promoter TATA box nucleotide sequence |
| 31 | MHSSALLCCLVLLTGVRASPGQGTQSENSCTHFPGNLPNMLRD LRDAFSRVKTFFQMKDQLDNLLLKESLLEDFKGYLGCQALSEM IQFYLEEVMPQAENQDPPDIKAHVNSLGENLKTLRLRLRRCHRF LPCENKSKAVEQVKNAFNKLQEKGIYKAMSEEDIFINYIEAYM TMKIRN | Exemplary human IL10 amino acid sequence UniProtKB Accession No. P22301 |
| 32 | atgcactcttctgcacttctgtgctgcctcgtgctcctgacag gtgtcagggcgagtcccggtcagggtacgcaatctgaaaactc ctgcacccactttccggggaatttgcccaacatgctgagggat ctgagagacgctttcagccgcgttaagacattcttccagatga agatcagctcgataatcttctgttgaaagagtcactgcttga ggattttaaagggtatttggggtgccaggctctgtcagaaatg atacagttctatctcgaagaggtgatgcctcaagcggagaacc aagatccagacataaaggctcacgttaattccttgggcgagaa tctgaaaaccctgaggcttaggctgagacgctgtcatcgcttc ttgcccctgtgaaaacaaatccaaagcggtagagcaggtcaaa atgcctttaataagctgcaagaagggggatatataaggcaat gtctgagtttgatatcttttataaactatatagaagcttacatg acaatgaaaattcggaattag | Exemplary human IL10 nucleotide sequence |
| 33 | ttaattgaggggccgggctcgagtgcctaataaaaaaacattta ttttcattgcccccctgcagaagctttaaaccggttatcgataa tcaacctc | Exemplary 5' sequence including polyadenylation (poly A) sequence |
| 34 | ggggttcctgcggccgcacgcgtctgcagcccatgcatgagga gggggattcccaagatcgaggaggggattcccaagatcgaggag gggattcccaagatcaaaagtatgcaaatccctgaaaaagtat gcaaatccctgatttgaaacagcttccttaccacacacgcttc cctccctacttctcctgaagtaatctgtttacagacccagact aataatctttttttatgagaaactttagcaaatcttttatctag gaaggccaatgcttcacattaggtcatgttgataagatgatga gagagaatattttcatccaagaatgttgctatttcctgaagca gtaaaatccccacaggtaaaacccttgtggttctcatagatag ggctggtctatctaagctgatagcacagttctgtccagagaag gaaggcagaataaacttattcattcccaggaactcttggggta ggtgtgtgttttcacatcttaaaggctcacagaccctgcgct ggacaaattgttccattcctgaaggacctctccagaatccgga ttgctgaatcttccctgttgcctagaagggctccaaaccacct cttgacatgaacgcgtgccaccatgccgaatcccggccaggc aagcccagtgccccgtcacttgcccttgggcctagtcctgggg cttcaccatcctggcgagctgcacctaaggcatctgacctctt gggggcacgaggaccgggcgggacgtttcaggggaagggaccttt agaggcggagctcatgcaagctcttcttcactgaacccgatgc cgccgagtcagttgcaactccccacactcccactcgtaatggt ggcgccctctggcgcaagactcggacctctcccacacctgcaa gccctcttgcaggacagaccacacttcatgcaccaactttcaa cggttgacgcacacgcacggacaccagtgctgcaagttcatcc acttgaatcccctgccatgatcagcctgacaccgcctactacc gcgacaggtgtcttttctttgaaagcgaggcctggattgccac ctggcatcaatgtggcgtccctggagtgggtttcccgcgaacc tgctctcctgtgcacatttccaaacccgagtgcgccgcgaaaa gatagtacgttgtccgcagtacctcagagctcatatccactttt tggcaaacggtgtgtgtaaatggcctgatgcgaaaaagtatt cgaagagccggaggactttttgaaacattgccaagctgaccac ctgctcgatgatcggtcaaccgcgcaatgcagggtgcaaatgc aagttgtacaacagctcgaattgcagttggcgaaggacaagga gaggctgcaagcaatgatgacccatcttcatgttaaaatgcc ctgaccaaggcaagctctgttgcaagctccgacaaaggctctt gctgtatcgtagcggcgggatctcaaggaccggtcgtcccagc gtggagtggccctcgggaagcccctgatagtcttttcgccgtg agacgccacctgtggggcagccatggaaactccacttttcctg aattttttgcacaatatggactactttaagttccataacatgcg | Exemplary eNOX1pr-FoxP3(P1)-IL10 nucleotide sequence |

TABLE 1 -continued

Description of Certain Sequences

| SEQ ID NO: | SEQUENCE | DESCRIPTION |
|---|---|---|
| | cccccgtttacatacgcgacgctcatccggtgggcaatcttg<br>gaagcgcctgaaaaacaacgaaccttgaacgagatatatcatt<br>ggttcacgcgaatgttcgctttcttcagaaatcacccggctac<br>ttggaagaatgccataagacacaatctttctctccataaatgc<br>tttgtaagggtcgagtccgaaaaaggggcagtatggactgttg<br>acgagctggagtttcggaaaaagcggtcacaacgcccgtcaag<br>atgctcaaaccctaccccaggcccttgattagataaaggctgt<br>ctccgcgcctatataaaactcttgttttctttttctctatc<br>agttcatttgtagcatcttaatttactatccttctactatcag<br>ttgccgccgccgtcgacgccaccatgcactcttctgcacttct<br>gtgctgcctcgtgctcctgacaggtgtcagggcgagtcccggt<br>cagggtacgcaatctgaaaactcctgcacccacttccggga<br>atttgcccaacatgctgagggatctgagagacgctttcagccg<br>cgttaagacattcttccagatgaaagatcagctcgataatctt<br>ctgttgaaagagtcactgcttgaggattttaaagggtatttgg<br>ggtgccaggctctgtcagaaatgatacagttctatctcgaaga<br>ggtgatgctcaagcggagaaccaagatccagacataaaggct<br>cacgttaattccttgggcgagaatctgaaaaaccctgaggctta<br>ggctgagacgctgtcatcgcttcttgccctgtgaaaacaaatc<br>caaagcggtagagcaggtcaaaaatgcctttaataagctgcaa<br>gagaagggatatataaggcaatgtctgagtttgatatcttta<br>taaactatatagaagcttacatgacaatgaaaattcggaatta<br>gttaattgaggggccgggctcgagtgcctaataaaaaacatttt<br>attttcattgccccctgcagaagctttaaaccggttatcgata<br>atcaacctc | |
| 35 | MMQESATETISNSSMNQNGMSTLSSQLDAGSRDGRSSGDTSSE<br>VSTVELLHLQQQQALQAARQLLLQQQTSGLKSPKSSDKQRPLQ<br>VPVSVAMMTPQVITPQQMQQILQQQVLSPQQLQALLQQQQAVM<br>LQQQQLQEFYKKQQEQLHLQLLQQQQQQQQQQQQQQQQQQQQQ<br>QQQQQQQQQQQQQQQQQPGKQAKEQQQQQQQQQLAAQQL<br>VFQQQLLQMQQLQQQQHLLSLQRQGLISIPPGQAALPVQSLPQ<br>AGLSPAEIQQLWKEVTGVHSMEDNGIKHGGLDLTTNNSSSTTS<br>SNTSKASPPITHHSIVNGQSSVLSARRDSSHEETGASHTLYG<br>HGVCKWPGCESICEDFGQFLKHLNNEHALDDRSTAQCRVQMQV<br>VQQLEIQLSKERERLQAMMTHLHMRPSEPKPSPKPLNLVSSVT<br>MSKNMLETSPQSLPQTPTTPTAPVTPITQGPSVITPASVPNVG<br>AIRRRHSDKYNIPMSSEIAPNYEFYKNADVRPPFTYATLIRQA<br>IMESSDRQLTLNETYSWFTRTFAYFRRNAATWKNAVRHNLSLH<br>KCFVRVENVKGAVWTVDEVEYQKRRSQKITGSPTLVKNIPTSL<br>GYGAALNASLQAALAESSLPLLSNPGLINNASSGLLQAVHEDL<br>NGSLDHIDSNGNSSPGCSPQPHIHSIHVKEEPVIAEDEDCPMS<br>LVTTANHSPELEDDREIEEEPLSEDLE | Exemplary wildtype human FoxP2 sequence NCBI Ref No. NP_055306.1 |
| 36 | MMVESASETIRSAPSGQNGVGSLSGQADGSSGGATGTTASGTG<br>REVTTGADSNGEMSPAELLHFQQQQALQVARQFLLQQASGLSS<br>PGNNDSKQSASAVQVPVSVAMMSPQMLTPQQMQQILSPPQLQA<br>LLQQQQALMLQQEYYKKQQEQLHLQLLTQQQAGKPQPKEALGN<br>KQLAFQQQLLQMQQLQQQHLLNLQRQGLVSLQPNQASGPLQTL<br>PQAAVCPTDLPQLWKGEGAPGQPAEDSVKQEGLDLTGTAATAT<br>SFAAPPKVSPPLSHHTLPNGQPTVLTSRRDSSSHEETPGSHPL<br>YGHGECKWPGCETLCEDLGQFIKHLNTEHALDDRSTAQCRVQM<br>QVVQQLEIQLAKESERLQAMMAHLHMRPSEPKPFSQPLNPVPG<br>SSSFSKVTVSAADSFPDGLVHPPTSAAAPVTPLRPPGLGSASL<br>HGGGPARRRSSDKFCSPISSELAQNHEFYKNADVRPPFTYASL<br>IRQAILETPDRQLTLNEIYNWFTRMFAYFRRNTATWKNAVRHN<br>LSLHKCFVRVENVKGAVWTVDEREYQKRRPPKMTGSPTLVKNM<br>ISGLSYGALNASYQAALAESSFPLLNSPGMLNPGSASSLLPLS<br>HDDVGAPVEPLPSNGSSSPPRLSPPQYSHQVQVKEEPAEAEED<br>RQPGPPLGAPNPSASGPPEDRDLEEELPGEELS | Exemplary wildtype human FoxP4 sequence GenBank: KJ900035.1 |
| 37 | aaagatagtacgttgtccgcag | FoxP3(P1) forward primer |
| 38 | atttgcaccctgcattgcgc | FoxP3(P1) reverse primer |
| 39 | tctgtgctgcctcgtgctcc | IL10 forward primer |
| 40 | tctgacagagcctggcaccc | IL10 reverse primer |

TABLE 1 -continued

Description of Certain Sequences

| SEQ ID NO: | SEQUENCE | DESCRIPTION |
|---|---|---|
| 41 | tccactcacggcaaattcaac | mGAPDH forward primer |
| 42 | cgctcctggaagatggtgatg | mGAPDH reverse primer |

DESCRIPTION OF CERTAIN EXEMPLARY EMBODIMENTS

The present disclosure provides NOX1 core promoters for regulating expression of transgenes in response to vascular pathology. In some embodiments, a NOX1 core promoter may express a transgene in a high-lipid environment or in the presence of factors associated with inflammation, such as Angiotensin II (Ang II), Lipopolysaccharides (LPS), or Oxidized Low Density Lipoprotein (Ox-LDL). A NOX1 core promoter of reduced size, such as a NOX1 core promoter comprising less than 600 nucleotides, allows for larger or multiple transgenes to be used in a single gene therapy vector having limited packaging capacity, such as AAV. For example, NOX1 core promoters within nucleotide positions 1561 and 1817 of SEQ ID NO: 1 are provided. A NOX1 core promoter may be modified, such as by removing an unnecessary ATG start site and/or adding a TATA box and/or a CAAT box. One or more transcription factor binding sites may also be added to an isolated nucleic acid molecule comprising a NOX1 core promoter, for example, at the 5' end of a NOX1 core promoter. NOX1 core promoters described herein may be useful in gene therapy methods for regulated expression of therapeutic proteins, such as anti-inflammatory molecules, for the treatment of vascular and/or inflammation-associated diseases.

The present disclosure further provides variant FOXP polypeptides having a zinc finger and leucine zipper region of a different FOXP polypeptide. Such variant FOXP polypeptides may preferentially dimerize with each other over the corresponding endogenous wildtype FOXP polypeptide. For example, a variant FOXP3 polypeptide having a zinc finger and leucine zipper region of FOXP1 (SEQ ID NO: 28) was designed and expressed. Variant FOXP3 polypeptides described herein may be useful for the treatment of vascular and/or inflammation-associated diseases.

Nucleic acids, vectors, and expression systems comprising a NOX1 core promoter and/or encoding variant FOXP3 polypeptides are also described. Further methods of expressing variant FOXP3 polypeptides, including regulated expression, by gene therapy methods are described. For example, several in vitro and in vivo animal studies are described involving transduction with AAV vectors delivering an exemplary NOX1 core promoter regulating expression of a reporter protein or multiple therapeutic proteins (e.g., an exemplary variant FOXP3 polypeptide and IL10).

An in vivo animal model of established and ongoing atherosclerosis for testing treatment options that more closely mimics the human clinical situation is also described. In some embodiments, low density lipoprotein receptor knockout (LDLR-KO) mice or rats are fed a high cholesterol diet (HCD) for a period of time, such as at least 56 days, before administering a therapeutic agent (e.g., a gene therapy vector expressing a therapeutic protein). An AAV vector delivering an exemplary NOX1 core promoter regulating expression of a variant FOXP3 polypeptide and IL10 was tested using this animal model. LDLR-KO mice maintained on a HCD and administered the eNOX1-FOXP3 (P1)-IL10 vector at week 12 showed significantly less vascular pathology when analyzed at week 20 by high-resolution ultrasound imaging compared to mice maintained on a HCD and administered a control vector.

For the convenience of the reader, the following definitions of terms used herein are provided.

As used herein, numerical terms are calculated based upon scientific measurements and, thus, are subject to appropriate measurement error. In some instances, a numerical term may include numerical values that are rounded to the nearest significant figure.

As used herein, "a" or "an" means "at least one" or "one or more" unless otherwise specified. As used herein, the term "or" means "and/or" unless specified otherwise. In the context of a multiple dependent claim, the use of "or" when referring back to other claims refers to those claims in the alternative only.

Exemplary Nucleic Acid Molecules and Polypeptides

"Nucleic acid molecule" or "polynucleotide" are used interchangeably herein to refer to a polymer of nucleotides. A nucleotide is composed of a base, specifically a purine or pyrimidine base (i.e., cytosine (C), guanine (G), adenine (A), thymine (T) or uracil (U)); a sugar (i.e., deoxyribose or ribose); and a phosphate group. A nucleic acid molecule may be described by the nucleotide sequence representing its primary linear structure. A nucleotide sequence is typically represented from 5' to 3'. Nucleic acid molecules include, for example, deoxyribonucleic acid (DNA) including genomic DNA, mitochondrial DNA, methylated DNA, and the like; ribonucleic acid (RNA), including messenger RNA (mRNA), small interfering RNA (siRNA), microRNA (miRNA), non-coding RNAs. A nucleic acid molecule can be single-stranded or double-stranded DNA or RNA. Alternatively, a nucleic acid molecule may be a DNA-RNA duplex.

A nucleotide base may be represented using the International Union of Pure and Applied Chemistry (IUPAC) nucleotide code shown in Table 2.

TABLE 2

| IUPAC nucleotide code | Base |
|---|---|
| A | Adenine |
| C | Cytosine |
| G | Guanine |
| T (or U) | Thymine (or Uracil) |
| R | A or G |
| Y | C or T |
| S | G or C |
| W | A or T |

TABLE 2-continued

| IUPAC nucleotide code | Base |
| --- | --- |
| K | G or T |
| M | A or C |
| B | C or G or T |
| D | A or G or T |
| H | A or C or T |
| V | A or C or G |
| N | any base |

A nucleic acid molecule or polypeptide described herein may be from any source unless otherwise indicated. The source may be a vertebrate source, including mammals such as primates (e.g., humans or cynomolgus monkeys), rodents (e.g., mice and rats), etc.

"Heterologous" as used herein, refers to a nucleic acid molecule or polypeptide that is foreign to its surrounding nucleic acid molecule or polypeptide.

"Promoter," as used herein, refers to a nucleic acid molecule comprising a nucleotide sequence upstream of a transcription start site that is capable of initiating transcription. A promoter may be a constitutive promoter or a regulated promoter.

A "constitutive promoter" is an unregulated promoter that allows for continual transcription. Non-limiting exemplary constitutive promoters include cytomegalovirus (CMV) immediate early promoter, simian virus 40 (SV40) early promoter, adenovirus major late promoter (MLP), Rous sarcoma virus (RSV) promoter, mouse mammary tumor virus (MMTV) promoter, phosphoglycerate kinase 1 (PGK) promoter, elongation factor-alpha (EF1a) promoter, ubiquitin promoters, actin promoters (such as human β-actin promoter and chicken β-actin promoter), chicken β-actin promoter and CMV early enhancer, tubulin promoters, immunoglobulin promoters, a functional fragment thereof, or a combination of any of the foregoing. In some embodiments, the promoter may be a CMV promoter. In some embodiments, the promoter may be a truncated CMV promoter. In other embodiments, the promoter may be an EF1a promoter.

Non-limiting exemplary regulated promoters include those inducible by or responsive to heat shock, light, chemicals, lipids, peptides, metals, steroids, antibiotics, or alcohol. A regulated promoter may be a pathology-specific promoter and/or a tissue-specific promoter. In some embodiments, a regulated promoter may be one that regulates expression of a transgene in the presence of one or more factors associated with inflammation, such as Ang II, LPS, Ox-LDL and/or carbamylated LDL. In some embodiments, the promoter is responsive to sheer stress. In some embodiments, the promoter is responsive to dyslipidemia.

A "pathology-specific promoter," as used herein, is a type of regulated promoter that is generally responsive to stimuli characteristic of a disease, condition, or disorder being treated. In some embodiments, a pathology-specific promoter may preferentially express a transgene in the presence of a high-lipid environment characteristic of a vascular pathology.

A "tissue-specific promoter," as used herein, is a type of regulated promoter that is generally responsive to stimuli characteristic of one or more cell types. In some embodiments, a tissue-specific promoter may preferentially express a transgene in liver cells. In some embodiments, a tissue-specific promoter may preferentially express a transgene in muscle cells. In some embodiments, a tissue-specific promoter may preferentially express a transgene in endothelial cells, such as vascular endothelial cells.

"Core promoter," as used herein, refers to a nucleic acid molecule comprising a smaller portion of a promoter nucleotide sequence that is capable of initiating transcription.

In some embodiments, a promoter or a core promoter comprises one or more transcription factor binding sites, a TATA box or TATA-like box, and/or one or more enhancer elements.

"Transcription factor binding site" or "binding site" as used interchangeably herein, refers to the region of a nucleic acid molecule to which a transcription factor binds. A transcription factor binding site may be described by the nucleotide sequence (e.g., a specific sequence or a consensus sequence) representing its primary linear structure.

"Consensus sequence," as used herein, refers to a sequence of frequent residues identified by sequence alignment of related sequences.

"NOX1 promoter," as used herein, refers to a nucleic acid molecule comprising a nucleotide sequence upstream of a transcription start site of a NADPH Oxidase 1 (NOX1) coding sequence from any source. The source may be a vertebrate source, including mammals such as primates (e.g., humans or cynomolgus monkeys), rodents (e.g., mice and rats), etc. For example, a human NOX1 promoter may comprise the nucleotide sequence of SEQ ID NO: 1 (a 2027 nucleotide sequence upstream of the ATG start site of the human NOX1 gene reported as GenBank Accession No. DQ314883.1).

"NOX1 core promoter," as used herein, refers to a smaller portion of a NOX1 promoter or variant thereof that is capable of initiating transcription. For example, a NOX1 core promoter may be less than 600 nucleotides, less than 550 nucleotides, less than 500 nucleotides, less than 480 nucleotides, or less than 470 nucleotides. In some embodiments, a NOX1 core promoter comprises a nucleotide sequence within nucleotide positions 1561 and 1817 of SEQ ID NO: 1.

"Variant NOX1 core promoter," as used herein, refers to a NOX1 core promoter that differs from a reference NOX1 core promoter by a single or multiple non-native nucleotide substitutions, deletions, and/or additions and retains the ability to initiate transcription. For example, a variant NOX1 core promoter may have one or more nucleotide substitutions, deletions, and/or additions that knocks out an unnecessary ATG start site, that adds a stop codon (e.g., TGA, TAA, or TAG), that adds a Kozak consensus sequence, and/or that adds a CAAT box.

A "point mutation," as used herein, refers to a mutation that involves a single nucleotide base or very few nucleotide bases of a nucleic acid molecule. For example, the mutation may be the loss of one base, substitution of one nucleotide base for another, or the insertion of an additional nucleotide base.

As used herein, "percent (%) amino acid sequence identity" and "homology" with respect to a nucleic acid molecule or a polypeptide are defined as the percentage of nucleotides or amino acid residues in a candidate sequence that are identical with the nucleotides or amino acid residues in the reference nucleic acid molecule or polypeptide, after aligning the sequences and introducing gaps, if necessary to achieve the maximum percent sequence identity, and not considering any conservative substitutions as part of the sequence identity. Alignment for purposes of determining percent sequence identity can be achieved in various ways that are within the skill in the art, for instance, using publicly available computer software such as BLAST, BLAST-2, ALIGN, or MEGALINE™ (DNASTAR) software. Those skilled in the art can determine appropriate parameters for measuring alignment, including any algorithms needed to achieve maximal alignment over the full length of sequences being compared.

In some embodiments, a nucleic acid molecule or a polypeptide has at least about 50% sequence identity with the reference nucleic acid molecule or polypeptide after aligning the sequences and introducing gaps, if necessary, to achieve the maximum percent sequence identity, and not considering any conservative substitutions as part of the sequence identity. A nucleic acid molecule may include, for instance, addition or deletion of one or more nucleic acid bases at the 5' or 3' terminus compared to a reference nucleic acid molecule. A polypeptide may include, for example, addition or deletion at the N- or C-terminus of the polypeptide compared to a reference polypeptide. In some embodiments, a nucleic acid molecule or a polypeptide has at least about 50% sequence identity, at least about 60% sequence identity, at least about 65% sequence identity, at least about 70% sequence identity, at least about 75% sequence identity, at least about 80% sequence identity, at least about 85% sequence identity, at least about 90% sequence identity, at least about 91% sequence identity, at least about 92% sequence identity, at least about 93% sequence identity, at least about 94% sequence identity, at least about 95% sequence identity, at least about 96% sequence identity, at least about 97% sequence identity, at least about 98% sequence identity, at least about 99% sequence identity, or 100% sequence identity with the sequence of a reference nucleic acid molecule or polypeptide.

In some embodiments, a NOX1 core promoter comprises a nucleotide sequence having at least 80%, at least 85%, at least 90%, at least 91%, at least 92%, at least 93%, at least 94%, at least 95%, at least 96%, at least 97%, at least 98%, at least 99%, or at least 100% sequence identity to SEQ ID NO: 2 or SEQ ID NO: 3. In some embodiments, a NOX1 core promoter comprises the nucleotide sequence of SEQ ID NO: 2 or SEQ ID NO: 3.

A NOX1 promoter or a NOX1 core promoter may naturally comprise one or more endogenous transcription factor binding sites.

In some embodiments, a NOX1 core promoter is modified to contain one or more heterologous transcription factor binding sites (e.g., one or more NFκB binding sites and/or one or more Oct1 binding sites) within the core promoter sequence. In some embodiments, a nucleic acid molecule comprising a NOX1 core promoter may further comprise at least one heterologous transcription factor binding site positioned at the 5' end or the 3' end of the NOX1 core promoter. For example, a nucleic acid molecule comprising a NOX1 core promoter may further comprise at least one NFκB binding site, which may be positioned at the 5' end or the 3' end of the NOX1 core promoter. In some embodiments, a nucleic acid molecule comprising a NOX1 core promoter may further comprise at least one Oct1 binding site, which may be positioned at the 5' end or the 3' end of the NOX1 core promoter.

In some embodiments, an NFκB binding site may be described by a specific sequence, such as, including but not limited to, the nucleotide sequence of SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, or SEQ ID NO: 20. An NFκB binding site may be described by a consensus sequence, such as, including but not limited to, the nucleotide sequence of SEQ ID NO: 5, SEQ ID NO: 6, SEQ ID NO: 7, SEQ ID NO: 8, SEQ ID NO: 9, SEQ ID NO: 10, or SEQ ID NO: 11. Exemplary NFκB binding sites are described in Wan F and Lenardo M, 2009; Wong D, et al., 2011; Kunsch C, et al., 1992; Udalova I A, et al., 2002; and Takano T and Cybulsky AV, 2000, each of which is incorporated herein by reference in their entirety.

In some embodiments, an Oct1 binding site may be described by the nucleotide sequence of SEQ ID NO: 21. See Jenuwein T and Grosschedl R, 1991; Chen J, BCJ, 2006; Zhao F Q, et al., 2013, each of which is incorporated herein by reference in their entirety.

In some embodiments, a nucleic acid molecule comprising a NOX1 core promoter comprises at least one, at least two, at least three, at least four, or at least five heterologous NFκB binding sites. In some embodiments, a nucleic acid molecule comprising a NOX1 core promoter comprises at least one, at least two, at least three, at least four, or at least five heterologous Oct1 binding sites. In some embodiments, a variant NOX1 core promoter comprises at least one, at least one, at least two, at least three, at least four, or at least five heterologous NFκB binding sites. In some embodiments, a variant NOX1 core promoter comprises at least one, at least one, at least two, at least three, at least four, or at least five heterologous Oct1 binding sites.

In some embodiments, a nucleic acid molecule comprises a nucleotide sequence having at least 80%, at least 85%, at least 90%, at least 91%, at least 92%, at least 93%, at least 94%, at least 95%, at least 96%, at least 97%, at least 98%, at least 99%, or at least 100% sequence identity to SEQ ID NO: 4. In some embodiments, a nucleic acid molecule comprises the nucleotide sequence of SEQ ID NO: 4.

"Transgene," as used herein refers to a nucleic acid molecule that encodes a product that may be useful in biotechnology and medicine, such as proteins and RNA. A transgene is generally represented by its nucleotide coding sequence. Exemplary proteins include enzymes, cytokines, receptors, and reporter proteins, etc. Exemplary RNA include sort hairpin RNA (shRNA), transfer RNA (tRNA), double stranded (dsRNA), ribosomal RNA, catalytic RNA, antisense RNA, messenger RNA (mRNA), small interfering RNA (siRNA), microRNA (miRNA), and non-coding RNAs.

A nucleotide coding sequence of a transgene can be operatively linked to regulatory components in a manner which permits transgene transcription, translation, and/or expression in a target cell. In some embodiments, the regulatory component comprises a NOX1 promoter, a NOX1 core promoter, or a variant NOX1 core promoter, as described herein. In some embodiments, an isolated nucleic acid molecule comprises a NOX1 core promoter or a variant NOX1 core promoter and a nucleotide sequence encoding a transgene, such as a reporter protein or a therapeutic polypeptide (e.g., an anti-inflammatory molecule).

In some embodiments, a transgene comprises a nucleotide coding sequence for a reporter protein, such as a FLAG-tag, a β-lactamase, a β-galactosidase (LacZ), an alkaline phosphatase, a thymidine kinase, a green fluorescent protein (GFP), a red fluorescent protein (RFP), such as mCherry, chloramphenicol acetyltransferase (CAT), luciferase, membrane bound proteins (e.g., CD2, CD4, CD8, the influenza hemagglutinin protein), and others well known in the art, to which high affinity antibodies directed thereto exist or can be produced by conventional means, and fusion proteins thereof. In some embodiments, a transgene comprises a nucleotide coding sequence for a FLAG-tag and mCherry fusion protein.

Such reporter proteins can provide signals detectable by conventional means, including enzymatic, radiographic, colorimetric, fluorescence or other spectrographic assays, fluorescent activating cell sorting (FACS) assays and immunological assays, including enzyme linked immunosorbent assay (ELISA), radioimmunoassay (MA) and immunohistochemistry. For example, where the marker sequence is the LacZ gene, the presence of the vector carrying the signal is detected by assays for beta-galactosidase activity. Where the reporter protein is mCherry or luciferase, the cell expressing the reporter protein may be measured visually by color or light production in a luminometer.

In some embodiments, the transgene comprises a nucleotide coding sequence for a therapeutic polypeptide. In some embodiments, a therapeutic polypeptide is an anti-inflammatory molecule.

"Amino acid sequence," means a sequence of amino acids residues in a polypeptide or protein. The terms "polypeptide" and "protein" are used interchangeably to refer to a polymer of amino acid residues, and are not limited to a minimum length. Such polymers of amino acid residues may contain natural or non-natural amino acid residues, and include, but are not limited to, peptides, oligopeptides, dimers, trimers, and multimers of amino acid residues. Both full-length proteins and fragments thereof are encompassed by the definition. The terms also include post-expression modifications of the polypeptide, for example, glycosylation, sialylation, acetylation, phosphorylation, and the like. Furthermore, for purposes of the present disclosure, a "polypeptide" refers to a protein which includes modifications, such as deletions, additions, and substitutions (generally conservative in nature), to the native sequence, as long as the protein maintains the desired activity. These modifications may be deliberate, as through site-directed mutagenesis, or may be accidental, such as through mutations of hosts which produce the proteins or errors due to PCR amplification.

An "amino acid substitution" refers to the replacement of one amino acid in a polypeptide with another amino acid. In some embodiments, an amino acid substitution is a conservative substitution. Nonlimiting exemplary conservative amino acid substitutions are shown in Table 3. Amino acid substitutions may be introduced into a molecule of interest and the products screened for a desired activity, for example, retained/improved antigen binding, decreased immunogenicity, improved recombinant production, and/or enhanced pharmacokinetics.

TABLE 3

| Original Residue | Exemplary Substitutions |
| --- | --- |
| Ala (A) | Val; Leu; Ile |
| Arg (R) | Lys; Gln; Asn |
| Asn (N) | Gln; His; Asp; Lys; Arg |
| Asp (D) | Glu; Asn |
| Cys (C) | Ser; Ala |
| Gln (Q) | Asn; Glu |
| Glu (E) | Asp; Gln |
| Gly (G) | Ala |
| His (H) | Asn; Gln; Lys; Arg |
| Ile (I) | Leu; Val; Met; Ala; Phe; Norleucine |
| Leu (L) | Norleucine; Ile; Val; Met; Ala; Phe |
| Lys (K) | Arg; Gln; Asn |
| Met (M) | Leu; Phe; Ile |
| Phe (F) | Trp; Leu; Val; Ile; Ala; Tyr |
| Pro (P) | Ala |
| Ser (S) | Thr |
| Thr (T) | Val; Ser |
| Trp (W) | Tyr; Phe |
| Tyr (Y) | Trp; Phe; Thr; Ser |

TABLE 3-continued

| Original Residue | Exemplary Substitutions |
| --- | --- |
| Val (V) | Ile; Leu; Met; Phe; Ala; Norleucine |

Amino acids may be grouped according to common side-chain properties
(1) hydrophobic: Norleucine, Met, Ala, Val, Leu, Ile;
(2) neutral hydrophilic: Cys, Ser, Thr, Asn, Gln;
(3) acidic: Asp, Glu;
(4) basic: His, Lys, Arg;
(5) residues that influence chain orientation: Gly, Pro;
(6) aromatic: Trp, Tyr, Phe.

Non-conservative substitutions will entail exchanging a member of one of these classes with another class.

"Wildtype polypeptide," as used herein, refers to a non-mutated version of a polypeptide that occurs in nature, or a fragment thereof. A wildtype polypeptide may be produced recombinantly.

"Variant polypeptide," as used herein, refers to a polypeptide that differs from a reference polypeptide by a single or multiple non-native amino acid substitutions, deletions, and/or additions. In some embodiments, a variant polypeptide retains at least one biological activity of the reference polypeptide (e.g., a corresponding wildtype polypeptide). A variant polypeptide includes, for instance, polypeptides wherein one or more amino acid residues are added, deleted, at the N- or C-terminus of the polypeptide.

"FOXP" and "FOXP polypeptide," as used interchangeably herein, refer to a polypeptide comprising the entirety or a fragment of a protein from the Forkhead box protein family (such as FOXP1, FOXP2, FOXP3, or FOXP4) from any vertebrate source, including mammals such as primates (e.g., humans and cynomolgus monkeys), rodents (e.g., mice and rats), and companion animals (e.g., dogs, cats, and equine), unless otherwise indicated. FOXP includes variant FOXP polypeptides that substantially retain at least one biological activity of a wildtype FOXP polypeptide.

A "variant FOXP polypeptide" as used herein is a FOXP polypeptide that differs from a reference FOXP polypeptide by single or multiple amino acid substitutions, deletions, and/or additions and substantially retains at least one biological activity of the reference FOXP3 polypeptide.

In some embodiments, FOXP may be a wildtype FOXP1, FOXP2, FOXP3, or FOXP4 polypeptide. An exemplary wildtype human FOXP1 comprises the amino acid of SEQ ID NO: 26. An exemplary wildtype human FOXP2 comprises the amino acid of SEQ ID NO: 35. An exemplary wildtype human FOXP3 comprises the amino acid of SEQ ID NO: 24. An exemplary wildtype human FOXP4 comprises the amino acid of SEQ ID NO: 36.

Wildtype FOXP polypeptides have a zinc finger and leucine zipper region understood to be involved in protein dimerization. Kim J, et al., 2019; Wang B, et al., 2003; Song Z, et al., 2012. "Zinc finger and leucine zipper region," as used herein, refers to a region of a polypeptide comprising a zinc finger motif and a leucine zipper motif. In some embodiments, a zinc finger and leucine zipper region of a FOXP3 polypeptide comprises the amino acid sequence of SEQ ID NO: 25. In some embodiments, a zinc finger and leucine zipper region of a FOXP3 polypeptide comprises an amino acid sequence within amino acid positions 225 and 264 of SEQ ID NO: 24. In some embodiments, a zinc finger and leucine zipper region of a FOXP1 polypeptide comprises the amino acid sequence of SEQ ID NO: 27. In some embodiments, a zinc finger and leucine zipper region of a FOXP1 polypeptide comprises an amino acid sequence within amino acid positions 146 and 185 of SEQ ID NO: 26.

In some embodiments, a variant FOXP polypeptide comprises the amino acid sequence of a first FOXP polypeptide, wherein a zinc finger and leucine zipper region of the first FOXP polypeptide has been replaced with a zinc finger and leucine zipper region of a second FOXP polypeptide. In some embodiments, the first FOXP polypeptide is a FOXP1 polypeptide and the second FOXP polypeptide is a FOXP2, FOXP3, or FOXP4 polypeptide. In some embodiments, the first FOXP polypeptide is a FOXP2 polypeptide and the second FOXP polypeptide is a FOXP1, FOXP3, or FOXP4 polypeptide. In some embodiments, the first FOXP polypeptide is a FOXP3 polypeptide and the second FOXP polypeptide is a FOXP1, FOXP2, or FOXP4 polypeptide. In some embodiments, the first FOXP polypeptide is a FOXP4 polypeptide and the second FOXP polypeptide is a FOXP1, FOXP2, or FOXP3 polypeptide. In some embodiments, the first FOXP polypeptide is a FOXP3 polypeptide and the second FOXP polypeptide is a FOXP1 polypeptide. In some embodiments, the first FOXP polypeptide is a FOXP1 polypeptide and the second FOXP polypeptide is a FOXP3 polypeptide.

In some embodiments, a variant FOXP polypeptide comprises an amino acid sequence having at least 97%, at least 98%, at least 99%, or 100% sequence identity to the amino acid sequence of SEQ ID NO: 28. In some embodiments, a variant FOXP polypeptide comprises an amino acid sequence of SEQ ID NO: 28.

Also embodied in the present disclosure are nucleic acid molecules comprising a nucleotide coding sequence for the variant FOXP polypeptides described herein. Given that the genetic code is well-known in the art, it is routine for one of ordinary skill in the art to generate such degenerate nucleic acid molecules that encode transgenes, including the variant FOXP polypeptides of the present disclosure. For example, an isolated nucleic acid molecule may comprise a nucleic acid sequence encoding any one of the variant FOXP polypeptides described herein, including those referred to in the above paragraphs. In some embodiments, an isolated nucleic acid comprises the nucleotide sequence of SEQ ID NO: 29.

In some embodiments, an isolated nucleic acid molecule comprises a NOX1 core promoter or a variant NOX1 core promoter and a wildtype or variant FOXP3 polypeptide. In some embodiments, an isolated nucleic acid molecule comprises a NOX1 core promoter or a variant NOX1 core promoter and IL10. In some embodiments, an isolated nucleic acid molecule comprises a NOX1 core promoter or a variant NOX1 core promoter and a wildtype or variant FOXP3 polypeptide and IL10. In some embodiments, an isolated nucleic acid comprises the nucleotide sequence of SEQ ID NO: 34.

Exemplary Vectors

As used herein, "vector" includes any genetic element, including, but not limited to, a plasmid, phage, transposon, cosmid, chromosome, artificial chromosome, minichromosome, expression vector, virus, virion, etc., which is capable of replication when associated with the proper control elements and which can transfer nucleic acid molecules to cells. The term includes cloning and expression vectors, as well as viral vectors.

In some embodiments, one or more of the vectors, or all of the vectors, may be DNA vectors. In some embodiments, one or more of the vectors, or all of the vectors, may be RNA vectors. In some embodiments, one or more of the vectors, or all of the vectors, may be circular. In other embodiments, one or more of the vectors, or all of the vectors, may be linear. In some embodiments, one or more of the vectors, or all of the vectors, may be enclosed in a lipid nanoparticle, liposome, non-lipid nanoparticle, or viral capsid.

Non-limiting exemplary viral vectors include adeno-associated virus (AAV) vector, lentivirus vectors, adenovirus vectors, helper-dependent adenoviral vectors (HDAd), herpes simplex virus (HSV-1) vectors, bacteriophage T4, baculovirus vectors, pox virus vectors, and retrovirus vectors. In some embodiments, the viral vector may be an AAV vector. In other embodiments, the viral vector may a lentivirus vector. In some embodiments, the lentivirus may be non-integrating. In some embodiments, the viral vector may be an adenovirus vector. In yet other embodiments, the viral vector may be an HSV-1 vector. In some embodiments, the HSV-1-based vector is helper dependent, and in other embodiments it is helper independent. In additional embodiments, the viral vector may be bacteriophage T4. In further embodiments, the viral vector may be a baculovirus vector. In yet further embodiments, the viral vector may be a retrovirus vector.

An AAV vector may comprise a nucleic acid molecule enclosed in an AAV viral capsid. The encapsidated nucleic acid molecule may comprise AAV inverted terminal repeats (ITRs) positioned at each termini. AAV ITRs may be derived from any number of AAV serotypes, including AAV2. AAV ITRs can form hairpin structures and are involved in AAV proviral integration and vector packaging. An AAV vector may comprise a capsid protein from any one of the AAV serotypes, including, but not limited to AAV1, AAV2, AAV3, AAV4, AAV5, AAV6, AAV7, AAV8, AAV9, AAV10, AAV11, AAV12, AAV13, and variant capsids based on any serotype modified to target a specific cell type. In some embodiments, an AAV vector comprises a nucleic acid molecule with AAV2 ITRs and enclosed in an AAV8 viral capsid.

AAV vectors may be prepared using any one of the number of methods available to those of ordinary skill in the art. Hermonat P L, et al., 1984b; Liu Y, et al., 2001; Grimm D, et al., 1998; Neyns B, et al., 2001; Cecchini S, et al., 2011.

In some embodiments, a vector comprises a nucleic acid molecule comprising a nucleic acid molecule encoding a transgene that is operatively linked to a promoter. The phrases "operatively positioned," "operatively linked," "under control," or "under transcriptional control" means that a promoter is in the correct location and orientation in relation to the nucleic acid molecule to control RNA polymerase initiation and expression of the transgene.

In some embodiments, a vector may comprise one copy of a nucleotide sequence encoding a transgene. In other embodiments, the vector system may comprise more than one copy of a nucleotide sequence encoding a transgene. In some embodiments, a vector may comprise one or more nucleotide sequences encoding one or more transgenes. In some embodiments, a vector comprises a nucleic acid molecule encoding multiple transgenes. In some embodiments, a vector comprises a nucleic acid molecule encoding two transgenes. In some embodiments, a vector comprises a nucleic acid molecule encoding three transgenes.

In some embodiments, the vector may be capable of driving expression of one or more coding sequences, such as the coding sequence of a transgene disclosed herein, in a host cell, either in vivo, ex vivo, or in vitro. In some embodiments, the host cell is a eukaryotic cell, such as, e.g., a yeast, plant, insect, or mammalian cell. In some embodiments, the host cell is a mammalian cell. In some embodiments, the host cell is a rodent cell. In some embodiments, the host cell is a human cell. In some embodiments, the host cell is a smooth muscle cell, a cardiac muscle cell, a fibroblast cell, an immune cell (e.g., a macrophage, a T-cell, or a B-cell).

In some embodiments, a vector comprises a NOX1 core promoter or a variant NOX1 core promoter as disclosed herein. In some embodiments, a vector comprises a nucleic acid molecule encoding a wildtype FOXP polypeptide or variant FOXP3 polypeptide operably linked to a NOX1 core promoter or a variant NOX1 core promoter. In some embodiments, a vector comprises a nucleic acid molecule encoding a variant FOXP3 polypeptide operably linked to a promoter. In some embodiments, a vector comprises a nucleic acid molecule encoding a variant FOXP3 polypeptide operably linked to a regulated promoter. In some embodiments, a vector comprises a nucleic acid molecule encoding a variant FOXP3 polypeptide operably linked to a pathology-specific promoter. In some embodiments, a vector comprises a nucleic acid molecule encoding a variant FOXP3 polypeptide operably linked to a NOX1 core promoter. In some embodiments, a vector comprises a nucleic acid molecule encoding a variant FOXP3 polypeptide operably linked to a variant NOX1 core promoter.

In some embodiments, a vector comprises a nucleic acid molecule comprising the nucleotide sequence of SEQ ID NO: 3. In some embodiments, a vector comprises a nucleic acid molecule comprising at least 80%, at least 85%, at least 90%, at least 91%, at least 92%, at least 93%, at least 94%, at least 95%, at least 96%, at least 97%, at least 98%, or at least 99% sequence identity to the nucleotide sequence of SEQ ID NO: 3. In some embodiments, a vector comprises a nucleic acid molecule comprising the nucleotide sequence of SEQ ID NO: 4. In some embodiments, a vector comprises a nucleic acid molecule comprising at least 80%, at least 85%, at least 90%, at least 91%, at least 92%, at least 93%, at least 94%, at least 95%, at least 96%, at least 97%, at least 98%, or at least 99% sequence identity to the nucleotide sequence of SEQ ID NO: 4.

In some embodiments, a vector comprises a nucleic acid molecule encoding a variant FOXP3 polypeptide comprising the amino acid sequence of SEQ ID NO: 28. In some embodiments, a vector comprises a nucleic acid molecule comprising the nucleotide sequence of SEQ ID NO: 29. In some embodiments, a vector comprises a nucleic acid molecule comprising the nucleotide sequence of SEQ ID NO: 34.

In some embodiments, a vector comprises a nucleic acid molecule encoding a reporter protein operably linked to a NOX1 core promoter or a variant NOX1 core promoter. In some embodiments, a vector comprises a nucleic acid molecule encoding mCherry operably linked to a NOX1 core promoter or a variant NOX1 core promoter. In some embodiments, a vector comprises a nucleic acid molecule comprising the nucleotide sequence of SEQ ID NO: 22.

Exemplary Therapeutic Testing Model of Established and Ongoing Atherosclerosis

An in vivo animal model of established and ongoing atherosclerosis for testing treatment options that more closely mimics the human clinical situation is also described.

In some embodiments, a low density lipoprotein receptor knockout (LDLR-KO) or Apo E knockout mice or rat is fed a high cholesterol diet (HCD) for a period of time, such as at least 56 days, before administering a therapeutic agent (e.g., a gene therapy vector expressing a therapeutic protein).

LDLR-KO mice fed a HCD develop vascular pathology, including immune cell arterial influx, smooth muscle cell proliferation, and atherosclerotic plaque formation. Getz G S and Reardon C A, 2005; Li D, et al., 2006; Liu Y, et al., 2005; Pan J H, et al., 2004; Chen J, et al., 2018.

A "high cholesterol diet" or "HCD" includes any natural or synthetic fat, such as lard, cocoa butter, cholate, etc. Exemplary HCDs are commercially available (see, e.g., criver.com/products-services/research-models-services/pre-conditioning-services/custom-diets?region=3611; dyets-.com/experimental-diets/) and described in the literature (see, e.g., Zadelaar S, et al., 2007). In some embodiments, a HCD may comprise at least about 0.1%, at least 0.15%, at least 0.2%, at least 0.4%, at least 0.5%, at least 1%, at least 1.25%, at least 1.5%, at least 2%, at least 2.5%, at least 3%, at least 3.5%, at least 4%, at least 4.5%, at least about 5% cholesterol. In some embodiments, a HCD comprises between 0.1% and 5% cholesterol. In some embodiments, a HCD comprises between 1 and 15% cocoa butter. In some embodiments, a HCD comprises 4% cholesterol and 10% cocoa butter.

In some embodiments, a method for screening a therapeutic agent comprises maintaining an LDLR-KO or Apo E knockout animal on a HCD and administering a therapeutic agent to the animal no earlier than 56 days after beginning the HCD. In some embodiments, the therapeutic agent is administered no earlier than 63 days after beginning the high cholesterol diet. In some embodiments, the therapeutic agent is administered no earlier than 63 days after beginning the high cholesterol diet. In some embodiments, the therapeutic agent is administered no earlier than 70 days after beginning the high cholesterol diet. In some embodiments, the therapeutic agent is administered no earlier than 77 days after beginning the high cholesterol diet. In some embodiments, the therapeutic agent is administered no earlier than 84 days after beginning the high cholesterol diet. In some embodiments, the therapeutic agent is administered no earlier than 91 days after beginning the high cholesterol diet. In some embodiments, the therapeutic agent is administered no earlier than 98 days after beginning the high cholesterol diet.

In some embodiments, the blood flow velocity, cross-sectional area of the aorta lumen, and/or the aortic wall thickness of the animal are assessed by ultrasound imaging. Exemplary methods for high ultrasound imaging are described in Example 8.

Exemplary Pharmaceutical Compositions and Uses

"Pharmaceutical composition" refers to a preparation which is in such form as to permit administration of a therapeutic agent and other component(s) contained therein to a subject and does not contain components that are unacceptably toxic to a subject.

A "pharmaceutically acceptable carrier" refers to a non-toxic solid, semisolid, or liquid filler, diluent, encapsulating material, formulation auxiliary, or carrier conventional in the art for use with a therapeutic agent that together comprise a "pharmaceutical composition" for administration to a subject. A pharmaceutically acceptable carrier is non-toxic to recipients at the dosages and concentrations employed and is compatible with other ingredients of the formulation. The pharmaceutically acceptable carrier is appropriate for the formulation employed. A pharmaceutical composition may be in the form of solid, semisolid, liquid, cream, gel, capsule, or patch. The pharmaceutical composition may be in a form that allows for slow release or delayed release of a therapeutic agent.

Examples of pharmaceutically acceptable carriers include alumina; aluminum stearate; lecithin; serum proteins, such as human serum albumin, canine or other animal albumin; buffers such as phosphate, citrate, tromethamine or HEPES buffers; glycine; sorbic acid; potassium sorbate; partial glyceride mixtures of saturated vegetable fatty acids; water; salts or electrolytes, such as protamine sulfate, disodium hydrogen phosphate, potassium hydrogen phosphate, sodium chloride, zinc salts, colloidal silica, or magnesium trisilicate; polyvinyl pyrrolidone, cellulose-based substances; polyethylene glycol; sucrose; mannitol; or amino acids including, but not limited to, arginine.

"Therapeutic agent," as used herein, refers to an agent used for the treatment or prevention of a disease, condition, or disorder. A therapeutic agent may include a nucleic acid molecule, polypeptide, vector, and/or cell disclosed herein.

The pH of a pharmaceutical composition is typically in the range of from about pH 6 to pH 8 when administered, for example about 6, about 6.2, about 6.4, about 6.6, about 6.8, about 7, about 7.2. Pharmaceutical compositions may be sterilized if they are to be used for therapeutic purposes. Sterility can be achieved by any of several means known in the art, including by filtration through sterile filtration membranes (e.g., 0.2 micron membranes). Sterility may be maintained with or without anti-bacterial agents.

In some embodiments, a nucleic acid molecule, polypeptide, vector, cell, and/or pharmaceutical composition disclosed herein can be utilized in accordance with the methods herein to treat a vascular disease, a cardiovascular disease, atherosclerosis, an inflammation-associated disease, an age-associated disease, arthritis, and/or dementia.

In some embodiments, a nucleic acid molecule, a polypeptide, a vector, a cell, and/or a pharmaceutical composition disclosed herein are used for treating a subject having a vascular disease and/or a cardiovascular disease. Exemplary forms of vascular or cardiovascular disease include, but are not limited to, general atherosclerosis; plaque formation; cholesterol accumulation; stenosis; restenosis; hypertension; peripheral artery disease; peripheral artery disease of the legs; peripheral artery disease of the arms; peripheral artery disease of the gut/mesentery; disease of the carotid arteries; heart failure; cellular proliferation of smooth muscle; stroke; cardiac disease (e.g., risk stratification of chest pain and interventional procedures); pulmonary circulatory disease; graft occlusion or failure; need for or an adverse clinical outcome after peripheral bypass graft surgery; Paget-Schroetter disease; Budd-Chiari syndrome; peripheral vascular disease; renal atherosclerosis; renal vein thrombosis; jugular vein thrombosis; arterial disease of the aorta; carotid artery disease; coronary artery disease; coronary heart disease; pulmonary circulatory disease; correction of adverse clinical outcome after surgery for coronary artery bypass (CABG); pulmonary embolism; ischemic diseases; multiplicity of other cardiovascular disease related to obesity or an overweight condition; thrombosis formation (e.g., venous thrombosis, deep vein thrombosis, portal vein thrombosis, cerebral venous sinus thrombosis, or arterial thrombosis) or other thrombotic events or complications; myocardial infarction; graft failure; vein graft failure; vein graft occlusion; autologous vein grafts; coronary revascularization; kidney failure; cerebrovascular disease; ischemia reperfusion injury; general ischemia; heart disease; cardiopulmonary resuscitation; myocardial infection; treatment of adverse outcome after angioplasty; endothelial dysfunction; impaired general circulation; and left ventricular hypertrophy-acute coronary syndrome. A subject may have multiple forms of a vascular or cardiovascular disease.

In some embodiments, a nucleic acid molecule, a polypeptide, a vector, a cell, and/or a pharmaceutical composition disclosed herein are used for treating a subject having atherosclerosis.

In some embodiments, a nucleic acid molecule, a polypeptide, a vector, a cell, and/or a pharmaceutical composition disclosed herein are used for treating a subject having an inflammation-associated disease. In some embodiments, a nucleic acid molecule, a polypeptide, a vector, a cell, and/or a pharmaceutical composition disclosed herein are used for treating a subject having an age-associated disease. In some embodiments, a nucleic acid molecule, a polypeptide, a vector, a cell, and/or a pharmaceutical composition disclosed herein are used for treating a subject having arthritis, such as psoriatic arthritis, rheumatoid arthritis, or gouty arthritis. In some embodiments, a nucleic acid molecule, a polypeptide, a vector, a cell, and/or a pharmaceutical composition disclosed herein are used for treating a subject having asthma. In some embodiments, a nucleic acid molecule, a polypeptide, a vector, a cell, and/or a pharmaceutical composition disclosed herein are used for treating a subject having macular degeneration of the retina. In some embodiments, a nucleic acid molecule, a polypeptide, a vector, a cell, and/or a pharmaceutical composition disclosed herein are used for treating a subject having diabetes mellitus.

In some embodiments, a nucleic acid molecule, a polypeptide, a vector, a cell, and/or a pharmaceutical composition disclosed herein are used for treating a subject having dementia. Exemplary forms of dementia include, but are not limited to, Alzheimer's disease, dementia with Lewy bodies, vascular dementia, and frontotemporal dementia. A subject may have multiple forms of dementia, such as Alzheimer's disease and vascular dementia.

Methods for administering a nucleic acid molecule, a polypeptide, a vector, a cell, and/or a pharmaceutical composition disclosed herein include, but are not limited to, administering a therapeutically effective dose of a nucleic acid molecule, polypeptide, vector, cells, and/or pharmaceutical composition of the disclosure to a subject.

As used herein, "subject," "individual," and "patient," are used interchangeably to refer to an individual organism, a vertebrate, a mammal, or a human. In some embodiments, "subject" means any animal (mammal, human, or other) patient that can be afflicted with one or more of the diseases, conditions, or disorders described herein and is in need of treatment.

As used herein, "treat" and other forms of the term, including "treating," "treated, and "treatment," relate to an approach for obtaining beneficial or desired clinical results. Treatment covers any administration or application of a therapeutic agent for a disease, condition, or disorder in a subject, including a human subject. For purposes of this disclosure, beneficial or desired clinical results include, but are not limited to, any one or more of: alleviation of one or more symptoms; diminishment of extent of a disease, condition, or disorder; preventing or delaying spread of a disease, condition, or disorder; preventing or delaying recurrence of disease, condition, or disorder; amelioration of the state of the disease, condition, or disorder; inhibiting or slowing the progression of a disease, condition, or disorder or arresting its development; and remission (whether partial or total) of a disease, condition, or disorder. Also, encompassed by "treatment" is a reduction of pathological consequence of a proliferative disease. The methods provided herein contemplate any one or more of these aspects of treatment. In-line with the above, the term treatment does not require one-hundred percent removal of all aspects of a disease, condition, or disorder.

A "therapeutically effective amount" of a therapeutic agent may vary according to factors such as the type of disease to be treated, the disease state, the severity and course of the disease, the type of therapeutic purpose, any previous therapy, the clinical history, the response to prior treatment, the discretion of the attending physician, age, sex, and weight of the subject, and the ability of the therapeutic agent to elicit a desired response in the subject. A therapeutically effective amount is also one in which any toxic or detrimental effects of the therapeutic agent are outweighed by the therapeutically beneficial effects. A therapeutically effective amount may be delivered in one or more administrations. A therapeutically effective amount refers to an amount effective, at dosages and for periods of time necessary, to achieve the desired therapeutic or prophylactic result.

While the attending physician ultimately will decide the appropriate amount and dosage regimen, a therapeutically effective amount of a therapeutic agent of the disclosure can be provided. For example, a therapeutically effective amount of a polypeptide of the disclosure may be administered at a dose of 0.0001, 0.01, 0.01 0.1, 1, 5, 10, 25, 50, 100, 500, or 1,000 mg/kg. In some embodiments, a therapeutically effective amount of a vector of the disclosure may be administered at a dose of $1 \times 10^{10}$, $1 \times 10^{11}$, $1 \times 10^{12}$, or $1 \times 10^{13}$ viral particles (e.g., encapsidated genomes (eg)). In some embodiments, a therapeutically effective amount of a vector of the disclosure may be administered at a dose of $1 \times 10^{10}$ to $1 \times 10^{13}$ viral particles, $1 \times 10^{10}$ to $1 \times 10^{12}$ viral particles, or $1 \times 10^{10}$ to $1 \times 10^{11}$ viral particles. Effective doses may be extrapolated from dose-response curves derived from in vitro or animal model test bioassays or systems. For example, a therapeutically effective amount can be estimated initially either in cell culture assays or in animal models, usually mice, rabbits, dogs, or pigs. The animal model is also used to achieve a desirable concentration range and route of administration. Such information can then be used to determine useful doses and routes for administration in other subjects. Generally, the therapeutically effective amount is dependent of the desired therapeutic effect. For example, the therapeutically effective amount of a vector of the disclosure can be assessed in a mouse model of atherosclerosis.

A nucleic acid molecule, polypeptide, vector, cells, and/or pharmaceutical composition of the disclosure can be administered by any one or more routes known in the art or described herein, for example, orally (e.g., in capsules, suspensions or tablets), parenterally (e.g., intravenously or intramuscularly by solution, suspension, emulsion, or gel), intraperitoneal, rectal, cutaneous, nasal, vaginal, inhalant, skin (patch), and/or ocular. The nucleic acid molecule, polypeptide, vector, cells, and/or pharmaceutical composition of the disclosure may be administered in any dose or dosing regimen. In some cases, administration may be accomplished by an ex vivo route. Ex vivo delivery involves ex vivo (outside the body) transduction of host cells (e.g., smooth muscle cells, cardiac muscle cells, fibroblast cells, immune cells such as macrophages, T-cells, and/or B-cells) by recombinant vectors, followed by administration of the transduced cells to the subject. For example, host cells may be obtained from a subject, transduced outside the body by a vector of the disclosure, and then administered to the same subject or a different subject.

In some embodiments, a nucleic acid molecule, polypeptide, vector, cells, and/or pharmaceutical composition of the disclosure is administered parenterally, by subcutaneous administration, intravenous infusion, arterial injection, intramuscular injection, or injection into a section of a ligated artery or vein, or a combination thereof. Ligation of an artery or vein may be accomplished by any method understood by a person of ordinary skill in the art, such as by tying or clamping off a section of a vessel or artery (distal and proximal) so as to isolate the section from blood flow for a period of time. In some embodiments, a pharmaceutical composition in the form of a gel or cream and comprising the nucleic acid molecule, polypeptide, vector, and/or cells of the disclosure is applied to one or more locations of interest (e.g., an artery, vein, joint, etc.). In some embodiments, such a gel or cream may allow for slow release or delayed release of the therapeutic agent. In some embodiments, a nucleic acid molecule, polypeptide, vector, cells, and/or pharmaceutical composition of the disclosure is administered as a bolus injection or by infusion over a period of time.

In some embodiments, a therapeutic agent is administered once in a single dose or in multiple doses. When multiple doses are administered, the doses may be separated from one another by, for example, one hour, three hours, six hours, eight hours, one day, two days, one week, two weeks, or one month. In some embodiments, a therapeutic agent is administered every other day, once a week, or once a month. In some embodiments, a therapeutic agent is administered for, e.g., 2, 3, 4, 5, 6, 7, 8, 10, 15, 20, or more weeks. It is to be understood that, for any particular subject, specific dosage regimes should be adjusted over time according to the individual need and the professional judgment of the person administering or supervising the administration of the compositions. For example, the dosage of the therapeutic can be increased if the lower dose does not provide sufficient therapeutic activity.

In some embodiments, when a polypeptide encoded by a vector of the disclosure is expressed in a subject, the expression level can be constant over a desired period of time, for example, at least 1 week, at least 2 weeks, at least 3 weeks, at least 1 month, at least 2 months, at least 3 months, at least 6 months, at least 1 year, or at least 5 years. In some embodiments, the expression of a polypeptide disclosed herein can be sustained at or above a therapeutically effective dosage level over a desired period of time.

In some embodiments, the amount of therapeutic agent is administered to a subject (in pulses, as continuous treatment or as a one-time administration (e.g., via gene therapy expression of a polypeptide disclosed herein)) such that the blood levels of the polypeptide in the treated subject are above about 20%, or above about 30%, or above about 40%, or above about 50%, or between about 50-100% or above about 2-fold, or above about 3-fold, or above about 4-fold, or above about 5-fold or more than 5-fold the blood levels of the endogenous polypeptide in a control subject.

EXAMPLES

Example 1

Analysis of TGFβ and IL10 Expression in A7R5 Rat Smooth Muscle Cells Expressing FOXP3

FOXP3 is a master transcription factor of the regulatory pathway in the development and function of regulatory T cells (Treg cells), which are specialized T cells that act to suppress immune response. Loss of FOXP3 expression results in increased chronic autoimmunity. Ziegler S, 2006. Expression of FOXP3 is generally understood to be restricted to Treg cells. Karagiannidis C, et al., 2004; Fontenot J D, et al., 2003; Hori S, et al., 2003; Khattri R, et al., 2003; Li Z, et al., 2015; Kitoh A, et al., 2009. Hence, downstream effects of FOXP3 expression in other cell types, such as vascular smooth muscle cells, which are a target cell type in AAV treatment of atherosclerosis is unclear.

For example, expression levels of TGFβ and IL10 in immortal tissue culture A7R5 rat smooth muscle cells expressing FOXP3 was tested. The A7R5 cells were co-transfected with pSV40-Neo and CMV-FoxP3 expression plasmids at a 1:10 ratio and clones were selected with G418. G418-selected cell lines were tested for FOXP3 expression by Quantitative RT-PCR (Q-RT-PCR) for FOXP3 mRNA and compared to negative controls (untransfected A7R5 cells (labeled "A7R5") and A7R5 cells transfected with pSV40-Neo only and G418-selected (labeled "neo")) (FIG. 1A).

Figure 1B:
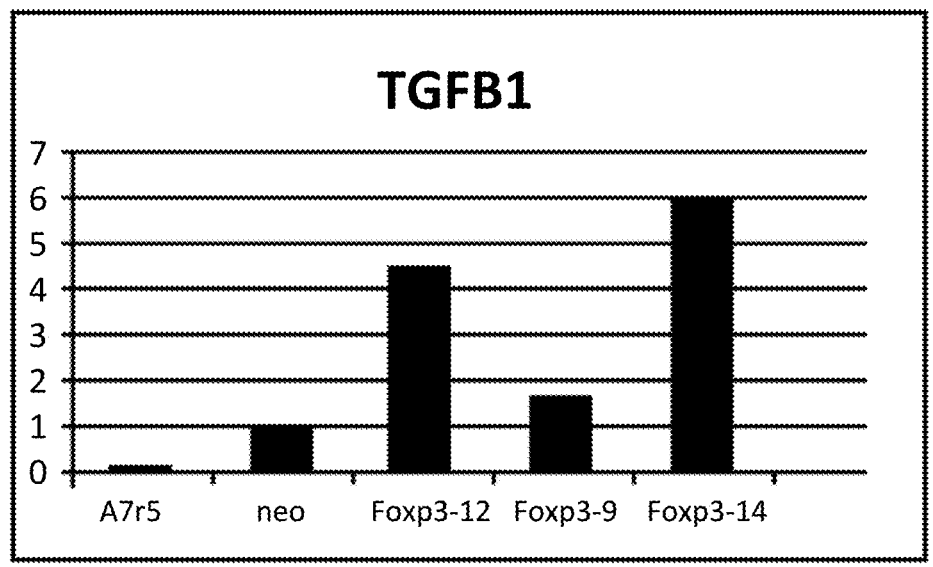
FIG. 1B shows expression levels of TGFβ by Q-RT-PCR in A7R5 rat smooth muscle cells expressing FOXP3.
Figure 1C:
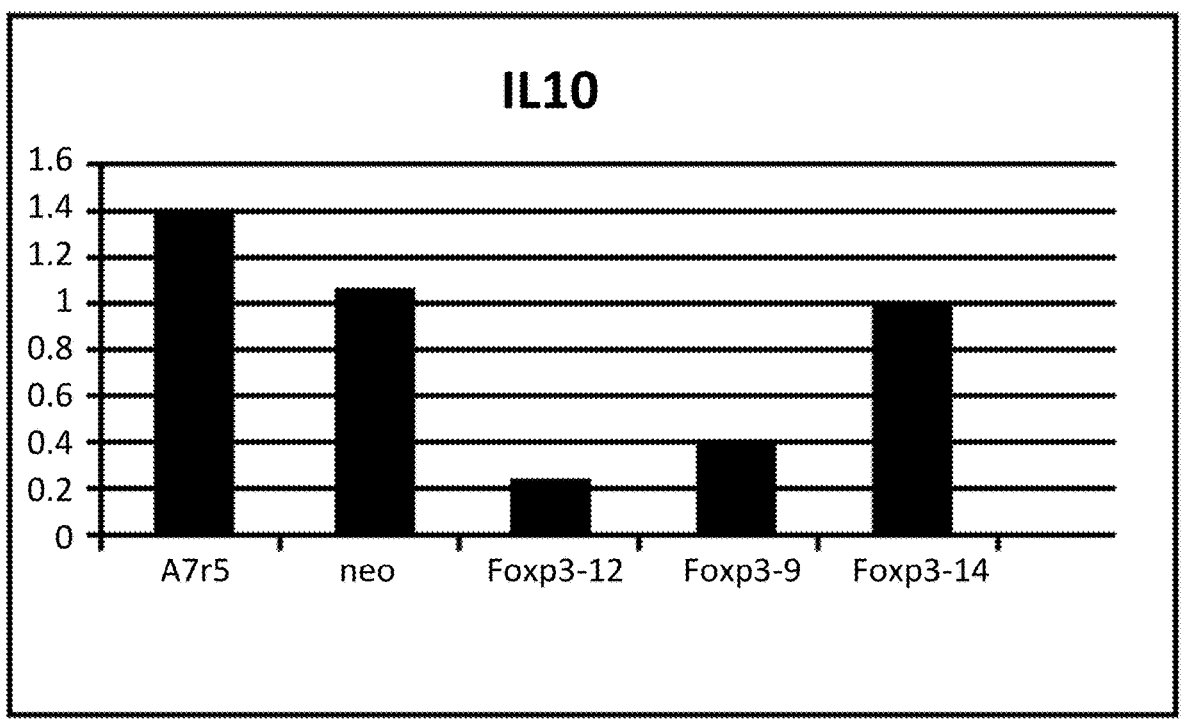
FIG. 1C shows expression levels of IL10 by Q-RT-PCR in A7R5 rat smooth muscle cells expressing FOXP3.

Relative expression of TGFβ and IL10 in select FOXP3-expressing clones was also measured by Q-RT-PCR for TGFβ and IL10 mRNA (FIG. 1B and FIG. 1C, respectively) and compared to the same negative controls ("A7R5" and "neo"). While an increase in TGFβ expression was observed with some FOXP3-expressing clones, IL10 expression did not appear to be induced by FOXP3 expression.

Example 2

Exemplary Core NOX1 Promoter

Constitutive or systemic expression of anti-inflammatory proteins, such as FOXP3, IL10, or TGFβ may not be desirable. For example, systemically expressed or high circulating levels of IL10 has been associated with increased bacterial and viral infections. Filippi C M and von Herrath M G, 2008; Zobel K, et al., 2012; Clemons K V, et al., 2000; Brooks D G, et al., 2008; Brooks D G, et al., 2006; Ejrnaes M, et al., 2006; Zeni E, et al., 2007; Maris C H, et al., 2007; Asadullah K, et al., 2003. In addition, many promoters used in gene therapy, including regulatable promoters, are problematic due to their large size and the limited packaging capacity of AAV. For example, the LOX1 high-lipid regulatable promoter (~2,400 bp) is too large for regulating multiple gene products in the context of AAV. When the LOX1 promoter is used, only 2 kb of AAV packaging capacity remains available for transgenes.

Expression of NOX1 is understood to be upregulated in response to shear stress, high lipids, and other irritating challenging agents, such as interferon gamma (IFN-γ) and Angiotensin-2 (Ang II). Hwang J, et al., 2003; Hsieh J H, et al., 2014; Valente A J, et al., 2007; Kuwano Y, et al., 2005; Nguyen Dinh Cat A, et al., 2012; Manea A., et al., 2009.

An exemplary NOX1 promoter having enhanced features (SEQ ID NO: 4; "eNOX1 promoter") comprising a variant NOX1 core promoter (SEQ ID NO: 3) with three NFκB binding sequences (ggggattccc; SEQ ID NO: 19), and two Oct1 binding sequences (atgcaaat; SEQ ID NO: 21) added to the 5' end was developed. The variant NOX1 core promoter sequence (SEQ ID NO: 3) of the eNOX1 promoter includes nucleotides 1562-2027 of the NOX1 gene (GenBank Accession No. DQ314883.1) (SEQ ID NO: 2) with two base changes (the first to enhance the CAAT box and the second to knock out an unnecessary ATG start site) and a short downstream sequence (including a TGA stop site and Kozak consensus sequence). Unlike the LOX1 promoter, the small size (483 bp) of the eNOX1 promoter allows for the inclusion of multiple therapeutic genes in the context of an AAV vector.

Furthermore, inclusion of transcription factor binding sequences, such as one or more NFκB and/or Oct1 binding sequences, may improve expression in response to certain stimuli. For example, NF-κB is a transcription factor activated in cells during disease progression and in response to cellular stress. Ganguli A, et al., 2005; Mercurio F and Manning A M, 1999; Zhang Q, et al., 2017. In the context of LOX-1 promoter studies, the NFκB binding motif has been associated with Ang II-induced promoter activation and the Oct-1 binding motif has been associated with Ox-LDL-induced promoter activation. Chen J, et al., BCJ, 2006; Chen J, et al., ATVB, 2006. However, Oct-1 has also been shown to repress NFκB-dependent gene expression (Dela Paz N G, et al., 2006; Voleti B and Agrawal A, 2005), leading to uncertainty as to whether a NOX1 core promoter with additional NFκB and Oct1 binding sequences could activate gene expression in the presence of disease-associated stimuli.

The ability of the eNOX1 promoter (SEQ ID NO: 4) to regulate expression of FLAG-mCherry in vitro in the presence of factors associated with inflammation, specifically Angiotensin II (Ang II), Lipopolysaccharides (LPS), and Oxidized Low Density Lipoprotein (Ox-LDL) was tested. Ang II is a peptide hormone that causes vasoconstriction and increased blood pressure. LPS stimulates the release of inflammatory cytokines leading to acute inflammatory response and, in extreme cases, anaphylactic shock. Ox-LDL is a major driver of vascular pathology in humans.

HEK 293 cells were transfected with 1 μg of a plasmid comprising the eNOXpr-3xFLAG-mCherry construct (SEQ ID NO: 22) and cultured in Dulbecco's modified Eagle's medium (DMEM, Gibco, USA) containing 10% (v/v) fetal bovine serum (FBS), 10 U/mL penicillin. The cell cultures were treated with increasing concentrations of Ang II (Sigma, USA) (0 ng/ml, 100 ng/ml, 1 μg/ml, and 10 μg/ml), LPS (Sigma, USA) (0 ng/ml, 10 ng/ml, 100 ng/ml, and 1 μg/ml), or Ox-LDL (Yiyuanbiotech, China) (0 ng/ml, 10 ng/ml, 1 μg/ml, and 60 μg/ml) at 36 hours and harvested at 60 hours.

Cell extracts were prepared and separated by SDS-PAGE. Western blot analysis was performed using mouse anti-FLAG primary antibody (diluted 1:1000, F-1804, Sigma, USA), mouse anti-β-actin primary antibody (diluted 1:8000, A1978, Sigma, USA) as a loading control, and secondary mouse anti-IgG ALEXA Flour 647 (diluted 1:500, Invitrogen, USA). The relative expression of FLAG and β-actin was visualized and quantified using the enhanced chemiluminescence light method using NIH ImageJ software. Results are shown as the mean±SD from three independent experiments.

Figures 2A, 2B, 2C:
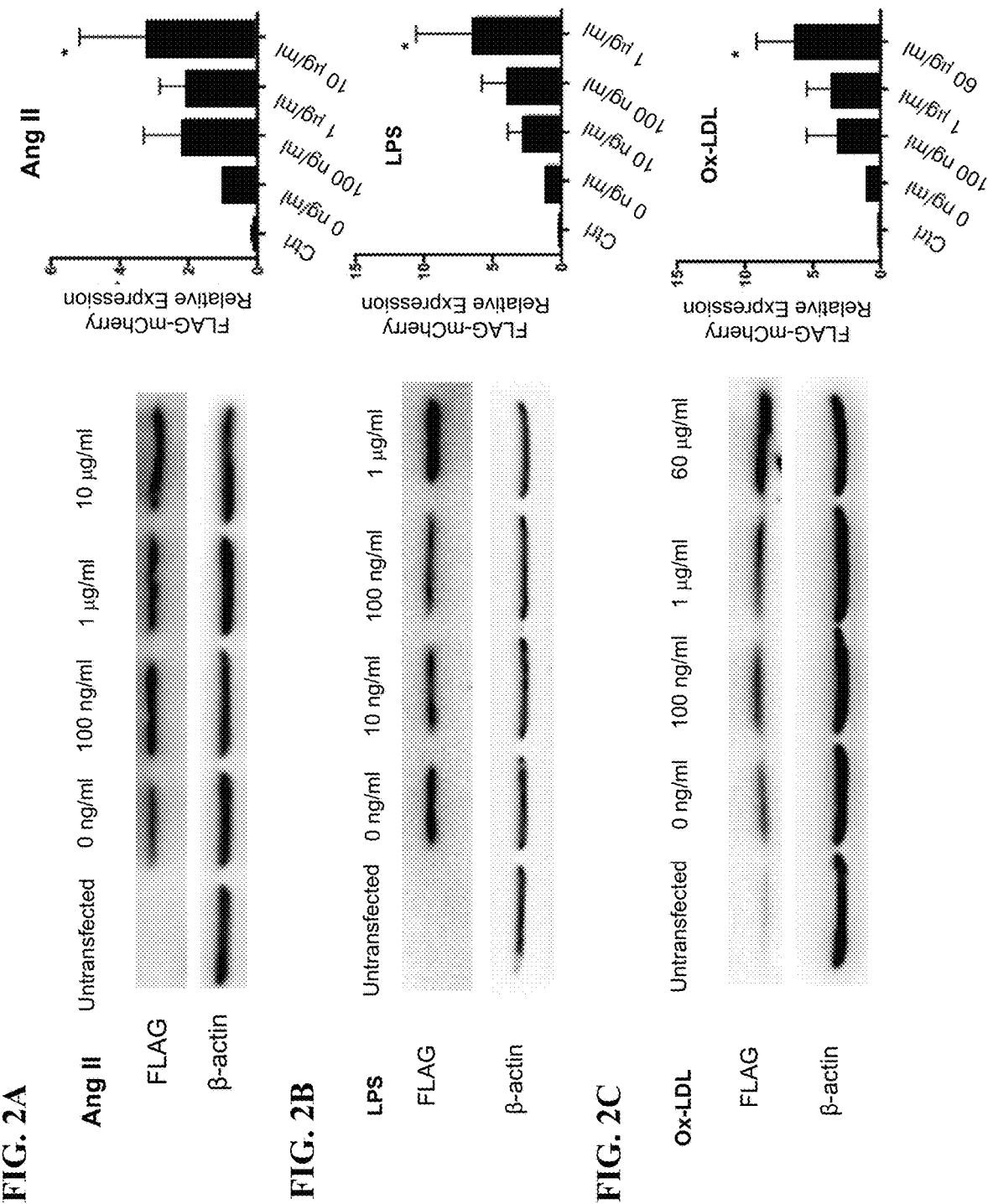
FIG. 2A shows relative expression levels of FLAG under the control of the eNOX1 promoter in the presence of increasing concentrations of Angiotensin-2 (Ang II) compared to an untransfected control.
FIG. 2B shows relative expression levels of FLAG under the control of the eNOX1 promoter in the presence of increasing concentrations of Lipopolysaccharides (LPS) compared to an untransfected control.
FIG. 2C shows relative expression levels of FLAG under the control of the eNOX1 promoter in the presence of increasing concentrations of Oxidized Low Density Lipoprotein (Ox-LDL) compared to an untransfected control.

FIG. 2 shows relative expression levels of FLAG-mCherry under the control of the eNOX1 promoter in the presence of increasing concentrations of Ang II (FIG. 2A), LPS (FIG. 2B), and Ox-LDL (FIG. 2C) compared to an untransfected control. The expression of FLAG-mCherry under control of the eNOX1 promoter trended to increase with the concentration of Ang II, LPS, and ox-LDL, and at the highest concentration of the stimulant, expression was statistically higher than the 0 μg/ml controls.

The relative expression of FLAG-mCherry was also assessed by fluorescence microscopy. Similar to the prior study, HEK 293 cells were transfected with 1 μg of the eNOXpr-3xFLAG-mCherry plasmid or a CMVpr-FLAG-mCherry plasmid. Cells transfected with eNOXpr-3xFLAGmCherry were treated with increasing concentrations of Ang II (0 ng/ml, 100 ng/ml, 1 μg/ml, and 10 μg/ml), LPS (0 ng/ml, 10 ng/ml, 100 ng/ml, and 1 μg/ml), or Ox-LDL (0 ng/ml, 100 ng/ml, 1 μg/ml, and 60 μg/ml) at 36 hours and harvested at 60 hours. Relative expression of FLAG-mCherry was visualized and quantified by fluorescence microscopy (Lica, USA) and ImageJ software.

Figure 3A:
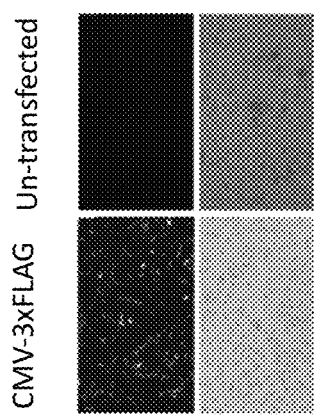
FIG. 3A shows expression of FLAG-mCherry in HEK 293 cells under the control of the CMV promoter and an untransfected control.
Figure 3B:
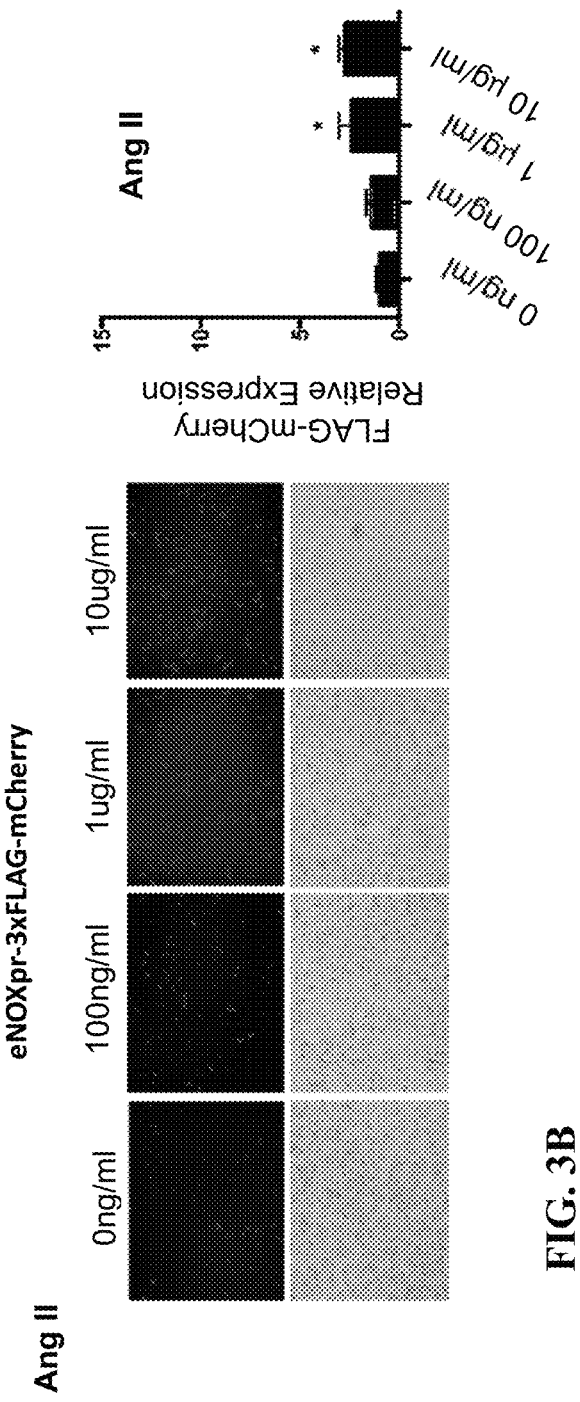
FIG. 3B shows relative expression of FLAG-mCherry in HEK 293 cells transfected with NOXpr-3xFLAG-mCherry and treated with increasing concentrations of Ang II.
Figure 3C:
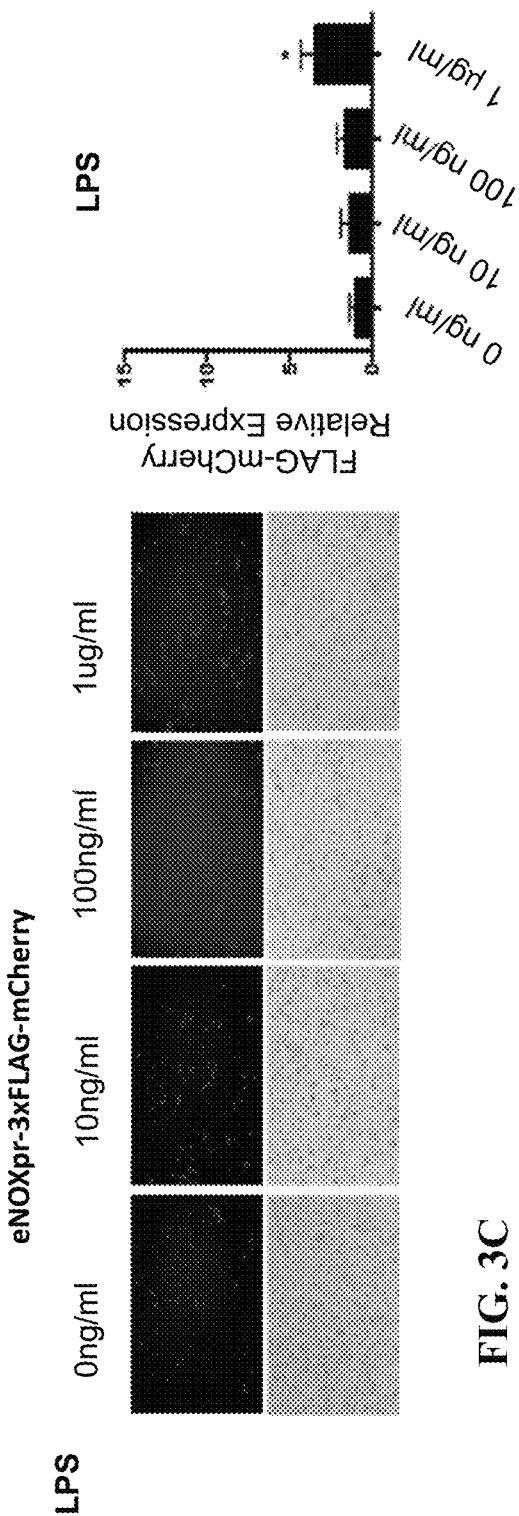
FIG. 3C shows relative expression of FLAG-mCherry in HEK 293 cells transfected with NOXpr-3xFLAG-mCherry and treated with increasing concentrations of LPS.
Figure 3D:
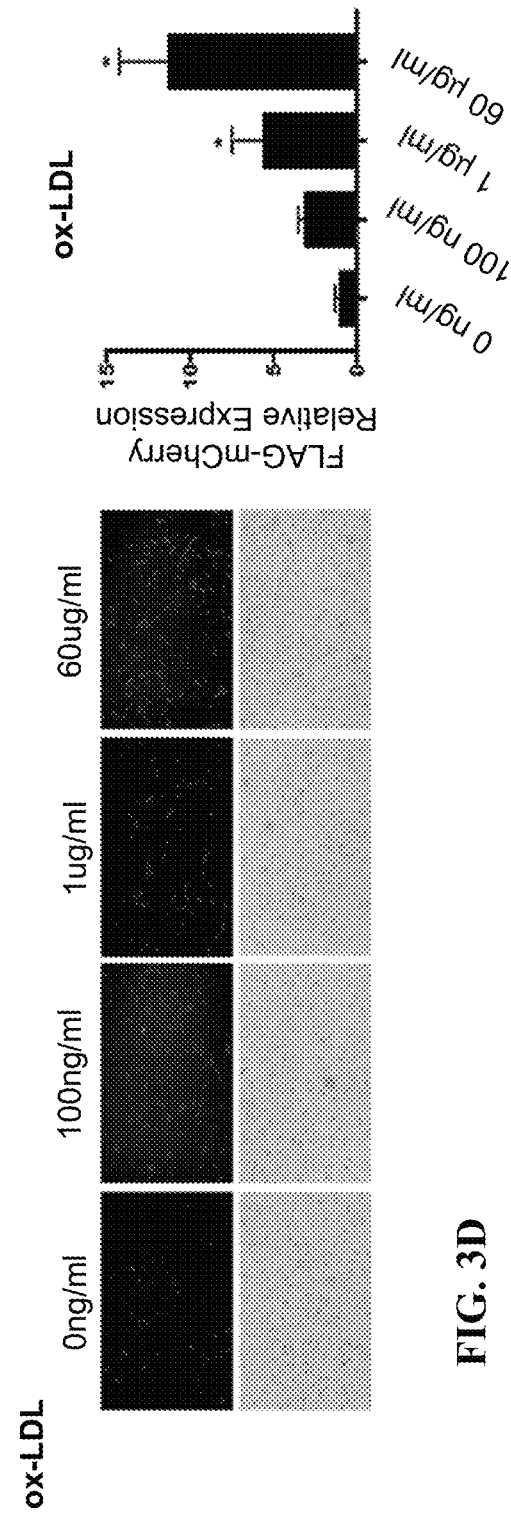
FIG. 3D shows relative expression of FLAG-mCherry in HEK 293 cells transfected with NOXpr-3xFLAG-mCherry and treated with increasing concentrations of ox-LDL.

FIG. 3 shows relative expression levels of FLAG-mCherry under the control of the eNOX1 promoter in the presence of increasing concentrations of Ang II (FIG. 3B), LPS (FIG. 3C), and Ox-LDL (FIG. 3D). Data are expressed as mean±SD (*P<0.05). Expression of mCherry under the constitutive control of the CMV promoter and an untransfected control are shown in FIG. 3A. The expression of FLAG-mCherry under control of the eNOX1 promoter trended to increase with the concentration of Ang II, LPS, and Ox-LDL, and at the highest concentration expressions were statistically higher than the 0 μg/ml controls.

Example 3

In Vivo AAV Expression with an Exemplary NOX1 Core Promoter

Figure 4A:
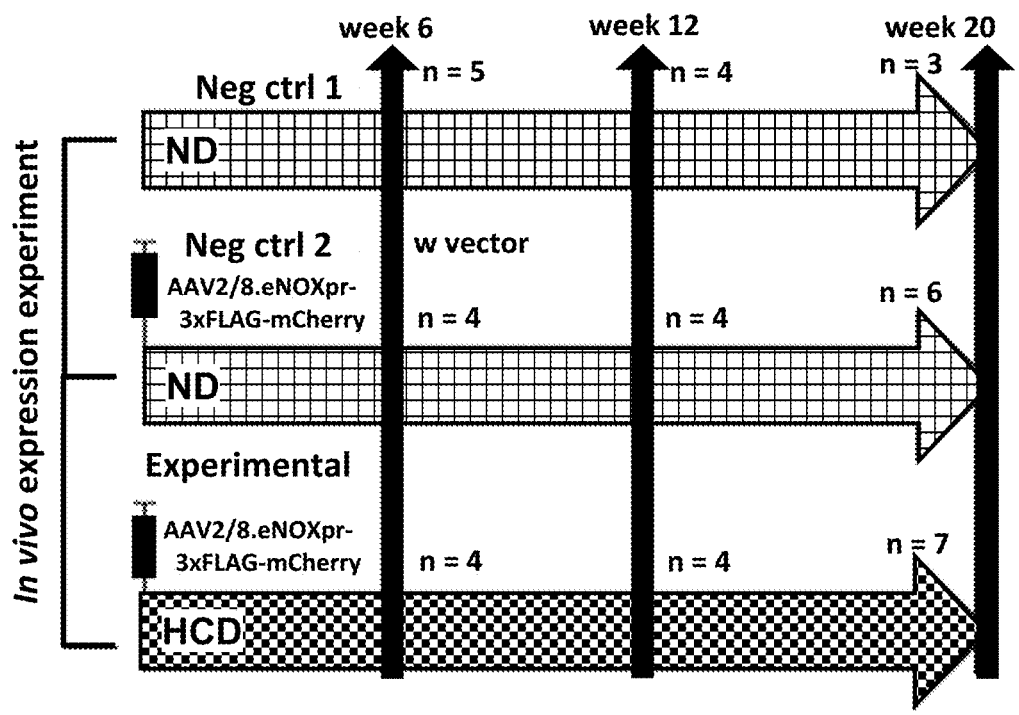
FIG. 4A shows the design of an in vivo expression experiment in the low density lipoprotein receptor knockout (LDLR-KO) mouse, as described in Example 3. Three groups of LDLR-KO mice were used in the 20-week experiment. Group 1 (n=12) was a negative control group of untreated LDLR-KO mice maintained on a normal diet (ND) from day 0 to week 6 (n=5), week 12 (n=4), or week 20 (n=3). Groups 2 and 3 received AAV2/8.eNOXpr-3xFLAG-mCherry on day 0, followed by two booster injections at an interval of approximately 2 days. Group 2 (n=14) was a second negative control group and received the ND from day 0 to week 6 (n=4), week 12 (n=4), or week 20 (n=6). Group 3 (n=15) received a high cholesterol diet (HCD) from day 0 to week 6 (n=4), week 12 (n=4), or week 20 (n=7).

The responsiveness of the eNOX1 promoter (SEQ ID NO: 4) was tested in the context of an AAV2/8 expression vector in a high lipid mouse model. Low density lipoprotein receptor knockout (LDLR-KO) mice fed a high cholesterol diet (HCD) develop vascular pathology, including immune cell arterial influx, smooth muscle cell proliferation, and atherosclerotic plaque formation. Getz G S and Reardon C A, 2005; Li D, et al., 2006; Liu Y, et al., 2005; Pan J H, et al., 2004; Chen J, et al., 2018. The level of expression from the eNOX1 promoter was monitored over time as the vascular pathology of the LDLR-KO mice progressed. The expression construct tested included a FLAG-mCherry fusion protein under the control of the eNOX1 promoter with flanking AAV2 inverted terminal repeats (ITRs) and was packaged into AAV serotype 8 capsid under GMP conditions by OBiO Technology Corp., Ltd. (Shanghai, China). The experimental design for testing AAV2/8.eNOXpr-3xFLAG-mCherry is shown in FIG. 4A.

The LDLR-KO strain (B6; 12957-Ldlrtm1Her/J) was purchased from Jackson Laboratories (Bar Harbor, Me., USA). The mice were group-housed under constant temperature (23±2° C.) and 40-60% humidity with humane care and maintained on a 12 hour/12 hour, light/dark cycle. Food and water were accessed ad libitum. Study protocols about laboratory animal use were in accordance with the guidelines for the Beijing Friendship Hospital Animal Care and Ethics Committee.

Three groups of eight-week old LDLR-KO mice weighing 16-20 grams were used in the 20-week experiment. Group 1 (n=12) was a negative control group of untreated LDLR-KO mice maintained on a normal diet (ND) from day 0 to week 6 (n=5), from day 0 to week 12 (n=4), or from day 0 to week 20 (n=3). Groups 2 and 3 received AAV2/8.eNOXpr-3xFLAG-mCherry on day 0 at a titer of 1×10$^{11}$ viral encapsidated genomes (eg)/mL via tail vein injection of 200 uL virus per mouse, followed by two booster injections at an interval of approximately 2 days. Group 2 (n=14) was a second negative control group and received the ND from day 0 to week 6 (n=4), day 0 to week 12 (n=4), or day 0 to week 20 (n=6). Group 3 (n=15) received a high cholesterol diet (HCD) from day 0 to week 6 (n=4), from day 0 to week 12 (n=4), or day 0 to week 20 (n=7). The HCD, which consisted of 4% cholesterol and 10% Coco butter (Beijing HFK Bioscience Company, China), was used to ensure the development of atherosclerosis. At weeks 6, 12, and 20, animals were humanely sacrificed, and tissues harvested for eNOX1 promoter expression analysis.

Figure 5A:
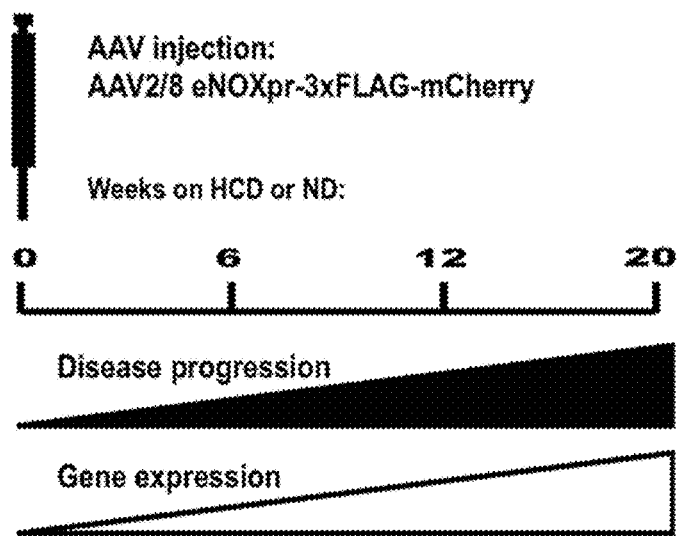
FIG. 5A is a schematic illustrating an increase of disease progression and gene expression over time in LDLR-KO mice fed a high cholesterol diet and following injection with eNOX1 promoter vector.
Figure 5B:
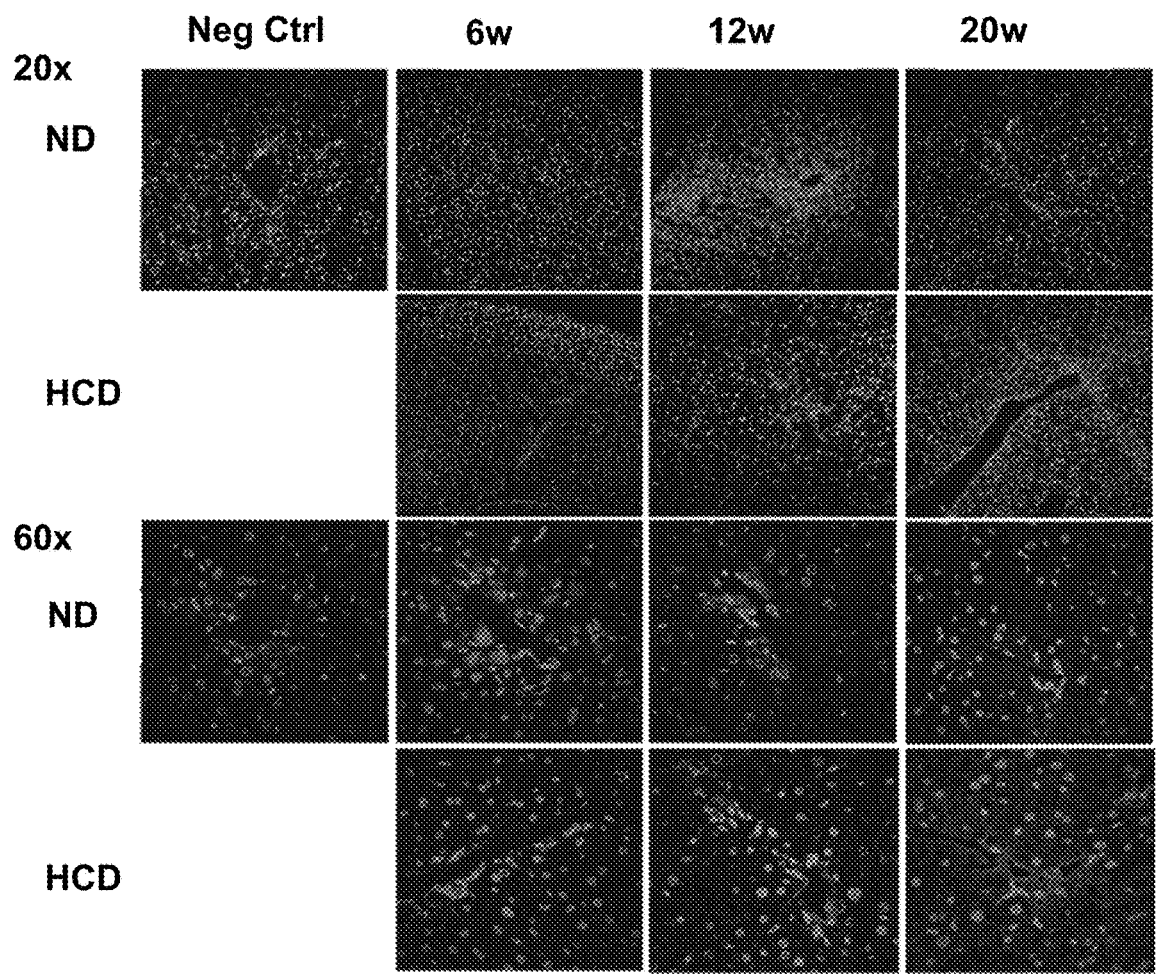
FIG. 5B shows immunofluorescence staining for FLAG in liver of HCD-fed and ND-fed LDLR-KO mice following injection of AAV2/8.eNOXpr-3xFLAG-mCherry at 6 weeks, 12 weeks, and 20 weeks post-injection (20× and 60× magnifications). The tissue was counterstained with DAPI.

Regulated expression of FLAG-mCherry under the eNOX1 promoter in liver at 6 weeks, 12 weeks, and 20 weeks was measured by immuno-fluorescence staining for FLAG (FIG. 5B). Frozen sections were cryostat-microtome shaved from frozen liver tissues. Slides of the tissues were incubated with primary antibodies against FLAG (dilution 1:100, F-1804, Sigma, USA) overnight at 4° C. After washing with phosphate-buffered saline (PBS) for three times, the tissues were incubated with a mixture of Alexa Fluor 647 anti-mouse secondary antibody (dilution 1:500, Invitrogen, USA) at room temperature for 1 hour. The sections were counter-stained with DAPI. The stained tissue was viewed and photographed using a confocal microscope (Olympus, Japan) at 20× and 60× magnification.

The activity of the eNOX1 promoter is shown at the 6, 12, and 20 week time points in representative sections in FIG. 5B. Immunofluorescence staining shows that following injection of AAV2/8.eNOXpr-3xFLAG-mCherry, more transgene expression is observed among the HCD-fed mice than the ND-fed mice at each of the three time points. FLAG-mCherry expression continued to rise in the HCD-fed group from week 6, through week 12, with the highest level of expression observed at week 20. In addition, blood vessel and liver hepatocyte cell transduction were observed.

Figure 5C:
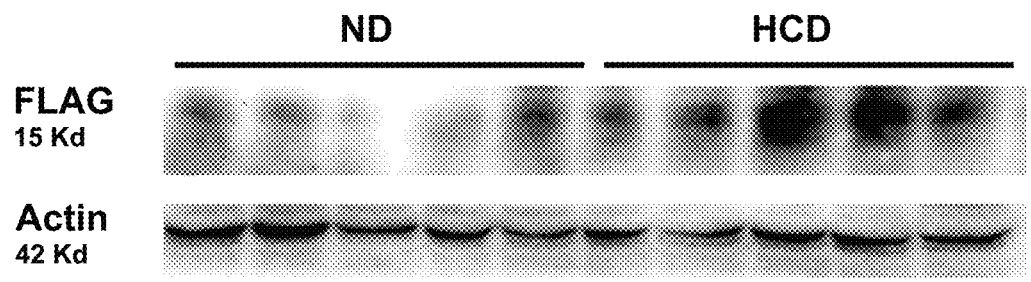
FIG. 5C shows a Western blot for FLAG in liver tissue of HCD-fed and ND-fed LDLR-KO mice following injection of AAV2/8.eNOXpr-3xFLAG-mCherry at 20 weeks post-injection. Detection of mouse β-actin served as a loading control.

In vivo expression of AAV2/8.eNOXpr-3xFLAG-mCherry was compared between ND-fed mice and HCD-fed mice at the 20-week time point by Western blot analysis using protein extracted from frozen liver tissues (FIG. 5C). Western blot analysis was performed using mouse anti-FLAG primary antibody (diluted 1:1000, F-1804, Sigma, USA) and mouse anti-β-actin primary antibody (diluted 1:8000, A1978, Sigma, USA) as a loading control. The membranes were visualized by the enhanced chemiluminescence light method. Densitometric results using ImageJ software show that expression from the eNOX1 promoter was more than five-fold higher in the HCD-fed mice compared to the ND-fed mice at the 20-week time point (FIG. 5E). Data are expressed as mean±SD (*P<0.05).

Figure 5D:
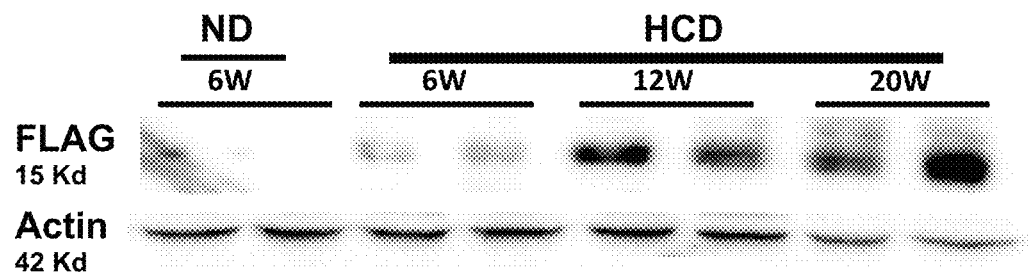
FIG. 5D shows a Western blot for FLAG in liver tissue of HCD-fed and ND-fed LDLR-KO mice following injection of AAV2/8.eNOXpr-3xFLAG-mCherry. Results are shown for ND-fed mice at 6 weeks post-injection and for HCD-fed mice at 6, 12, and 20 weeks post-injection. Detection of mouse β-actin served as a loading control.
Figure 5E:
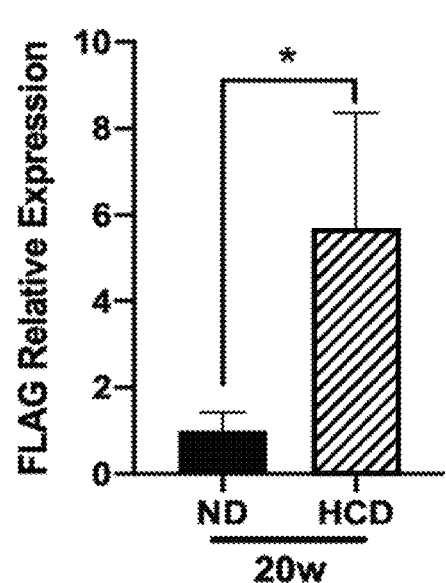
FIG. 5E shows results of densitometric analysis of the Western blot analysis shown in FIG. 5C. Data are expressed as mean±SD (*P<0.05).
Figure 5F:
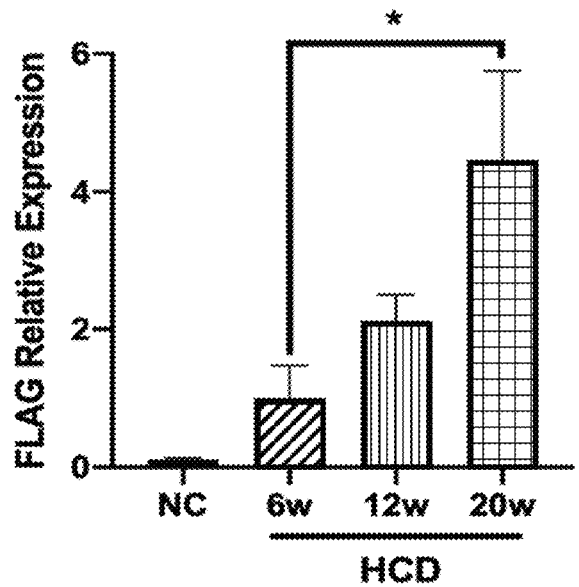
FIG. 5F shows results of densitometric analysis of the Western blot analysis shown in FIG. 5D. Data are expressed as mean±SD (*P<0.05).

In vivo expression of AAV2/8.eNOXpr-3xFLAG-mCherry was also compared between ND-fed mice at the 6-week time point and HCD-fed mice at the 6-, 12-, and 20-week time points by Western blot analysis using protein extracted from frozen liver tissues (FIG. 5D). Western blot analysis was performed as described in the above paragraph. Densitometric results show that expression from the eNOX1 promoter increased in a time-dependent manner in the HCD-fed mice and was more than four-fold higher in the HCD-fed mice at 20-weeks compared to the ND-fed control mice (FIG. 5F). Data are expressed as mean±SD (*P<0.05).

Collectively, the immunofluorescence and Western analyses are consistent with the Ox-LDL-stimulated eNOX1 promoter expression observed in HEK 293 cells (FIG. 2 and FIG. 3). FLAG-mCherry expression was observed in blood vessels and hepatocytes of the liver. Further, as vascular pathology of LDLR-KO mice fed a HCD diet progressed, the level of transcription from the eNOX1 promoter of the AAV2/8.eNOXpr-3xFLAG-mCherry was shown to also temporally increase. These data suggest that therapeutic expression from the eNOX1 promoter increases in the face of increasing vascular pathology occurring over time (see FIG. 5A).

Example 4

Modification of FOXP3 Zinc Finger and Leucine Zipper Region

Forkhead box proteins (FOXP) are a family of transcription factors (e.g., FOXP1, FOXP2, FOXP3, and FOXP4) involved in regulating the expression of genes involved in development, immune disorders, and cancer progression. FOXP family proteins have a zinc finger and leucine zipper region understood to be involved in protein dimerization. Kim J, et al., 2019; Wang B, et al., 2003; Song X, et al., 2012. Presumably, a FOXP expressed in vivo from an AAV vector could dimerize with its endogenous FOXP counterpart. To enhance homodimerization of FOXP expressed from an AAV vector and increase the likelihood that efficacy is due to the AAV-delivered FOXP, replacement of one FOXP zinc finger and leucine zipper region with that of another FOXP was explored.

A chimeric FOXP3/FOXP1 ("FOXP3(P1)") protein was designed in which an amino acid sequence from the zinc finger and leucine zipper region of human FOXP3 was replaced with an analogous amino acid sequence from the zinc finger and leucine zipper region of FOXP1. The FOXP3 (P1) amino acid sequence (SEQ ID NO: 28), which is 431 amino acids in length, includes amino acids 1 to 225 and 264 to 431 of human FOXP3 (NCBI Reference Sequence NP 054728.2; SEQ ID NO: 24) flanking amino acids 147 to 184 of human FOXP1 (GenBank: AF146698.2; SEQ ID NO: 26). The FOXP3 and FOXP1 zinc finger and leucine zipper regions that were interchanged share only about 45% homology. The resulting FOXP3(P1) chimeric protein (SEQ ID NO: 28) should preferentially homodimerize over dimerizing with endogenous FOXP3. Potential heterodimerization of FOXP3(P1) with endogenous FOXP1 is unlikely to be harmful since endogenous FOXP3 and FOXP1 are understood to already form heterodimers. Ren J, et al., 2019; Konopacki C, et al., 2019; Li B, et al., 2007; Rudra D, et al, 2012; Deng G, et al, 2019.

Example 5

FOXP3(P1) and IL10 Dual Gene AAV Vector

Vascular smooth muscle cells are a target cell type in the AAV treatment of atherosclerosis. Based on the studies described in Example 1, an increase in TGFβ expression but not IL10 expression was observed in FOXP3-expressing smooth muscle cells. Inclusion of nucleotide sequences for both FOXP3(P1) and IL10 in an AAV vector may increase the therapeutic efficacy observed, such as regression of vascular pathologies and/or prevention of further development of vascular pathologies. To reduce the overall expression of FOXP3(P1) and IL10, use of a small lipid-responsive promoter was explored. The eNOX1 promoter described in Example 2 allows for the inclusion of multiple therapeutic genes in the context of an AAV vector, including both FOXP3(P1) and IL10.

Figure 6:
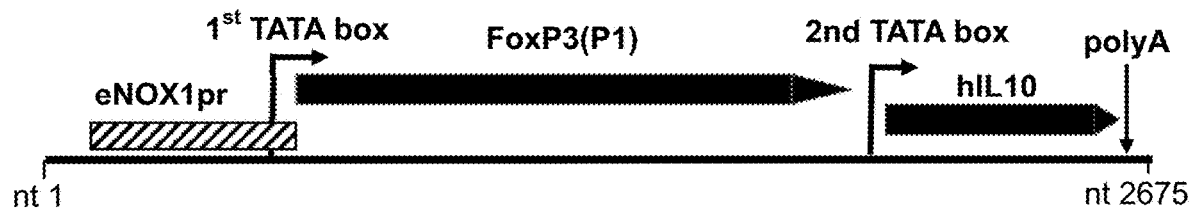
FIG. 6 is a schematic illustrating eNOX1pr-FoxP3(P1)-IL10 (SEQ ID NO: 34), a three-component expression construct totaling 2675 nucleotides and comprising the eNOX1 promoter (SEQ ID NO: 4), FOXP3(P1) coding sequence (SEQ ID NO: 29), and a human IL10 coding sequence (SEQ ID NO: 32).

Design of a three-component expression construct (eNOX1pr-FoxP3(P1)-IL10; SEQ ID NO: 34) totaling 2675 nucleotides comprising the eNOX1 promoter (SEQ ID NO: 4), FOXP3(P1) coding sequence (SEQ ID NO: 29), and a human IL10 coding sequence (SEQ ID NO: 32) is shown in FIG. 6. Since overexpression of IL10 can be detrimental, the construct was designed such that the IL10 coding sequence does not have a dedicated enhancer-promoter region. Instead, a synthetic TATA box sequence was placed downstream of FOXP3(P1) and upstream of IL10 allowing for limited expression from mRNA translation from the IL10 coding sequence start methionine. A synthetic poly-adenylation sequence was placed downstream of the IL10 coding sequence. The expression construct with flanking AAV2 inverted terminal repeats (ITRs) was packaged into AAV serotype 8 capsid (AAV2/8.eNOXpr-FoxP3(P1)-IL10) under GMP conditions by OBiO Technology Corp., Ltd. (Shanghai, China) for gene delivery into mice.

Example 6

Administration of AAV2/8.eNOXpr-FoxP3(P1)-IL10 to an Animal Model of Established and Ongoing Atherosclerosis Therapeutic benefit of dual expression of FOXP3 (P1) and IL10 from eNOX1pr-FoxP3(P1)-IL10 gene delivery against established and ongoing atherosclerotic disease was tested. The LDLR-KO model fed HCD develops vascular pathology, including immune cell arterial influx, smooth muscle cell proliferation, and atherosclerotic plaque formation. In previous gene therapy treatment trials involving the LDLR-KO model, treatment by tail vein injection of the putative therapeutic AAV vector was initiated at the same time as the HCD was initiated. Cao M, et al., 2015; Zhu H, et al., JTM 2014; Zhu H, et al., Plos One 2014; Cao M, et al., 2011; Khan J A, et al., 2011; Khan J A, et al., 2010; Dandapat A, et al., BBRC, 2007; Dandapat A, et al., Gene Ther, 2007; Liu Y, et al., 2005. Hence, testing of a vector's therapeutic effect when present from day 0 through week 20 may be more accurately described as a prevention model as opposed to a treatment model.

Figure 7:
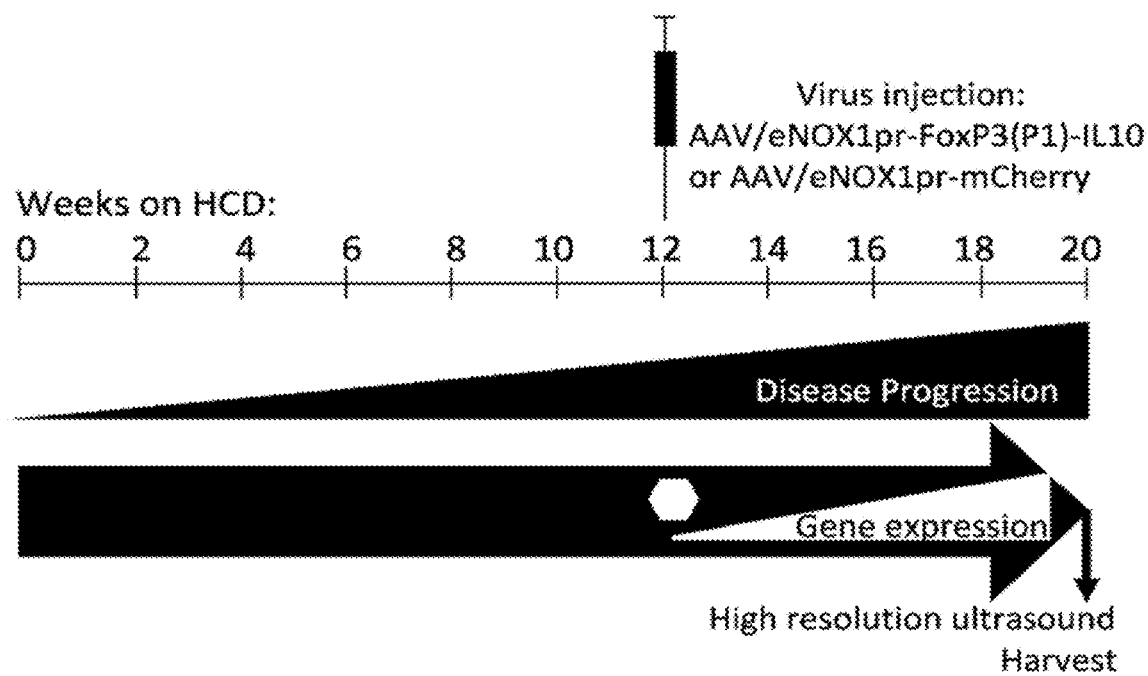
FIG. 7 is a schematic illustrating an animal treatment model of existing and ongoing vascular pathology involving first establishing disease progression by maintaining a LDLR-KO mouse on a HCD and then subsequently administering a therapeutic vector (e.g., AAV.eNOXpr-FoxP3(P1)-IL10) some weeks to months later. High resolution ultrasound may be used to monitor disease progression and treatment.

This previous mouse model design of administering therapy at the same time as initiating the HCD is not representative of the clinical setting where human patients are first diagnosed and then treated. Patients typically seek medical intervention when they are symptomatic, and are likely to have significant and established vascular pathology. An animal treatment model that more closely mimics this clinical situation was developed in which mice are maintained on a HCD for several months prior to the administration of the therapeutic vector (e.g., as shown in FIG. 7).

Figure 4B:
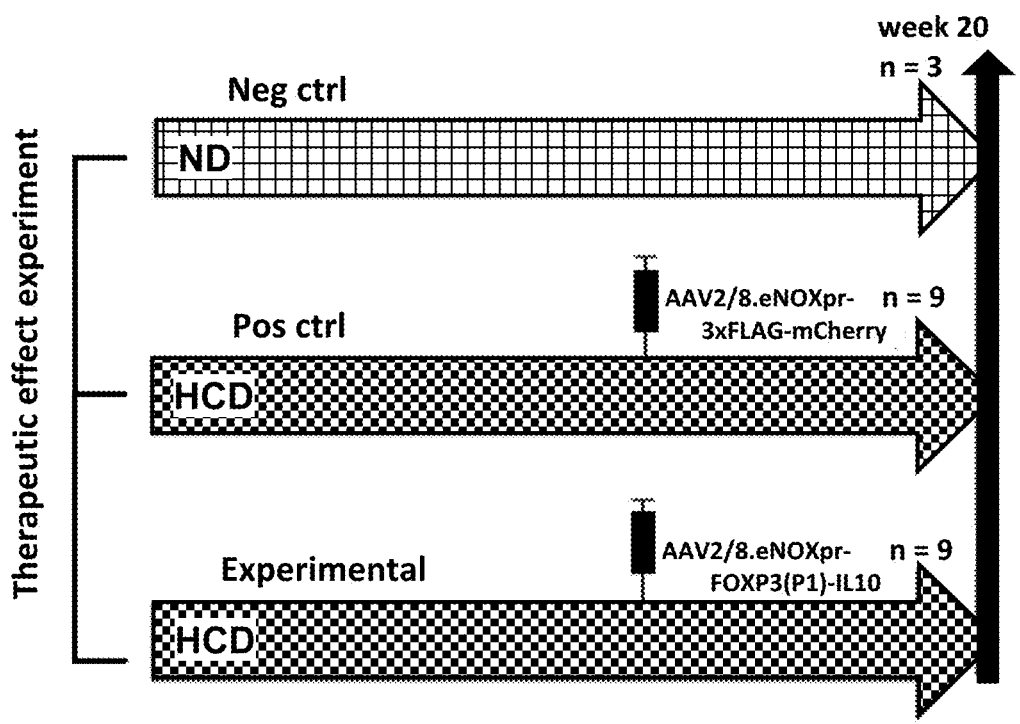
FIG. 4B shows the design of an in vivo therapeutic effect experiment in the LDL-KO mouse, as described in Example 6. Three groups of LDLR-KO mice were used in a 20-week study. Group 1 was a negative control group of untreated LDLR-KO mice maintained on a normal diet (ND) from day 0 to week 20 (n=3). Groups 2 and 3 each received the HCD diet from day 0 through week 20. At week 12, Group 2 received the AAV2/8.eNOXpr-3xFLAG-mCherry vector (disease positive control) (n=9) and Group 3 received the AAV2/8.eNOXpr-FOXP3(P1)-IL10 vector (experimental group) (n=9), followed by two booster injections at an interval of approximately 2 days.

AAV2/8.eNOXpr-FOXP3(P1)-IL10 vector was tested using the experimental design shown in FIG. 4B. This therapeutic-focused study differed from the animal expression study of Example 3 and FIG. 4A by allowing for a 12-week HCD-induced pathology accumulation period before therapeutic intervention. Three groups of eight-week old LDLR-KO mice were used in a 20-week study. Group 1 was a negative control group of untreated LDLR-KO mice maintained on a normal diet (ND) from day 0 to week 20 (n=3). Groups 2 and 3 each received the HCD diet from day 0 through week 20. However, the AAV vector injection was delayed until week 12 to allow for HCD-induced pathology to accumulate. At week 12, Group 2 received the AAV2/8.eNOXpr-3xFLAG-mCherry vector (disease positive control) (n=9) and Group 3 received the AAV2/8.eNOXpr-FOXP3(P1)-IL10 vector (experimental group) (n=9) at a titer of $1\times10^{11}$ viral encapsidated genomes (eg)/mL via tail vein injection of 200 uL virus per mouse, followed by two booster injections at an interval of approximately 2 days. The high cholesterol diet (HCD) comprised 4% cholesterol and 10% Coco butter. The animals were assessed for therapeutic effects against HCD-induced atherosclerosis by high resolution ultrasound using VisualSonics Vevo2100 at 20 weeks. Thereafter, the mice were euthanized by overdose of 1% pentobarbital, and tissues harvested for other analyses.

Figure 8A:
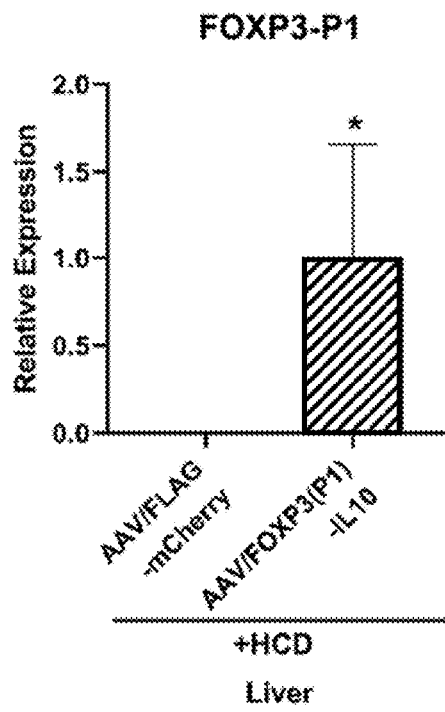
FIG. 8A and FIG. 8B show qRT-PCR analysis of FoxP3 (P1) mRNA in liver tissue (FIG. 8A) and heart tissue (FIG. 8B) of LDLR-KO mice that were maintained on a HCD beginning at day 1, administered AAV2/8.eNOXpr-FOXP3 (P1)-IL10 or AAV2/8.eNOXpr-3xFLAG-mCherry at week 12, and harvested at week 20. FoxP3(P1) expression was normalized to expression of GAPDH.
Figure 8B:
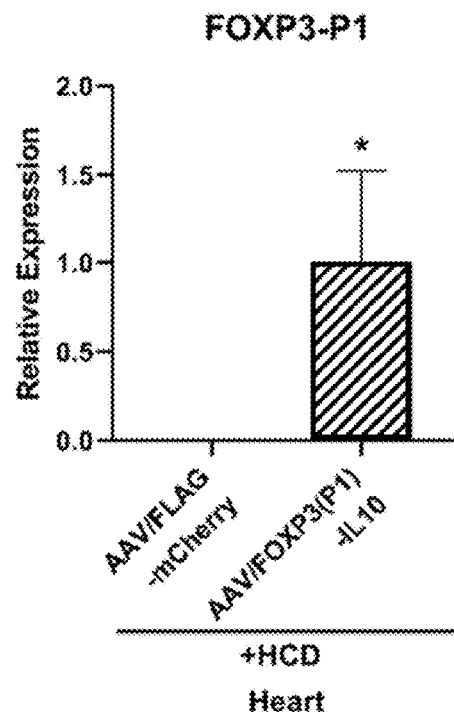
Figure 8C:
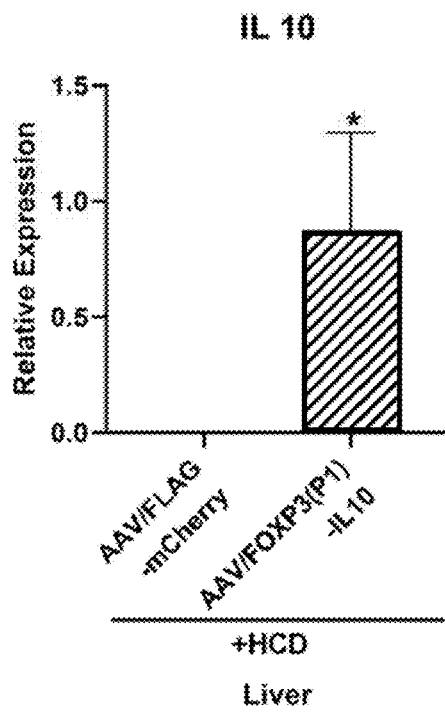
FIG. 8C and FIG. 8D show qRT-PCR analysis of IL10 mRNA in liver tissue (FIG. 8C) and heart tissue (FIG. 8D) of LDLR-KO mice that were maintained on a HCD beginning at day 1, administered AAV2/8.eNOXpr-FOXP3(P1)-IL10 or AAV2/8.eNOXpr-3xFLAG-mCherry at week 12, and harvested at week 20. FoxP3(P1) expression was normalized to expression of GAPDH.
Figure 8D:
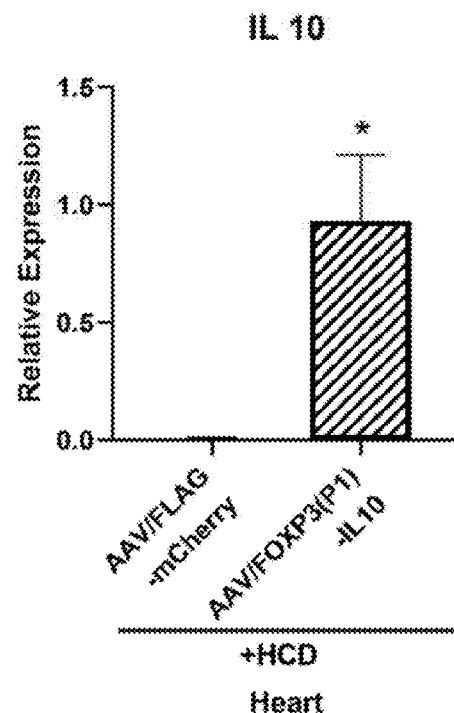
Figure 9A:
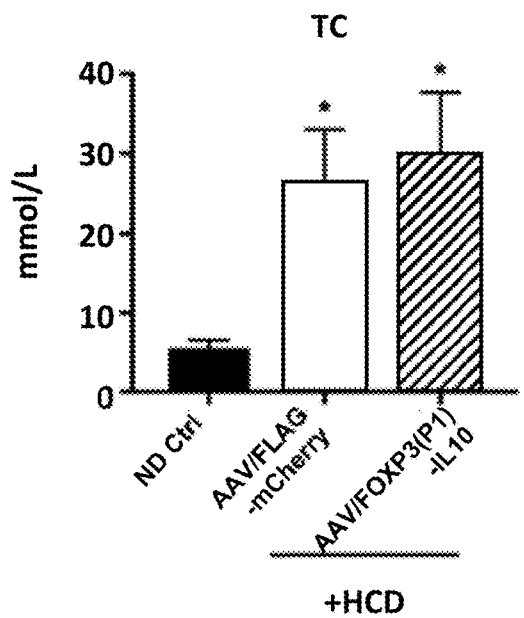
FIG. 9A shows concentration of total plasma cholesterol at 20 weeks for LDLR-KO mice fed a normal diet or fed a high cholesterol diet and administered at 12 weeks either the AAV2/8.eNOXpr-3xFLAG-mCherry vector or the AAV2/8.eNOXpr-FOXP3(P1)-IL10 vector.
Figure 9B:
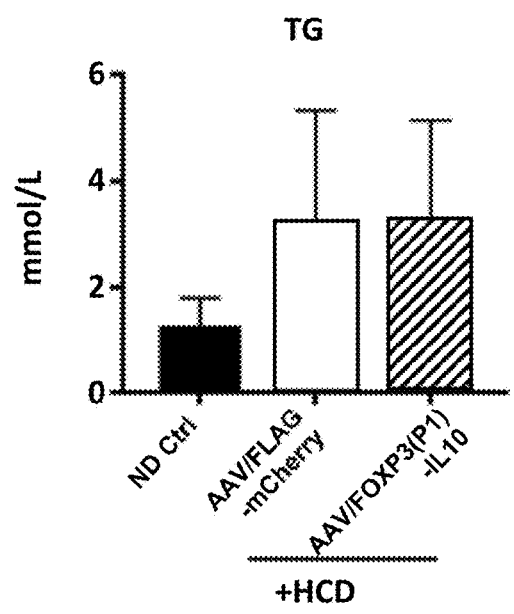
FIG. 9B shows concentration of triglycerides at 20 weeks for LDLR-KO mice fed a normal diet or fed a high cholesterol diet and administered at 12 weeks either the AAV2/8.eNOXpr-3xFLAG-mCherry vector or the AAV2/8.eNOXpr-FOXP3(P1)-IL10 vector.
Figure 9C:
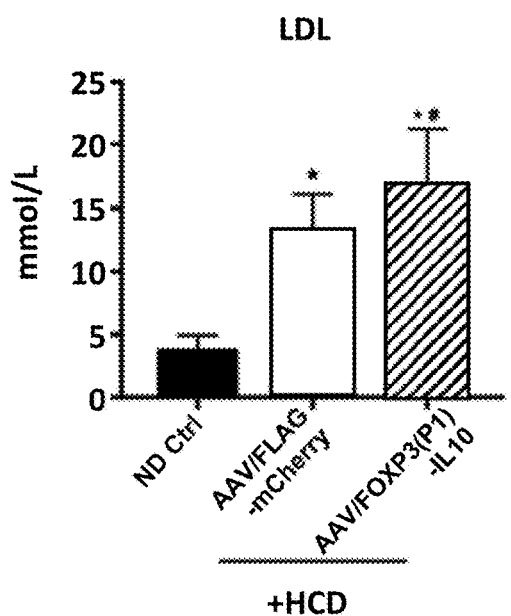
FIG. 9C shows concentration of low-density lipoprotein at 20 weeks for LDLR-KO mice fed a normal diet or fed a high cholesterol diet and administered at 12 weeks either the AAV2/8.eNOXpr-3xFLAG-mCherry vector or the AAV2/8.eNOXpr-FOXP3(P1)-IL10 vector.
Figure 9D:
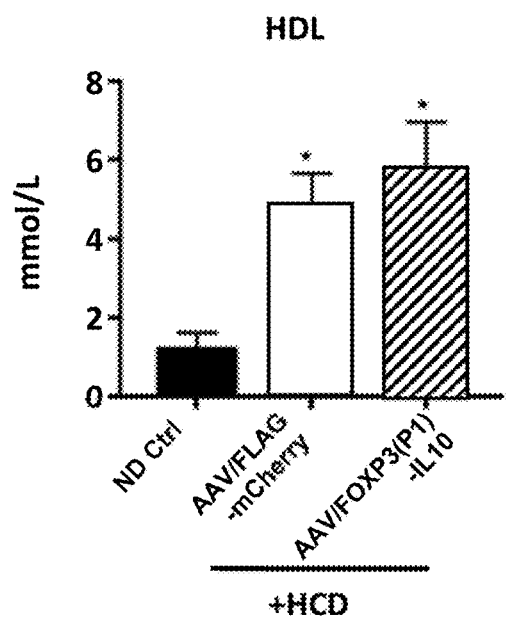
FIG. 9D shows concentration of high-density lipoprotein at 20 weeks for LDLR-KO mice fed a normal diet or fed a high cholesterol diet and administered at 12 weeks either the AAV2/8.eNOXpr-3xFLAG-mCherry vector or the AAV2/8.eNOXpr-FOXP3(P1)-IL10 vector.

The relative expression of FOXP3(P1) in liver (FIG. 8A) and heart (FIG. 8B) and of IL10 in liver (FIG. 8C) and heart (FIG. 8D) in Group 2 and Group 3 animals receiving AAV2/8.eNOXpr-3xFLAG-mCherry and AAV2/8.eNOXpr-FOXP3(P1)-IL10, respectively was determined at week 20 (8 weeks after vector administration). Relative expression of the FOX3(P1) and IL10 mRNA was determined by quantitative, reverse transcription PCR (qRT-PCR). Total mRNA was extracted from liver and heart tissue using Qiagen RNeasy Mini Kit (Qiagen, Germany) and cDNA was reversely transcribed. The qRT-PCR system and data analysis were performed in accordance with Yang A T, et al. The primers used are listed in Table 4, below. The forward FoxP3(P1) primer is specific for FoxP3 and the reverse primer is specific for the FoxP1 leucine zipper/zinc finger region. FoxP3(P1) and IL10 expression was normalized to expression of GAPDH.

TABLE 4

Primers for real-time PCR

| Gene | Primers | |
|---|---|---|
| FoxP3(P1) | Forward 5'-AAAGATAGTACGTTGTCCGCAG-3' | (SEQ ID NO: 37) |
| | Reverse 5'-ATTTGCACCCTGCATTGCGC-3' | (SEQ ID NO: 38) |
| IL10 | Forward 5'-TCTGTGCTGCCTCGTGCTCC-3' | (SEQ ID NO: 39) |
| | Reverse 5'-TCTGACAGAGCCTGGCACCC-3' | (SEQ ID NO: 40) |
| mGAPDH | Forward 5'-TCCACTCACGGCAAATTCAAC-3' | (SEQ ID NO: 41) |
| | Reverse 5'-CGCTCCTGGAAGATGGTGATG-3' | (SEQ ID NO: 42) |

As shown in FIGS. 8A, 8B, 8C, and 8D, the presence of FoxP3(P1) and IL10 mRNA was observed in liver and heart tissue of mice injected with AAV2/8.eNOXpr-FOXP3(P1)-IL10 (Group 3), but not in mice treated with AAV2/8.eNOXpr-3xFLAG-mCherry (Group 2). All data were expressed as means±SD (*P<0.05).

Total plasma cholesterol (TC, FIG. 9A), triglycerides (TG, FIG. 9B), low-density lipoproteins (LDL, FIG. 9C), and high-density lipoproteins (HDL, FIG. 9D) were measured at 20 weeks for each of Groups 1-3 mice using an automated chemistry analyzer (AU480, Olympus, Japan). As shown in FIG. 9, blood lipid levels were high in both groups on HCD (Groups 2 and 3) compared to the ND control group (Group 1). The AAV2/8.eNOXpr-3xFLAG-mCherry (Group 2) and AAV2/8.eNOXpr-FOXP3(P1)-IL10 (Group 3) animal groups were statistically different from the ND control (Group 1) with respect to TC, LDL, and HDL. All data were expressed as means±SD (*P<0.05).

Animal weight was measured by digital scale. Liver enzyme and albumin levels were determined by automatic chemistry analyzer (AU480, Olympus, Japan) as a measure of potential immunological response to the transgenes and AAV capsid proteins. FIG. 10 shows that animal weight (FIG. 10A) and levels of alanine aminotransferase (ALT, FIG. 10B), aspartate aminotransferase (AST, FIG. 10C), alkaline phosphatase (ALP, FIG. 10D), and albumin (ALB, FIG. 10E) were statistically similar among all three animal groups suggesting no significant liver damage and no significant immune response to the transgenes or AAV8 capsid proteins at week 20 (8 weeks post-vector administration).

Example 7

Histological and Staining Analysis Following Treatment with AAV2/8.eNOXpr-FoxP3(P1)-IL10

Effects of AAV2/8.eNOXpr-FOXP3(P1)-IL10 vector compared to that of AAV2/8.eNOXpr-3xFLAGmCherry on the aorta challenged with a high cholesterol diet were considered. Entire aortas from the animals in each of Groups 1-3, including the aortic arches and the thoracic and abdominal regions, were removed for further analysis following euthanization of the animals by overdose with 1% pentobarbital. The aortas were flushed with saline solution.

Figure 11A:
FIG. 11A shows images of representative aortas stained with Oil Red O from LDLR-KO mice fed a normal diet or fed a high cholesterol diet and administered at 12 weeks either the AAV2/8.eNOXpr-3xFLAG-mCherry vector or the AAV2/8.eNOXpr-FOXP3(P1)-IL10 vector.
Figure 11B:
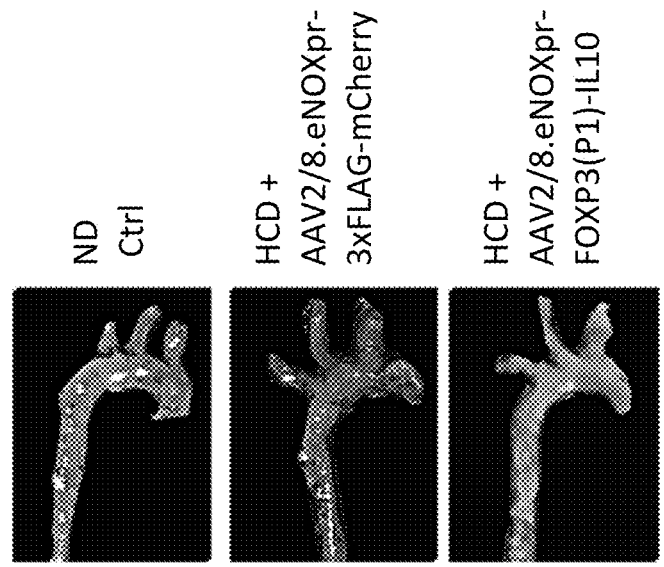
FIG. 11B shows enlarged images of the aortic arch region of the Oil Red O-stained aortas shown in FIG. 11A.

Whole aortas were fixed in 10% buffered formalin before Oil Red O staining of triglycerides, lipids, and lipoproteins to identify atherosclerotic lesions, as previously described. Dandapat A, et al., Gene Therapy, 2007; Li D, et al., 2006. Unstained small animal aortas normally appear translucent, but show lipid deposition as white areas. The stained aortas were inspected under a dissecting microscope and any small pieces of adventitial fat that remained attached were removed very carefully without disturbing the aorta itself as well as the internal lipid accumulations (plaques). The stained aortas were photographed under natural light using a 10-megapixel digital camera (Nikon, Japan). Images of representative aortas stained with Oil Red O from each animal group are shown in FIG. 11A and enlargements of the aortic arch are shown in FIG. 11B. More numerous areas of red color appear in both the aortic arch (FIG. 11B) and in the descending aorta (FIG. 11A) of AAV2/8.eNOXpr-3xFLAGmCherry vector-treated mice fed a HCD (Group 2) compared to control mice receiving a normal diet and no vector (Group 1) or AAV2/8.eNOXpr-FOXP3(P1)-IL10 vector-treated mice fed a HCD (Group 3).

Figure 11C:
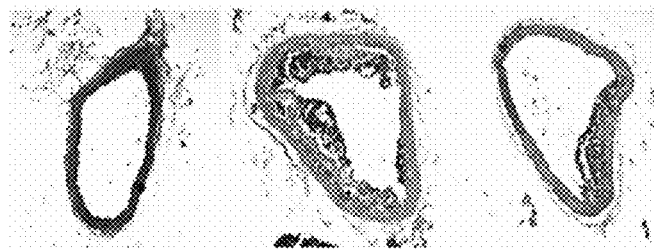
FIG. 11C shows images of Oil Red O and H&E stained histologic sections of representative aortas from LDLR-KO mice fed a normal diet or fed a high cholesterol diet and administered at 12 weeks either the AAV2/8.eNOXpr-3xFLAG-mCherry vector or the AAV2/8.eNOXpr-FOXP3(P1)-IL10 vector.
Figure 11D:
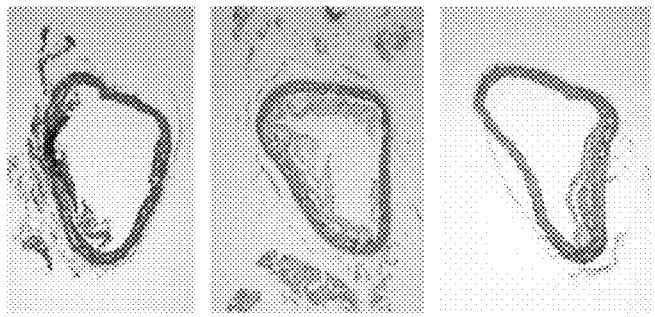
FIG. 11D shows images of H&E stained histologic sections of representative aortas from LDLR-KO mice fed a normal diet or fed a high cholesterol diet and administered at 12 weeks either the AAV2/8.eNOXpr-3xFLAG-mCherry vector or the AAV2/8.eNOXpr-FOXP3(P1)-IL10 vector.

For histological staining, aortas were fixed in 4% paraformaldehyde, dehydrated using sucrose, and embedded in OCT (Sakura, USA). Representative histologic sections from each of the three animal groups were Oil Red O/hematoxylin and eosin (H&E) stained (FIG. 11C) as well as simple H&E stained (FIG. 11D). The AAV2/8.eNOXpr-3xFLAGmCherry vector-treated group fed a HCD (Group 2) showed much higher levels of red staining indicating more atherosclerotic plaque formation than either the normal diet control mice (Group 1) or the AAV2/8.eNOXpr-FOXP3(P1)-IL10 vector-treated mice fed a HCD (Group 3), suggesting a therapeutic effect from FOXP3(P1)-IL10 gene delivery. Simple H&E stained sections showed similar results.

Example 8

High Resolution Ultrasound Analysis Following Administration of AAV2/8.eNOXpr-FoxP3(P1)-IL10 to an Animal Model of Established and Ongoing Atherosclerosis Blood velocity is used as a general indicator of vascular health. For example, high blood velocity can be indicative of disease resulting from vascular pathologies, such as atherosclerotic plaques. High resolution ultrasound (HRUS) imaging was used to measure blood velocity and aorta wall thickness, as a measurement of therapeutic effect between the three animal groups at week 20: the AAV2/8.eNOXpr-FOXP3(P1)-IL10 vector-treated experimental group (Group 3), the ND negative control group (Group 1), and the AAV2/8.eNOXpr-3xFLAGmCherry disease positive control group (Group 2).

The animals were fasted for 8 hours before ultrasound imaging using a Fujifilm VisualSonic Vevo2100 (Toronto, Canada) high-resolution imaging system with an RMV 70B transducer and having a center frequency of 30 MHz. The mice were anesthetized using 1.5% isoflurane (Isothesia, Abbott Laboratories, Chicago, USA) with oxygen. The abdominal and thoracic region hair was removed by chemical hair remover (Veet, USA). The mice were laid supine out on a thermostatically heated platform. A pre-warmed transducing gel (Medline Industries, Inc., Mundelein, USA) was spread over the skin as a coupling medium for more accurate measurements. Image acquisition was started on B-mode and images of aortic arch, thoracic, and abdominal region of aorta were recorded. Then, aorta wall thickness of aorta arch, thoracic and abdominal region of aorta were scanned on M-mode. Next, the scan head probe was turned 90° for a short-axis view to visualize the cross-sectional area of the aorta. Measurement of the flow velocity, orientation of the abdominal aorta by ultrasound, was accomplished by tilting the platform and the head of mouse down with the transducer probe towards the feet and tail of the mouse. This positioning resulted in the Doppler angle to be less than 60° for accurate measurements of blood flow velocity in the pulse-wave Doppler (PW) mode within aorta arch and abdominal aorta. Off-line measurements and data analysis were performed using the Vevo2100 Analytical Software. The complete imaging for each mouse lasted for about 25-30 min.

Figure 12:
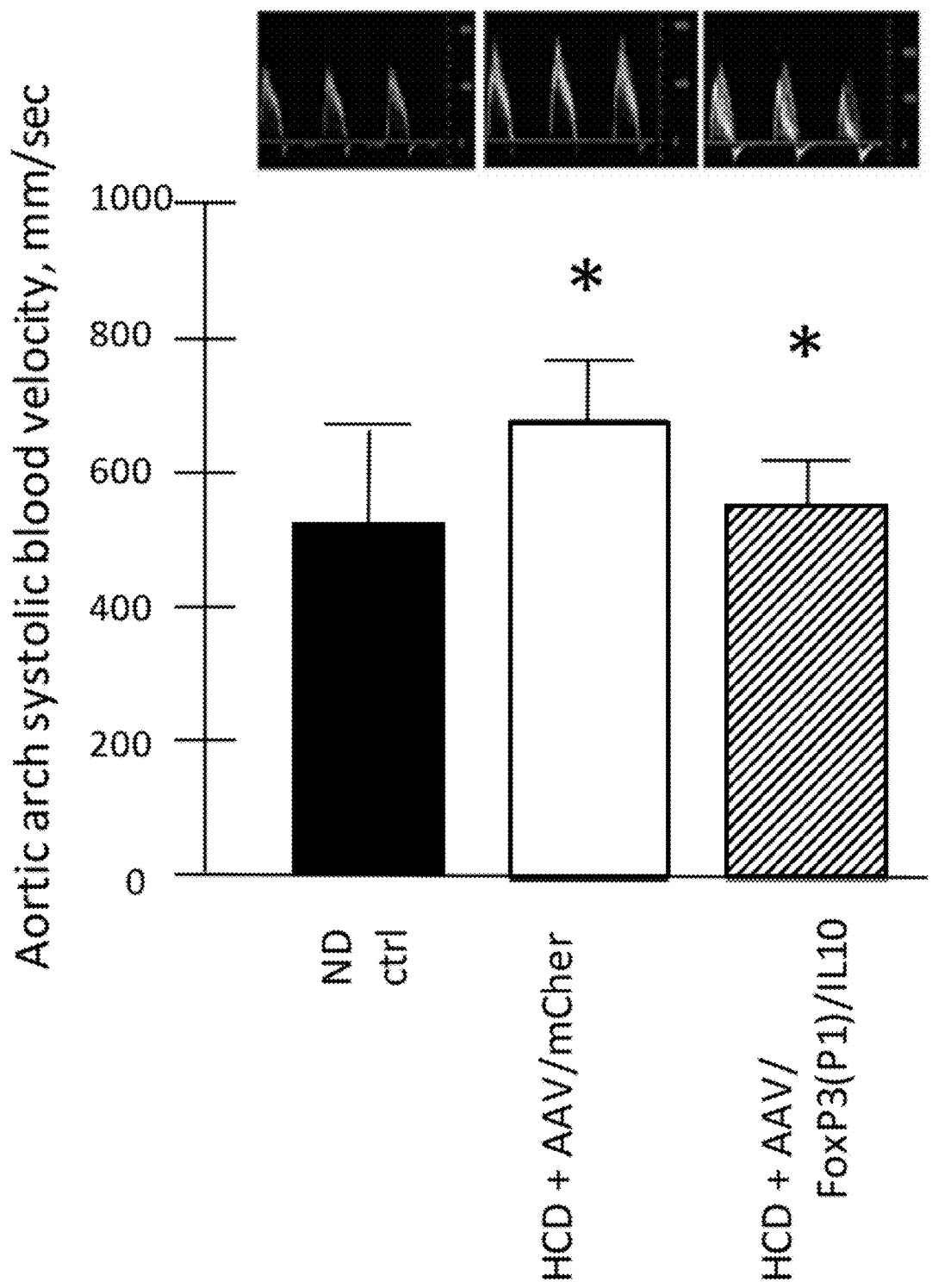
FIG. 12 shows high-resolution ultrasound imaging and systolic blood velocity in the aortic arch of LDLR-KO mice fed a normal diet or fed a high cholesterol diet and administered at 12 weeks either the AAV2/8.eNOXpr-3xFLAG-mCherry vector or the AAV2/8.eNOXpr-FOXP3(P1)-IL10 vector. (*P<0.05).

Blood flow velocities in the luminal center of the aorta were measured by HRUS and representative images from the analysis were captured (FIG. 12). The systolic blood velocity (systolic pulse wave velocity) in the aortic arch of the AAV2/8.eNOXpr-3xFLAGmCherry animals maintained on a HCD (Group 2; 676±94 mm/sec) was significantly higher (p<0.05) than the negative control animals maintained on a ND (Group 1; 532±133 mm/sec), indicating the presence of vascular pathology in the disease group. Moreover, the aortic arch systolic blood velocity of the AAV2/8.eNOXpr-FOXP3(P1)-IL10 vector-treated experimental animals maintained on a HCD (Group 3; 549±73 mm/sec) was about 70% lower (p<0.05) than the disease positive control group (Group 2) and nearly reached the blood velocity level of the ND negative control group (Group 1). All data were given as means±SD (*P<0.05).

Figure 13:
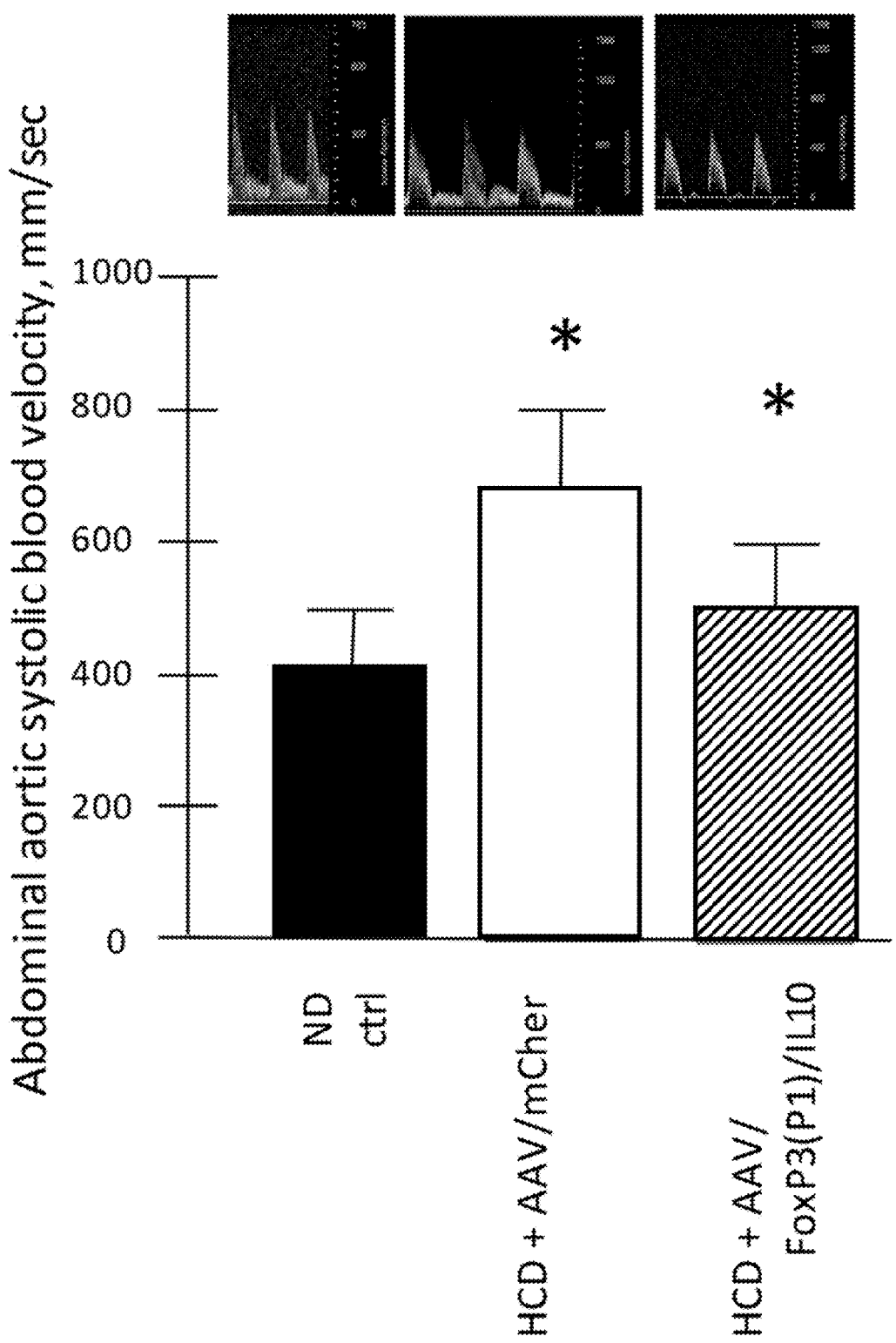
FIG. 13 shows high-resolution ultrasound imaging and systolic blood velocity in the abdominal region of the aorta of LDLR-KO mice fed a normal diet or fed a high cholesterol diet and administered at 12 weeks either the AAV2/8.eNOXpr-3xFLAG-mCherry vector or the AAV2/8.eNOXpr-FOXP3(P1)-IL10 vector. *P<0.05.

FIG. 13 shows that the systolic blood velocity (systolic pulse wave velocity) in the abdominal region of the aorta among animal groups. The abdominal aortic systolic blood velocity of the AAV2/8.eNOXpr-3xFLAGmCherry animals maintained on a HCD (Group 2; 681±129 mm/sec) was significantly higher than the negative control animals maintained on a ND (Group 1; 418±88 mm/sec), indicative of vascular pathology in the disease group. Moreover, the abdominal aortic systolic blood velocity of the AAV2/8.eNOXpr-FOXP3(P1)-IL10 vector-treated experimental animals maintained on a HCD (Group 3; 495±78 mm/sec) was about 63% lower (p<0.05) than the disease positive control group (Group 2) and nearly reached the blood velocity level of the ND negative control group (Group 1). All data were given as means±SD (*P<0.05).

Figure 14:
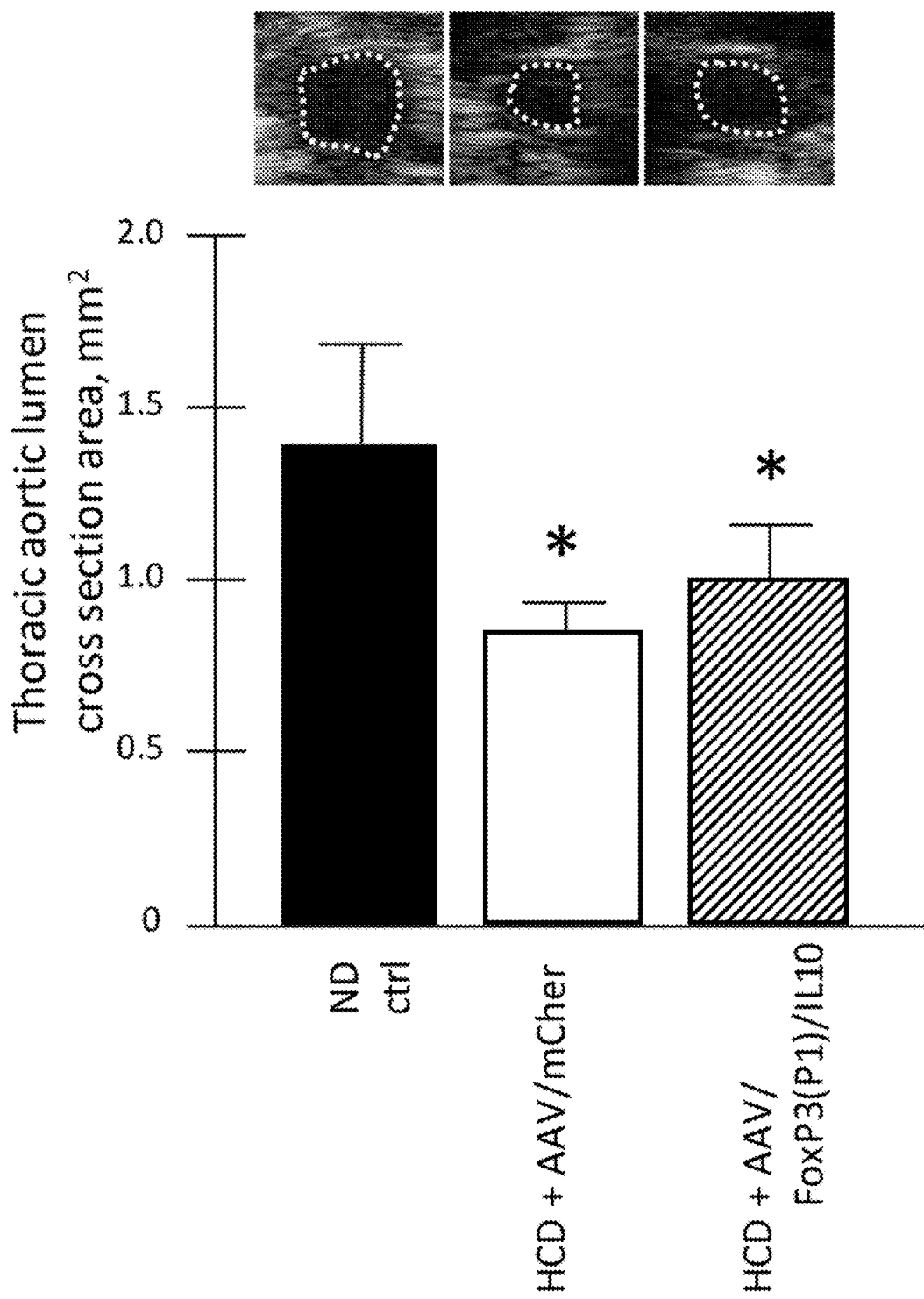
FIG. 14 shows high-resolution ultrasound imaging and cross-sectional area of the thoracic region of the aortas of LDLR-KO mice fed a normal diet or fed a high cholesterol diet and administered at 12 weeks either the AAV2/8.eNOXpr-3xFLAG-mCherry vector or the AAV2/8.eNOXpr-FOXP3(P1)-IL10 vector. *P<0.05.

HRUS was used to image and measure the cross-sectional area of the thoracic region of the aortas of each animal group (FIG. 14). The cross-sectional area of the lumens of the aortas was significantly smaller in the AAV2/8.eNOXpr-3xFLAGmCherry disease positive control group (Group 2; 0.84±0.11 $mm^2$) compared to the ND negative control group (Group 1; 1.47±0.22 $mm^2$), which is consistent with the higher systolic blood velocity observed in the disease group. In addition, the cross-sectional area of the lumens of the aortas was significantly larger in the AAV2/8.eNOXpr-FOXP3(P1)-IL10 vector-treated experimental group (Group 3; 1.00±0.17 $mm^2$) than the disease positive control group (Group 2). That observation is also consistent with the lower blood velocity observed in the AAV2/8.eNOXpr-FOXP3 (P1)-IL10 vector-treated group. All data were given as means±SD (*P<0.05).

Figure 15:
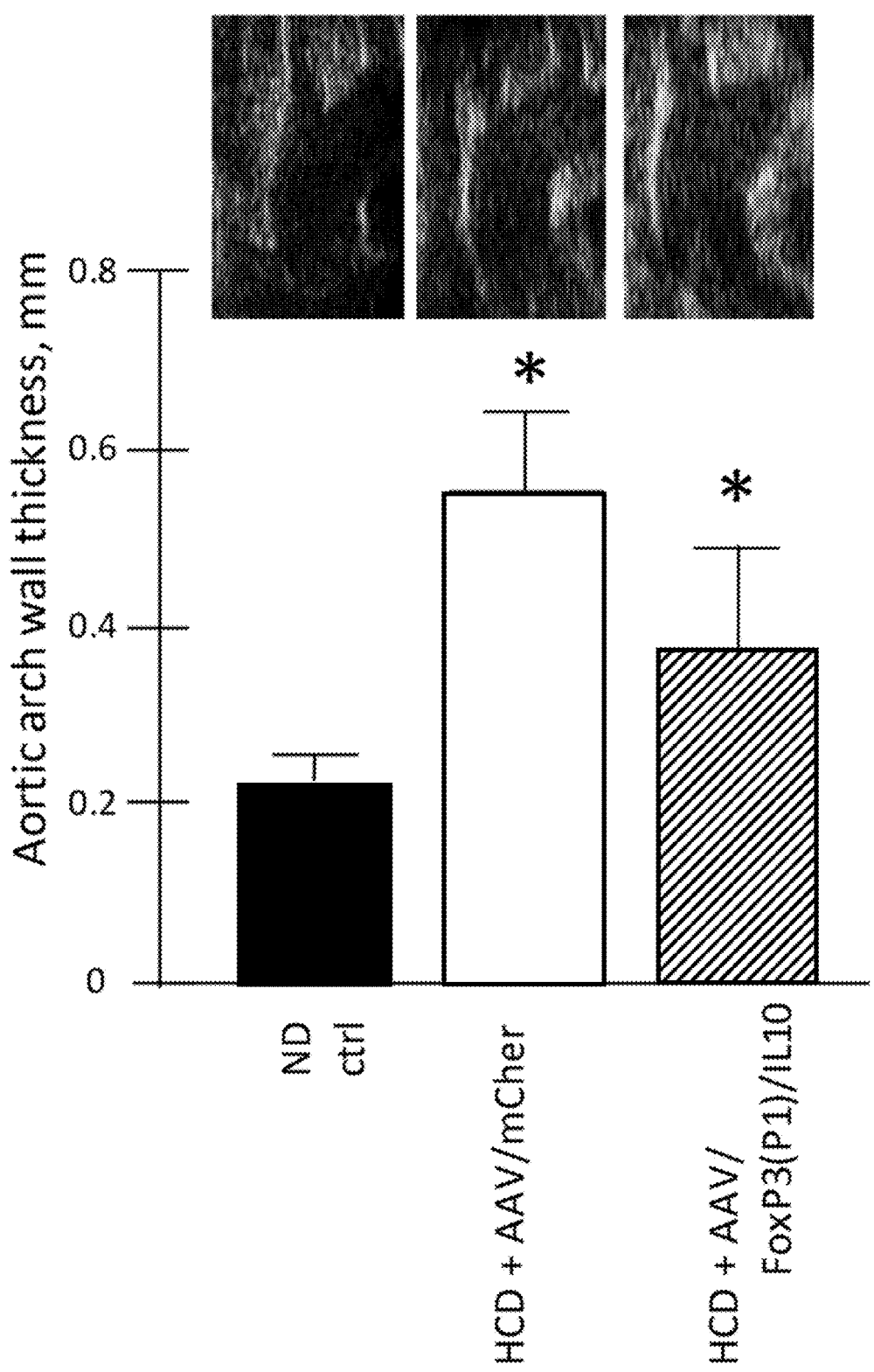
FIG. 15 shows high-resolution ultrasound imaging and wall thickness of the aorta arch region of LDLR-KO mice fed a normal diet or fed a high cholesterol diet and administered at 12 weeks either the AAV2/8.eNOXpr-3xFLAG-mCherry vector or the AAV2/8.eNOXpr-FOXP3(P1)-IL10 vector. *P<0.05.

HRUS was used to image and measure the wall thickness of the aorta arch region (FIG. 15). The images included in FIG. 15 are representative of those captured during the analysis. The aortic wall thickness of the AAV2/8.eNOXpr-3xFLAGmCherry disease positive control group (Group 2; 0.54±0.88 mm) was significantly thicker than the ND negative control group (Group 1; 0.21±0.02 mm), consistent with the presence of vascular pathology in the disease group. Notably, the aortic wall thickness of the AAV2/8.eNOXpr-FOXP3(P1)-IL10 vector-treated experimental group (Group 3; 0.38±0.10 mm) was significantly thinner than the disease positive control group (Group 2). All data were given as means±SD (*P<0.05).

The HRUS analysis for systolic blood velocity, lumen cross sectional area, and wall thickness showed significantly less vascular pathology for the FOXP3(P1)-IL10 AAV vector-treated animals maintained on a HCD (Group 3) compared to the animals maintained on a HCD diet and administered the FLAG-mCherry AAV vector (Group 2). The lower systolic blood velocities (FIG. 12 and FIG. 13), larger aortic lumens (FIG. 14), and thinner aortic wall thickness (FIG. 15) observed among the AAV2/8.eNOXpr-FOXP3 (P1)-IL10 vector-treated animals maintained on a HCD (Group 3) evidences significantly less overall vascular pathology compared to the AAV2/8.eNOXpr-3xFLAGmCherry animals maintained on a HCD (Group 2). These results are consistent with histological studies described in Example 7. Overall, these data suggest that FOXP3(P1)-IL10 gene delivery was therapeutically efficacious in a mouse model of established and ongoing atherosclerosis.

CITED REFERENCES

The complete disclosures of all publications cited herein are incorporated herein by reference in their entireties as if each were individually set forth in full herein and incorporated.

Asadullah K, et al., "Interleukin-10 therapy—Review of a new approach." *Pharmacol Rev.* 2003 55(2):241-69.

Batchu R B, et al., "Cloning, expression, and purification of full length Rep78 of adeno-associated virus as a fusion protein with maltose binding protein in *Escherichia coli*" *Biochem Biophys Res Commun.* 1995, 208(2):714-20.

Brooks D G, et al., "Interleukin-10 determines viral clearance or persistence in vivo." *Nat Med.* 2006, 12(11):1301-9.

Brooks D G, et al., "IL-10 blockade facilitates DNA vaccine-induced T cell responses and enhances clearance of persistent virus infection." *J Exp Med.* 2008, 205(3):533-41.

Cao M, et al., "AAV2/8-humanFOXP3 gene therapy shows robust anti-atherosclerosis efficacy in LDLR-KO mice on high cholesterol diet." *J Transl Med.* 2015, 13:235, doi: 10.1186/s12967-015-0597-7.

Cao M, et al., "Dual AAV/IL-10 plus STAT3 anti-inflammatory gene delivery lowers atherosclerosis in LDLR KO Mice, but without increased benefit." *Int J Vasc Med.* 2012, 2012:524235, 10.1155/2012/524235, Epub 2011.

Cao M, et al., "The X gene of adeno-associated virus 2 (AAV2) is involved in viral DNA replication." *PLoS One* 2014, 9(8):e104596, doi: 10.1371/journal.pone.0104596.

Cecchini S, et al., "Reproducible high yields of recombinant adeno-associated virus produced using invertebrate cells in 0.02- to 200-liter cultures." *Hum Gene Ther.* 2011, 22(8):1021-30.

Chen J, et al, "Lectin-like oxidized low-density lipoprotein receptor-1 (LOX-1) transcriptional regulation by Oct-1 in human endothelial cells: implications for atherosclerosis." *Biochem. J.* 2006, 393(Pt 1):255-65.

Chen J, et al., "Molecular dissection of angiotensin II-activated human LOX-1 promoter." *Arterioscler Thromb Vasc Biol.* 2006, 26(5):1163-8.

Chen J, et al., "SHP2 inhibitor PHPS1 protects against atherosclerosis by inhibiting smooth muscle cell proliferation." *BMC Cardiovasc Disord.* 2018, 18(1):72, doi: 10.1186/s12872-018-0816-2.

Clemons K V, et al., "Role of IL-10 in invasive aspergillosis: increased resistance of IL-10 gene knockout mice to lethal systemic aspergillosis." *Clin Exp Immunol.* 2000, 122(2): 186-91.

Dandapat A, et al., "Over-expression of angiotensin II type 2 receptor (agtr2) decreases collagen accumulation in atherosclerotic plaque." *Biochem Biophys Res Commun.* 2008, 366(4):871-7. Epub 2007. doi:10.1016/j.bbrc.2007.11.061.

Dandapat A, et al., "Overexpression of TGFbeta1 by adeno-associated virus type-2 vector protects myocardium from ischemia-reperfusion injury." *Gene Ther.* 2008, 15(6): 415-23. Epub 2007.

dela Paz N G, et al., "Regulation of NF-κB-dependent gene expression by the POU domain transcription factor Oct-1." *J Blol Chem.* 2007, 282(11):8424-34. Epub 2006.

Deng G, et al., "Foxp3 post-translational modifications and Treg suppressive activity." *Front Immunol.* 2019, 10:2486, doi: 10.3389/fimmu.2019.02486.

Ejrnaes M, et al., "Resolution of a chronic viral infection after interleukin-10 receptor blockade." *J Exp Med.* 2006, 203(11):2461-72.

Filippi C M and von Herrath M G, "IL-10 and the resolution of infections." *J Pathol.* 2008, 214(2):224-30.

Fontenot J D, et al., "Foxp3 programs the development and function of CD4+CD25+ regulatory T cells." *Nat Immunol.* 2003, 4(4):330-6.

Ganguli A, et al., "Distinct NF-κB regulation by shear stress through Ras-dependent IκBα oscillations: real-time analysis of flow-mediated activation in live cells." *Circ Res.* 2005, 96(6):626-34.

Getz G S and Reardon C A, "Diet and murine atherosclerosis." *Arterioscler Thromb Vasc Biol.* 2006, 26(2):242-9. Epub 2005.

Gregersen S, et al., "Inflammatory and oxidative stress responses to high-carbohydrate and high-fat meals in healthy humans." *J Nutr Metab.* 2012, 2012:238056, doi: 10.1155/2012/238056.

Grimm D, et al., "Novel tools for production and purification of recombinant adenoassociated virus vectors." *Hum Gene Ther.* 1998, 9(18):2745-60.

Hermonat P L, et al., "Genetics of adeno-associated virus: isolation and preliminary characterization of adeno-associated virus type 2 mutants." *J Virol.* 1984a, 51(2):329-39.

Hermonat P L, et al., "Use of adeno-associated virus as a mammalian DNA cloning vector: transduction of neomycin resistance into mammalian tissue culture cells." *Proc Natl Acad Sci USA.* 1984b, 81(20):6466-70.

Hermonat P L, et al., "The adeno-associated virus Rep78 major regulatory/transformation suppressor protein binds cellular Sp1 in vitro and evidence of a biological effect." *Cancer Res.* 1996, 56(22):5299-304.

Hermonat P L and R B Batchu, "The adeno-associated virus Rep78 major regulatory protein forms multimeric complexes and the domain for this activity is contained within the carboxy-half of the molecule." *FEBS Lett.* 1997a, 401(2-3):180-4.

Hermonat P L, et al., "Multiple cellular proteins are recognized by the adeno-associated virus Rep78 major regulatory protein and the amino-half of Rep78 is required for many of these interactions." *Biochem Mot Blol Int.* 1997b, 43(2):409-20.

Hermonat P L, et al., "The packaging capacity of adeno-associated virus (AAV) and the potential for wild-type-plus AAV gene therapy vectors." *FEBS Lett.* 1997c, 407(1):78-84.

Hermonat P L, et al., "The adeno-associated virus Rep78 major regulatory protein binds the cellular TATA-binding protein in vitro and in vivo." *Virology.* 1998, 245(1): 120-7.

Hermonat P L. "The first adeno-associated virus gene transfer experiment, 1983." *Hum Gene Ther.* 2014, 25(6):486-7.

Hori S, et al., "Control of regulatory T cell development by the transcription factor Foxp3." *Science.* 2003, 299 (5609):1057-61.

Hsieh H J, et al., "Shear-induced endothelial mechanotransduction: the interplay between reactive oxygen species (ROS) and nitric oxide (NO) and the pathophysiological implications." *J Biomed Sci.* 2014, 12:3 doi:10.1186/1423-0127-21-3.

Hwang J, et al., "Pulsatile versus oscillatory shear stress regulates NADPH oxidase subunit expression: implication for native LDL oxidation." *Circ Res.* 2003, 93(12): 1225-32.

Jenuwein T and Grosschedl R, "Complex pattern of immunoglobulin gene expression in normal and transgenic mice: nonoverlapping regulatory sequences govern distinct tissue specificities." *Genes Dev.* 1991, 5(6):932-43.

Karagiannidis C, et al., "Glucocorticoids upregulate FOXP3 expression and regulatory T cells in asthma." *J Allergy Clin Immunol.* 2004, 114(6):1425-33.

Khan J A, et al., "Systemic human Netrin-1 gene delivery by adeno-associated virus type 8 alters leukocyte accumulation and atherogenesis in vivo." *Gene Ther.* 2011, 18(5): 437-44, Epub 2010.

Khan J A, et al., "AAV/hSTAT3-gene delivery lowers aortic inflammatory cell infiltration in LDLR KO mice on high cholesterol." *Atherosclerosis.* 2010, 213(1):59-66. doi: 10.1016/jatherosclerosis.2010.07.029.

Khattri R, et al., "An essential role for Scurfin in CD4+CD25+T regulatory cells." *Nat Immunol.* 2003, 4(4):337-42.

Kim J, et al., "Molecular networks of FOXP family: dual biologic functions, interplay with other molecules and clinical implications in cancer progression." *Mol Cancer.* 2019, 18(1):180, doi:10.1186/212943-019-1110-3.

Kitoh A, et al., "Indispensable role of the Runx1-Cbfbeta transcription complex for in vivo-suppressive function of FoxP3+ regulatory T cells." *Immunity.* 2009, 31(4):609-20.

Konopacki C, et al., "Transcription factor Foxp1 regulates Foxp3 chromatin binding and coordinates regulatory T cell function." *Nat Immunol.* 2019, 20(2):232-42.

Kunsch C, et al., "Selection of optimal kappa B/Rel DNA-binding motifs: interaction of both subunits of NF-kappa B with DNA is required for transcriptional activation." *Mol Cell Biol.* 1992, 12(10):4412-21.

Kuwano Y, et al., "Interferon-gamma activates transcription of NADPH oxidase 1 gene and upregulates production of superoxide anion by human large intestinal epithelial cells." *Am J Physiol Cell Physiol.* 2006 (Epub 2005), 290(2):C433-43.

Labow M A, et al., "Positive and negative autoregulation of the adeno-associated virus type 2 genome." *J Virol.* 1986, 60(1):251-8.

LaFace D, et al., "Gene transfer into hematopoietic progenitor cells mediated by the adeno-associated virus vector." *Virology.* 1988, 162(2):483-6.

Li B, et al., "FOXP3 is a homo-oligomer and a component of a supramolecular regulatory complex disabled in the human XLAAD/IPEX autoimmune disease." *Int Immunol.* 2007, 19(7):825-35.

Li D, et al., "Suppression of atherogenesis by delivery of TGFbeta1ACT using adeno-associated virus type 2 in LDLR knockout mice." *Biochem Biophys Res Commun.* 2006, 344(3):701-7.

Li Z, et al., "FOXP3+ regulatory T cells and their functional regulation." *Cell Mol Immunol.* 2015, 12(5):588-65.

Liu Y, et al., "Inhibition of atherogenesis in LDLR knockout mice by systemic delivery of adeno-associated virus type 2-hIL-10." *Atherosclerosis.* 2006, 188(1):19-27. Epub 2005.

Liu Y, et al., "Rapid induction of cytotoxic T-cell response against cervical cancer cells by human papillomavirus type 16 E6 antigen gene delivery into human dendritic cells by an adeno-associated virus vector." *Cancer Gene Ther.* 2001, 8(12):948-57.

Manea A, et al., "JAK/STAT signaling pathway regulates Nox1 and Nox4-based NADPH Oxidase in human aortic smooth muscle cells." *Arterioscler Thromb Vasc Biol.* 2010 (Epub 2009), 30(1):105-12.

Maris C H, et al., "Interleukin-10 plays an early role in generating virus-specific T cell anergy." *BMC Immunol.* 2007, 8:8, doi:10.1186/1471-2172-8-8.

Mercurio F and Manning A M, "NF-κB as a primary regulator of the stress response." *Oncogene.* 1999, 18(45): 6163-71.

Neyns B, et al., "Characterization of permanent cell lines that contain the AAV2 rep-cap genes on an Epstein-Barr-virus-based episomal plasmid. *Intervirology.* 2001, 44(4): 255-63.

Nguyen Dinh Cat A, et al., "Angiotensin II, NADPH oxidase, and redox signaling in the vasculature." *Antioxid Redox Signal.* 2013 (Epub 2012), 19(10):1110-20.

Pan J H, et al., "Macrophage migration inhibitory factor deficiency impairs atherosclerosis in low-density lipoprotein receptor-deficient mice." *Circulation.* 2004, 109(25): 3149-53.

Ren J, et al., "Foxp1 is critical for the maintenance of regulatory T-cell homeostasis and suppressive function." *PLoS Biol.* 2019, 17(5):e3000270, doi: 10.1371/journal.pbio.3000270.

Rudra D, et al., "Transcription factor Foxp3 and its protein partners form a complex regulatory network." *Nat Immunol.* 2012, 13(10):1010-9.

Song X, et al., "Structural and biological features of FOXP3 dimerization relevant to regulatory T cell function." *Cell Rep.* 2012, 1(6):665-75.

Takano T and Cybulsky A V, "Complement C5b-9-mediated arachidonic acid metabolism in glomerular epithelial cells: role of cyclooxygenase-1 and -2." *Am J Pathol.* 2000, 156(6):2091-101.

Udalova I A, et al., "Quantitative prediction of NF-kappa B DNA-protein interactions." *Proc Natl Acad Sci USA.* 2002, 99(12): 8167-72.

Valente A J, et al., "Regulation of NOX1 expression by GATA, HNF-1alpha, and Cdx transcription factors." *Free Radic Biol Med.* 2008 (Epub 2007), 44(3): 430-43.

Voleti B and Agrawal A, "Regulation of basal and induced expression of C-reactive protein through an overlapping element for OCT-1 and NF-kappaB on the proximal promoter." *J Immunol.* 2005, 175(5):3386-90.

Wan F and Lenardo M, "Specification of DNA Binding Activity of NF-κB Proteins." *Cold Spring Harb Perspect Biol.* 2009, 1(4):a000067.

Wang B, et al., "Multiple domains define the expression and regulatory properties of Foxp1 forkhead transcriptional repressors." *J Blol Chem.* 2003, 278(27):24259-68.

Wong D, et al., "Extensive characterization of NF-κB binding uncovers non-canonical motifs and advances the interpretation of genetic functional traits." *Genome Biol.* 2011, 12(7):R70, doi: 10.1186/gb-2011-12-7-r70, pages 1-18.

Yang A T, et al., "TGF-β1 induces the dual regulation of hepatic progenitor cells with both anti- and proliver fibrosis." *Stem Cells Int.* 2016, 2016:1492694. doi: 10.1155/2016/1492694. Epub 2015.

Zadelaar S, et al., "Mouse models for atherosclerosis and pharmaceutical modifiers." *Arterioscler Thromb Vasc Biol.* 2007, 27(8):1706-21.

Zeni E, et al., "Macrophage expression of interleukin-10 is a prognostic factor in nonsmall cell lung cancer." *Eur Respir J.* 2007, 30(4):627-32.

Zhang Q, et al., "30 Years of NF-κB: A Blossoming of Relevance to Human Pathobiology." *Cell.* 2017, 168(1-2):37-57.

Zhao F Q, "Octamer-binding transcription factors: genomics and functions." Published in final edited form as *Front Biosci* (Landmark Ed). 2013, 18:1051-71.

Zhu H, et al., "AAV2/8-hSMAD3 gene delivery attenuates aortic atherogenesis, enhances Th2 response without fibrosis, in LDLR-KO mice on high cholesterol diet." *J Transl Med.* 2014, 12:252, doi: 10.1186/s12967-014-0252-8.

Zhu H, et al., "Comparison of efficacy of the disease-specific LOX1- and constitutive cytomegalovirus-promoters in expressing interleukin 10 through adeno-associated virus 2/8 delivery in atherosclerotic mice." *PLoS One.* 2014, 9(4):e94665, doi: 10.1371/journal.pone.0094665.

Ziegler S, "FOXP3: Of Mice and Men." *Annu. Rev. Immunol.* 2006, 24:209-26.

Zobel K, et al., "Interleukin 6, lipopolysaccharide-binding protein and interleukin 10 in the prediction of risk and etiologic patterns in patients with community-acquired pneumonia: results from the German competence network CAPNETZ." *BMC Pulm Med.* 2012, 12:6, doi: 10.1186/1471-2466-12-6.

EQUIVALENTS

The foregoing written specification is considered to be sufficient to enable one skilled in the art to practice the embodiments. The foregoing description and Examples detail certain embodiments and describes the best mode contemplated by the inventors. It will be appreciated, however, that no matter how detailed the foregoing may appear in text, the embodiment may be practiced in many ways and should be construed in accordance with the appended claims and any equivalents thereof.

As used herein, the term about refers to a numeric value, including, for example, whole numbers, fractions, and percentages, whether or not explicitly indicated. The term about generally refers to a range of numerical values (e.g., +/−5-10% of the recited range) that one of ordinary skill in the art would consider equivalent to the recited value (e.g., having the same function or result). When terms such as at least and about precede a list of numerical values or ranges, the terms modify all of the values or ranges provided in the list. In some instances, the term about may include numerical values that are rounded to the nearest significant figure.

That is claimed is:

1. An isolated nucleic acid molecule comprising a NOX1 core promoter comprising the nucleotide sequence of SEQ ID NO: 3.

2. The isolated nucleic acid molecule of claim 1, wherein the NOX1 core promoter is less than 500 nucleotides.

3. The isolated nucleic acid molecule of claim 1, further comprising at least one heterologous NFκB binding site.

4. The isolated nucleic acid molecule of claim 3, wherein the at least one heterologous NFκB binding site comprises the nucleotide sequence of SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, or SEQ ID NO: 20.

5. The isolated nucleic acid molecule of claim 1, comprising at least one heterologous Oct1 binding site.

6. The isolated nucleic acid molecule of claim 5, wherein the at least one Oct1 binding site comprises the nucleotide sequence of SEQ ID NO: 21.

7. The isolated nucleic acid molecule of claim 1, further comprising a heterologous nucleotide sequence encoding at least one anti-inflammatory molecule or at least one reporter protein operatively linked to the NOX1 core promoter.

8. The isolated nucleic acid molecule of claim 7, wherein the at least one anti-inflammatory molecule is (a) a wildtype or variant FOXP3 polypeptide, (b) IL10, or (c) a wildtype or variant FOXP3 polypeptide and IL10.

9. The isolated nucleic acid molecule of claim 8, wherein the wildtype or variant FOXP3 polypeptide comprises the amino acid sequence of SEQ ID NO: 24 or SEQ ID NO: 28.

10. The isolated nucleic acid of claim 1, further comprising a nucleotide sequence encoding a variant FOXP polypeptide comprising the amino acid sequence of a first FOXP polypeptide, wherein a zinc finger and leucine zipper region of the first FOXP polypeptide has been replaced with a zinc finger and leucine zipper region of a second FOXP polypeptide operatively linked to the NOX1 core promoter.

11. The isolated nucleic acid of claim 10, wherein:
  a) the first FOXP polypeptide is a FOXP3 polypeptide and the second FOXP polypeptide is a FOXP1 polypeptide, a FOXP2 polypeptide, or a FOXP4 polypeptide;
  b) the first FOXP polypeptide is a FOXP1 polypeptide and the second FOXP polypeptide is a FOXP2 polypeptide, a FOXP3 polypeptide, or a FOXP4 polypeptide;
  c) the first FOXP polypeptide is a FOXP2 polypeptide and the second FOXP polypeptide is a FOXP1 polypeptide, a FOXP3 polypeptide, or a FOXP4 polypeptide; or
  d) the first FOXP polypeptide is a FOX4 polypeptide and the second FOXP polypeptide is a FOXP1 polypeptide, a FOXP2 polypeptide, or a FOXP3 polypeptide.

12. The isolated nucleic acid of claim 10, wherein the zinc finger and leucine zipper region of the second FOXP polypeptide comprises the amino acid sequence of SEQ ID NO: 27.

13. The isolated nucleic acid of claim 1, further comprising a nucleotide sequence encoding a variant FOXP polypeptide operatively linked to the NOX1 core promoter, wherein the variant FOXP polypeptide comprises an amino acid sequence having at least 97%, at least 98%, at least 99%, or 100% sequence identity to the amino acid sequence of SEQ ID NO: 28.

14. An isolated nucleic acid comprising the nucleotide sequence of SEQ ID NO: 34.

15. The isolated nucleic acid of claim 13, further comprising a nucleotide sequence encoding a cytokine, a growth factor, or a chemokine operatively linked to the NOX1 core promoter.

16. The isolated nucleic acid of claim 13, further comprising a nucleotide sequence encoding the amino acid sequence of SEQ ID NO: 31.

17. A vector comprising the nucleic acid of claim 8.

18. A cultured host cell comprising the nucleic acid molecule of claim 8.

19. A pharmaceutical composition comprising the vector of claim 17.

20. A method comprising administering to a subject the cultured host cell of claim 18.

21. A method of treating a subject comprising administering to the subject the vector of claim 17.

22. The method of claim 21, wherein the subject has a vascular disease, a cardiovascular disease, an inflammation-associated disease, and/or an age-associated disease.

23. The method of claim 21, wherein the subject has atherosclerosis, arthritis, psoriatic arthritis, rheumatoid arthritis, gouty arthritis, dementia, Alzheimer's disease, asthma, macular degeneration of the retina, arterial disease of the aorta, carotid artery disease, coronary artery disease, atherosclerotic cerebrovascular disease, peripheral artery disease, and/or diabetes mellitus.

24. The method of claim 21 wherein the vector is administered to the subject or the animal via intravenous injection, arterial injection, intramuscular injection, or injection into a section of ligated artery or vein.

25. An isolated nucleic acid comprising the nucleotide sequence of SEQ ID NO: 4.

26. A vector comprising the nucleic acid of claim 14.

27. A vector comprising the nucleic acid of claim 16.

28. The vector of claim 17, wherein the vector is an adeno-associated virus (AAV) vector.

29. The vector of claim 26, wherein the vector is an adeno-associated virus (AAV) vector.

30. The vector of claim 27, wherein the vector is an adeno-associated virus (AAV) vector.

* * * * *